(12) United States Patent
Li et al.

(10) Patent No.: US 10,500,169 B2
(45) Date of Patent: Dec. 10, 2019

(54) SUPRESSION OF IGE PRODUCTION BY COMPOUNDS DERIVED FROM TRADITIONAL CHINESE MEDICINE

(71) Applicants: Xiu-Min Li; Sean N. Parker Foundation, Palo Alto, CA (US)

(72) Inventors: Xiu-Min Li, Mamaroneck, NY (US); Nan Yang, Flushing, NY (US); Chaoyi Mao, Beijing (CN); Ying Song, Elmhurst, NY (US); Sean N. Parker, Palo Alto, CA (US)

(73) Assignees: Xiu-Min Li, Mamaroneck, NY (US); Sean N. Parker Foundation, Palo Alto, CA (US)

(*) Notice: Subject to any disclaimer, the term of this patent is extended or adjusted under 35 U.S.C. 154(b) by 0 days.

(21) Appl. No.: 14/857,772

(22) Filed: Sep. 17, 2015

(65) Prior Publication Data
US 2016/0175291 A1 Jun. 23, 2016

Related U.S. Application Data

(60) Provisional application No. 62/051,441, filed on Sep. 17, 2014.

(51) Int. Cl.
| | |
|---|---|
| A61K 31/44 | (2006.01) |
| A61K 31/35 | (2006.01) |
| A61K 31/12 | (2006.01) |
| A61K 31/122 | (2006.01) |
| A61K 31/366 | (2006.01) |
| A61K 31/475 | (2006.01) |
| A61K 31/4745 | (2006.01) |

(52) U.S. Cl.
CPC ............ *A61K 31/122* (2013.01); *A61K 31/12* (2013.01); *A61K 31/35* (2013.01); *A61K 31/366* (2013.01); *A61K 31/475* (2013.01); *A61K 31/4745* (2013.01)

(58) Field of Classification Search
CPC ....... A61K 31/475; A61K 31/35; A61K 31/12
USPC ........................................ 514/280, 453, 680
See application file for complete search history.

(56) References Cited

U.S. PATENT DOCUMENTS

| | | | | |
|---|---|---|---|---|
| 6,245,781 B1* | 6/2001 | Upadhyay | .......... | A61K 31/4745 514/320 |
| 6,630,176 B2* | 10/2003 | Li | ................ | A61K 36/074 424/195.16 |
| 7,344,739 B2* | 3/2008 | Palpu | ................ | A61K 36/185 424/734 |
| 7,820,175 B2* | 10/2010 | Li | ................ | A61K 36/074 424/195.15 |

OTHER PUBLICATIONS

Srivastava et al. The Chinese herbal medicine formula FAHF-2 completely blocks anaphylactic reactions in a murine model of peanut allergy J. Allergy Clin. Immunol. 115, pp. 171-178 (2005).*
Song et al. Food allergy herbal formula 2 protection against peanut anaphylactic reaction is via inhibition of mast cells and basophils. J. Allergy.Clin. Immunol. 126, pp. 1208-1217 (2010).*
Yang et al. Berberine and limonin suppress IgE production by human B cells and peripheral blood mononuclear cells from food-allergic patients. Ann Allergy Asthma Immunol 113, pp. 556-564 (available online Aug. 22, 2014).*
Kattan JD et al. "Pharmacological and immunological effects of individual herbs in the Food Allergy Herbal Formula-2 (FAHF-2) on peanut allergy". Phytother Res. 2008;22:651-659.
Breksa AP, III et al. "Isolation and identification of the first C-17 limonin epimer, epilimonin". JAgric Food Chem. 2008;56:5595-5598.
Hasada Ket al. "Application of I H-NMR spectroscopy to validation of berberine alkaloid reagents and to chemical evaluation of Coptidis Rhizoma". J Nat Med. 2011 ;65:262-267.
Chalubinski M et al. "Glucocorticoid-induced immunoglobulin E synthesis by peripheral blood mononuclear cells from allergic and nonallergic subjects". Ann Allergy Asthma Immunol. 2011;107:251-257.
Iwamoto K et al. "Fucoidan suppresses IgE production in peripheral blood mononuclear cells from patients with atopic dermatitis". Arch Dermatol Res. 2011;303:425-431.
Oettgen HC. "Regulation of the IgE isotype switch: new insights on cytokine signals and the functions of epsilon germline transcripts". Curr Opin Immunol. 2000;12:618-623.
Geha RS et al. "The regulation of immunoglobulin E class-switch recombination". Nat Rev Immunol. 2003;3:721-732.
Srivastava KD et al. "Efficacy and immunological actions of FAHF-2 in a murine model of multiple food allergies". Ann Allergy Asthma Immunol. 2012;108:351-358.
Vuddanda PR et al. "Berberine: a potential phytochemical with multispectrum therapeutic activities". Expert Opin Investig Drugs. 2010;19:1297-1307.
Lou T et al. "Berberine inhibits inflammatory response and ameliorates insulin resistance in hepatocytes". Inflammation. 2011 ;34:659-667.
Hamsa TP et al. "Antiangiogenic activity of berberine is mediated through the downregulation of hypoxia-inducible factor-I , VEGF, and proinflammatory mediators". Drug Chem Toxicol. 2012;35:57-70.
Lan T et al. "Berberine attenuates high glucose-induced proliferation and extracellular matrix accumulation in mesangial cells: Involvement of suppression of cell cycle progression and NF-kappaB/AP-1 pathways". Mal Cell Endocrinol. 2014;384:109-116.

(Continued)

*Primary Examiner* — Raymond J Henley, III
(74) *Attorney, Agent, or Firm* — Scully Scott Murphy & Presser

(57) ABSTRACT

The present invention relates to compounds and formulations derived from traditional Chinese medicine for use for the treatment and/or mediation of food allergies, in particular peanut allergies in humans by altering the activity and/or production of IgE.

3 Claims, 46 Drawing Sheets

(56) References Cited

OTHER PUBLICATIONS

Altin J et al. "Understanding the genetic regulation of igE production". Blood Rev. 2010;24:163-169.

Manners GD. "Citrus limonoids: analysis, bioactivity, and biomedical prospects". JAgric Food Chem. 2007;55:8285-8294.

Qu C et al. "Induction of tolerance after establishment of peanut allergy by the food allergy herbal formula-2 is associated with up-regulation of interferon-gamma". Clin Exp Allergy 2007; 37(6):846-55.

Branum AM et al. "Food allergy among children in the United States". Pediatrics. 2009; 124:1549-1555.

Leung DY et al. "Effect of anti-IgE therapy in patients with peanut allergy". N Engl J Med 2003;348:986-993.

Sampson HA et al. "A phase II, randomized, doubleblind, parallelgroup, placebocontrolled oral food challenge trial of Xolair (omalizumab) in peanut allergy". JAllergy Clin Immunol. 2011;127:1309-1310.

Nadeau KC et al. "Rapid oral desensitization in combination with omalizumab therapy in patients with cow's milk allergy". JAllergy Clin Immunol. 2011;127:1622-1624.

Schneider LC et al. "A pilot study of omalizumab to facilitate rapid oral desensitization in high-risk peanut-allergic patients". JAllergy Clin Immunol. 2013; 132:1368-1374.

Srivastava KD et al. "The Chinese herbal medicine formula FAHF-2 completely blocks anaphylactic reactions in a murine model of peanut allergy". JAllergy Clin Immunol. 2005;115:171-178.

Song Y et al. "Food allergy herbal formula 2 protection against peanut anaphylactic reaction is via inhibition of mast cells and basophils". JAllergy Clin Immunol. 2010; 126:1208-1217.

Srivastava K et al. "Efficacy, safety and immunological actions of butanol-extracted Food Allergy Herbal Formula-2 on peanut anaphylaxis". Clin Exp Allergy. 2010;41:582-591.

Patil SP et al. "Clinical safety of Food Allergy Herbal Formula-2 (FAHF-2) and inhibitory effect on basophils from patients with food allergy: Extended phase I study". JAllergy Clin Immunol. 2011, 28; 6:1259-1265.

Wang J et al. "Safety, tolerability, and immunologic effects of a food allergy herbal formula (FAHF-2) in food allergic individuals: a randomized, double-blinded, placebo-controlled, dose escalation phase I study". Ann Allergy Asthma Immunol. 2010;105:75-84.

Jayaprakasam B et al. "Licorice flavonoids inhibit eotaxin-1 secretion by human fetal lung fibroblasts in vitro". JAgric Food Chem. 2009;57:820-825.

Lopez-Exposito I et al. "Chinese herbal extracts of Rubia cordifolia and Dianthus superbus suppress IgE production and prevent peanut-induced anaphylaxis". Chin Med. 2011;6:35:1-10.

Yang N et al. "Glycyrrhiza uralensis flavonoids present in anti-asthma formula, ASHMI, inhibit memory Th2 responses in vitro and in vivo". Phytother Res. 2013;27:1381-1391.

Ehrman TM et al. "Phytochemical databases of Chinese herbal constituents and bioactive plant compounds with known target specificities". J Chem Inf Model. 2007;47:254-263.

Ehrman TM et al. "Phytochemical informatics of traditional Chinese medicine and therapeutic relevance". J Chem Inf Model. 2007;47:2316-2334.

Bacharier LB et al. "Molecular mechanisms of IgE regulation". JAllergy Clin Immunol.2000; 105:S547-S558.

Torgerson TR et al. "Severe food allergy as a variant of IPEX syndrome caused by a deletion in a noncoding region of be FOXP3 gene". Gastroenterology.2007;132:1705-1717.

Vale-Pereira S et al. "FoxP3, GATA-3 and T-bet expression in elderly asthma". Clin Exp Allergy. 2011;41:490-496.

Mantena SK et al. "Berberine, a natural product, induces GI-phase cell cycle arrest and caspase-3-dependent apoptosis in human prostate carcinoma cells". Mal Cancer Ther. 2006;5:296-308.

Chai YS et al. "Inhibition of retinoblastoma mRNA degradation through Poly (A) involved in the neuroprotective effect of berberine against cerebral ischemia". PLoS One.2014;9:1-13.

Roy A et al. "Limonoids: overview of significant bioactive triterpenes distributed in plants kingdom". Biol Pharm Bull. 2006;29:191-201.

The US Food and Drug Administration (FDA), Center for Drug Evaluation and Research. Guidance for Industry Botanical Drug Products. 2004;1-52.

Shang W et al. [Effects of berberine on serum levels of inflammatory factors and inflammatory signaling pathway in obese mice induced by high fat diet]. Zhongguo Zhong Yao Za Zhi. 2010;35:1474-1477, in Chinese together with English Abstract.

\* cited by examiner

Berberine

Limonin
(Obaculactone)

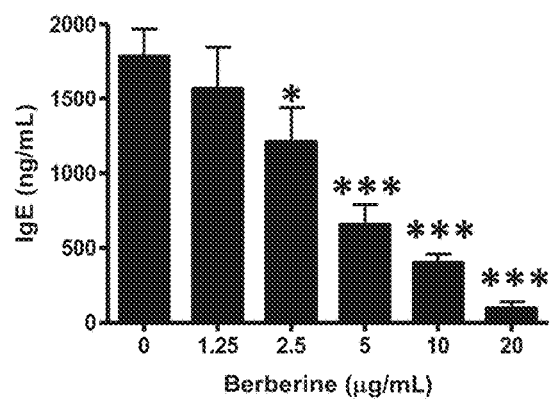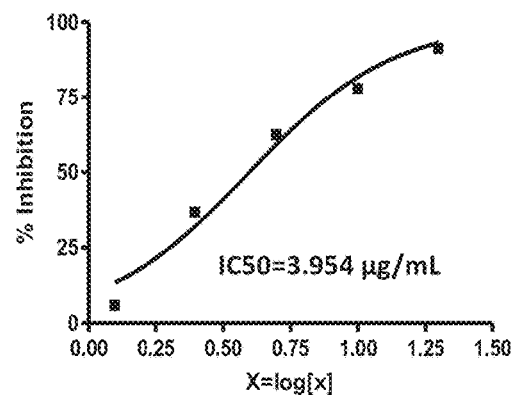
FIG. 3A  FIG. 3B
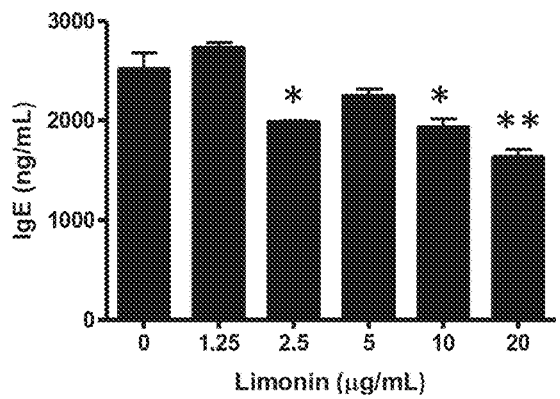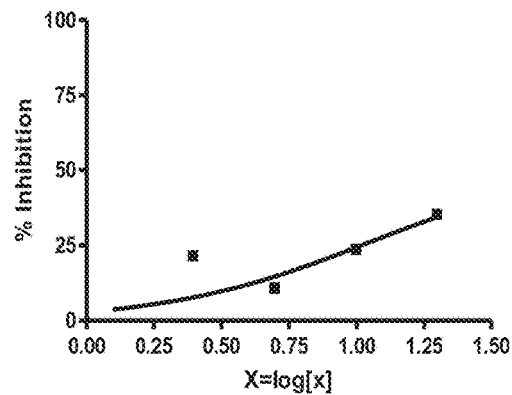
FIG. 3C  FIG. 3D 1,3-Dihydroxyanthraquinone
(Xanthopurpurin)
Molecular weight :240;
Formula:$C_{14}H_8O_4$ Set 1

Set 2

IC 50  2.73ug/ml

IC 50  5.09ug/ml

IC 50 3.88 µg/ml

Berberine

Indigo Naturalis

Indirubin

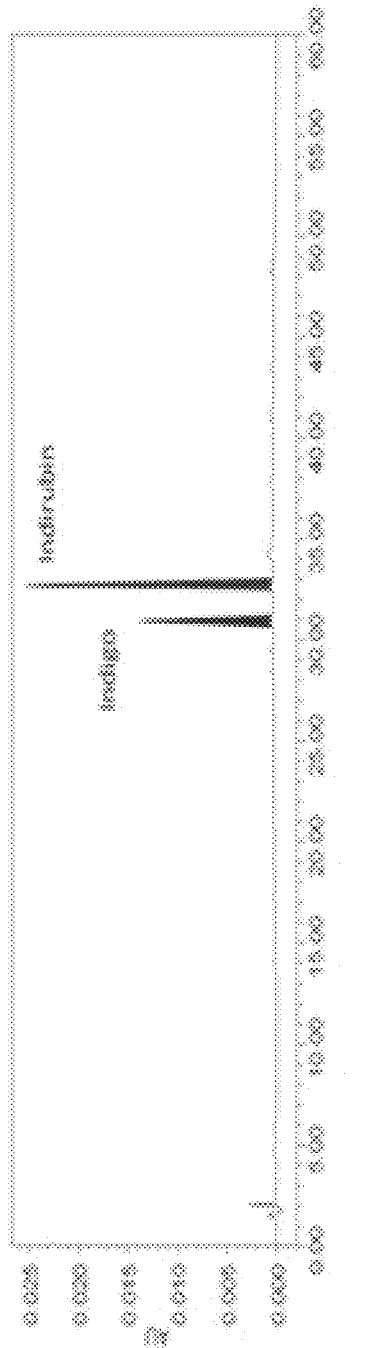
FIG. 24B
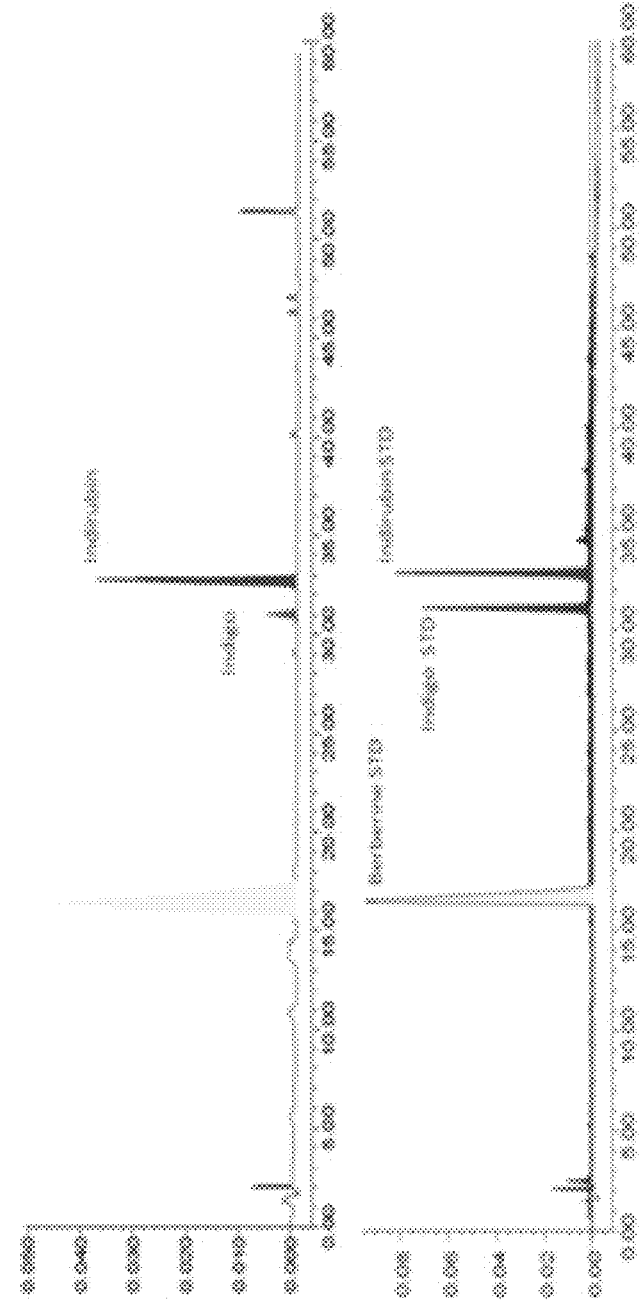
FIG. 24C
FIG. 24D

Purpurin

Alizarin

Arctiin

Arctigenin

SUPPRESSION OF IGE PRODUCTION BY COMPOUNDS DERIVED FROM TRADITIONAL CHINESE MEDICINE

STATEMENT REGARDING FEDERALLY SPONSORED RESEARCH

The research leading to the present invention was supported, in part, by NIH/NCCAM Center for complementary and Alternative Medicine grant #1R01AT001495-01A1 and 2R01 AT001495-05A1, the Food Allergy Initiative and Winston Wolkoff Fund for Integrative Medicine for Allergies and Wellness to Dr. Xiu-Min Li. Julie Wang is supported in part by a grant from NIH NIAID K23 AI083883. This study was also partially supported by a Utah State University faculty startup fund to Jixun Zhan. Accordingly, the U.S. government has certain rights in the invention.

FIELD OF THE INVENTION

The present invention relates to compounds, formulations and methods used to suppress IgE production and their uses for the treatment of food allergies.

BACKGROUND OF THE INVENTION

The prevalence of food allergies has continued to rise, with 8% of children and 4% of adults in the United States now suffering from food allergies. [1] Most food allergies are the result of food protein specific IgE antibody production; exposure to the triggering antigen can lead to potentially life-threatening reactions, including anaphylaxis. Efforts to decrease IgE levels are being explored as a therapeutic approach for food allergies. In an early multi-center trial of the anti-IgE antibody TNX-901, peanut allergic patients who received TNX-901 had a significant decrease in symptoms following peanut challenge as compared to the placebo group. [2] Furthermore, the median threshold of sensitivity to peanut increased from 178 mg peanut protein (the equivalent to one-half of a peanut) to 2.8 grams (almost 9 peanuts). Subsequently, another anti-IgE antibody, omalizumab (Xolair®, Genentech), was investigated in a randomized, double-blind, parallel group, placebo-controlled study for peanut allergy. [3] Although the trial was suspended early due to safety concerns related to 2 anaphylactic reactions during screening oral food challenges performed prior to administration of any study drug, 14 subjects completed the post-therapy (24-week) oral food challenge. Based on the limited data, there appeared to be a greater shift in peanut tolerability in subjects treated with omalizumab as compared to placebo that was accompanied by a reduction of serum peanut specific IgE. [3] In 2011, Nadeau et al. [4] performed a phase I study using anti-IgE in conjunction with oral immunotherapy in 11 milk allergic children. Nine of these subjects were successfully desensitized within 7-11 weeks. While co-treatment with anti-IgE allowed for rapid desensitization, adverse reactions still occurred in all subjects, and 3 required epinephrine injections. Recently, Schneider et al. 5 performed a pilot study using omalizumab to facilitate rapid oral desensitization in peanut-allergic patients with high levels of IgE. All thirteen subjects tolerated a cumulative dose of 992 mg peanut flour on the first day. Twelve of thirteen subjects tolerated 4000 mg of peanut flour after 7-12 weeks. Although the safety data was improved as compared to previous studies, 50% experienced grade 1 or grade 2 reactions, and 2 patients required epinephrine. Omalizumab therapy is expensive, not indicated for subjects with high total serum IgE levels, associated with risk of anaphylactoid reactions, and must be administered in a physician's office. Therefore, it is time consuming and not practical for many patients. Furthermore, omalizumab binds circulating IgE, but does not directly suppress B cell IgE production. An alternative approach that inhibits IgE production would meet an unmet need in the art.

SUMMARY OF THE INVENTION

As specified in the Background Section, above, there is a great need in the art to develop new therapeutic tools for treating food allergies and other diseases and/or conditions mediated by IgE. The present invention addresses this and other needs by providing novel compounds, formulations and methods which are useful in suppressing IgE production and therefore are useful in treating and/or mediating food allergies and other diseases in subjects.

In one embodiment, the invention provides an isolated compound, wherein said compound is capable of suppressing IgE production. In one specific embodiment, the compound is berberine.

In one embodiment, the invention provides an isolated compound, wherein said compound is capable of suppressing IgE production. In one specific embodiment, the compound is limonin.

In one embodiment, the invention provides an isolated compound, wherein said compound is capable of suppressing IgE production. In one specific embodiment, the compound is 1,3-Dihydroxyanthraquinone.

The invention also provides pharmaceutical compositions comprising one or more compounds of the invention and a pharmaceutically acceptable carrier or excipient. In one specific embodiment, the composition comprises one or more compounds isolated from *Phellodendri chinensis*. In another specific embodiment, the composition comprises berberine. In yet another specific embodiment, the composition comprises limonin. In a preferred embodiment the composition comprises a topical cream.

The invention also provides pharmaceutical compositions comprising one or more compounds of the invention and a pharmaceutically acceptable carrier or excipient. In one specific embodiment, the composition comprises one or more compounds isolated from *Rubia cordifolia*. In another specific embodiment, the composition comprises 1,3-Dihydroxyanthraquinone. In a preferred embodiment the composition comprises a topical cream.

In conjunction with the compounds of the present invention, the invention also provides a method for inhibiting IgE production by a cell, which method comprises administering to the cell one or more compounds of the invention or a composition comprising such one or more compound(s). In one specific embodiment, the cell to which the composition is administered is a B lymphocyte.

In a further embodiment, the invention provides a method for treating and/or mediating a food allergy in a subject in need thereof, which method comprises administering to the subject a therapeutically effective amount of one or more compounds of the invention or a composition comprising such one or more compounds(s). Non-limiting examples of the food allergies treatable by the method of the invention include peanut allergy, tree nut allergy, egg allergy, milk allergy, wheat allergy, soy allergy and many other food allergies as well as other allergic conditions such as allergic rhinitis, eczema and asthma. In a preferred embodiment, the subject is human.

BRIEF DESCRIPTION OF THE DRAWINGS

The patent application file contains at least one drawing executed in color.

FIGS. 2A and 2B show mass spectra of DMF-C1 (berberine) and DMF-A1 (limonin), respectively. FIGS. 2C and 2D show the chemical structures of berberine and limonin, respectively.

FIGS. 3A-3D show dose-dependent berberine and limonin inhibition of IgE production by U266 cells. FIG. 3A shows the inhibitory effect of berberine on IgE production by U266 cells. FIG. 3B shows the percentage of IgE inhibition vs. log [x] berberine concentration curve. FIG. 3C shows the cell viability of cultured U266 cells with or without berberine. FIG. 3D shows the inhibitory effect of limonin on IgE production by U266 cells. FIG. 3E shows the percentage of IgE inhibition vs. log [x] limonin concentration curve. FIG. 3F shows the cell viability of cultured U266 cells with or without limonin. *, $p<0.05$; , $p<0.01$; *, $p<0.001$ ($n \geq 3$).

FIG. 4A shows the dose dependent inhibitory effect of berberine on IgE production by PBMCs. PBMCs from pediatric subjects with food allergy were isolated. Cells were co-stimulated with human rIL-4 (100 ng/mL) and anti-CD40 mAb (1 µg/mL) in the presence or absence of different concentrations of berberine as indicated, for 10 days. IgE levels in supernatants were determined by ELISA. FIG. 4B shows the cell viability of human PBMC at different concentrations of berberine. , $p<0.005$; *, $p<0.001$ ($n=6$).

FIG. 6A shows a representative In-Cell Western experiment with 700 nm and 800 nm channels detecting of p-IκBα and β-actin, respectively. FIG. 6B shows the relative expression levels of p-IκBα measured by In-Cell Western ($n=6$). *, $p<0.05$; **, $p<0.005$.

FIG. 7A shows relative STAT3 expression levels in response to berberine treatment. FIG. 7B shows relative T-bet expression levels in response to berberine treatment. FIG. 7C shows relative IFN-γ expression levels in response to berberine treatment. FIG. 7D shows relative Foxp3 expression levels in response to berberine treatment. FIG. 7E shows relative GATA-3 expression levels in response to berberine treatment. FIG. 7F relative IL-10 expression levels in response to berberine treatment. FIG. 7G shows relative IL-5 expression levels in response to berberine treatment. *, $p<0.05$; , $p<0.01$; *, $p<0.001$ ($n=7$).

FIGS. 22A and 22B show the levels of IL4 in spleen and MLN, respectively. FIGS. 22C and 22D show the levels of IL10 in spleen and MLN, respectively. FIGS. 22E and 22F show the levels of IFN-r in spleen and MLN, respectively. SPC (splenocytes) and MLN (mesenteric lymph node) cultures were collected immediately after evaluation of anaphylactic reactions following the final challenge. Cell suspensions were cultured in complete culture medium in the presence of CPE (Crude Peanut Extract), Con A, or Medium alone. Supernatants were collected 72 hours later, and IL-4, IL-10, IFN-r were determined by ELISA. Data are shown as mean±SEM of cultures measured in duplicate experiments (n=5). *P<0.05 vs. sham.

FIG. 23D presents the cell viability of berberine and Indigo naturalis treated U266 cells.

FIG. 24B presents the HPLC fingerprint of indigo and indirubin. FIG. 24C shows the HPLC fingerprint of Cream 3B. FIG. 24D shows the HPLC fingerprints overlay of berberine, indigo and indirubin standards individually.

FIG. 25A shows the inhibitory effect of FAHF-2 on IgE production by U266 cells. FIG. 25B shows the inhibitory effect of B-FAHF-2 on IgE production by U266 cells. U266 cells (2×105 cells/mL) were cultured with FAHF-2 and B-FAHF-2 at equivalent concentrations as indicated for 6 days. The supernatants were harvested and IgE levels were measured by ELISA. Results were expressed as the mean±S.E. *, p<0.05; ***, p<0.001 (n≥3).

FIG. 36A shows the inhibitory effect of purpurin and FIG. 36B shows the inhibitory effect of alizarin from *Rubia cordifolia* L on IgE production by U266 cells. FIG. 36C shows the inhibition percentage of purpurin and FIG. 36D shows the inhibition percentage of alizarin on IgE production by U266 cells. FIG. 36E shows the inhibition effect of arctiin and arctigenin from *Arctium lappa* L. on IgE production by U266 cells. U266 cells (2×10$^5$ cells/mL) were cultured with each compound at equivalent concentrations as indicated for 6 days. The supernatants were harvested and IgE levels were measured by ELISA. Results were expressed as the mean±S.E. *, p<0.05; **, p<0.01 (n≥3).

FIG. 37A shows the in vivo experimental protocol. FIG. 37B shows the peanut specific-IgE level in the serum of peanut-allergic mice. FIG. 37C shows peanut-induced anaphylactic symptoms score. FIG. 37D shows the core body temperatures during challenge. Body temperatures were measured 30 minutes after completion of oral challenge. FIG. 37E shows the histamine level in plasma after completion of challenge. *, p<0.05; , p<0.01 (n≥3); *, p<0.001.

DETAILED DESCRIPTION OF THE INVENTION

Figure 1:
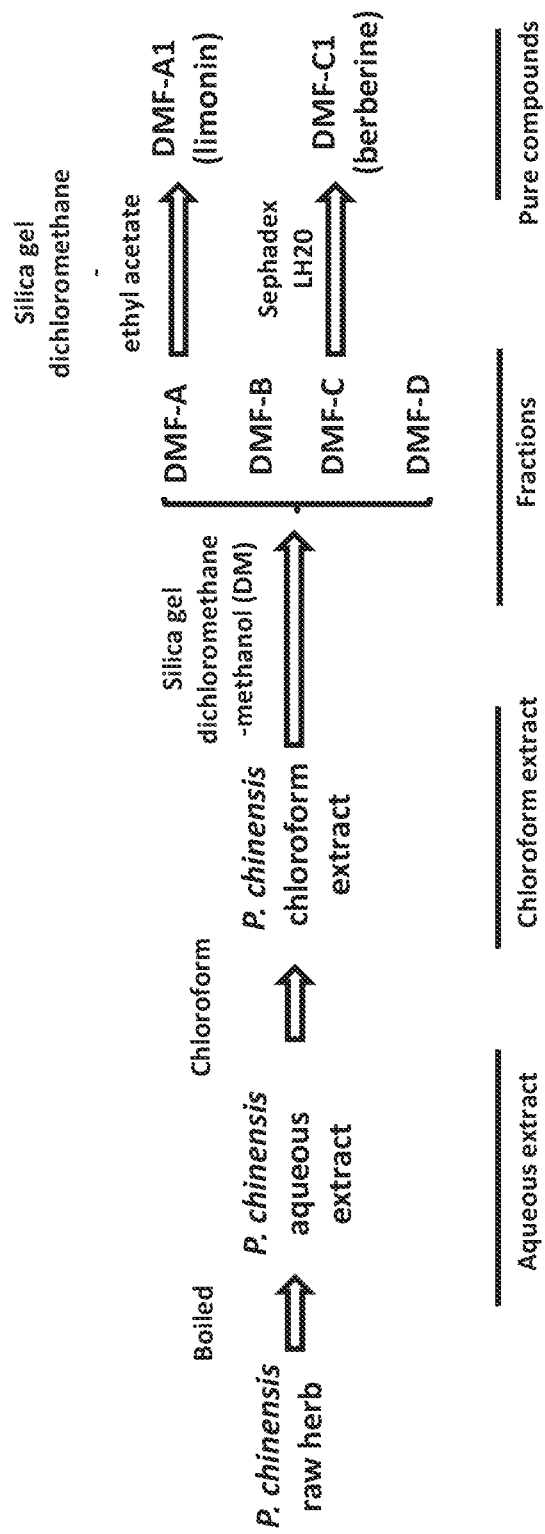
FIG. 1 shows a flow chart of isolation and purification of *P. chinensis* compounds.

The present invention is based on the identification of certain natural products and isolates therefrom that have the capability to alter the production of IgE. The present inventors identified *Phellodendri chinensis* and *Rubia cordifolia* and certain compounds found therein as effective in regulating the production of IgE. In particular the compounds berberine and limonin from *P. chinensis* and the compound 1,3-Dihydroxyanthraquinone from *R. cordifolia*. Various experiments described in further detail below established the importance of berberine, limonin and 1,3-Dihydroxyanthraquinone in regulating IgE production. As described in more detail below, berberine, limonin and 1,3-Dihydroxyanthraquinone were selected for further characterization and shown to reduce production of IgE in various experimental protocols. Taken together the data demonstrate the therapeutic potential of berberine, limonin, and 1,3-Dihydroxyanthraquinone to alter the production of IgE and mediate and/or prevent the deleterious effects of food allergies, namely peanut allergy tree nut allergy, egg allergy, milk allergy, wheat allergy, soy allergy and many other food allergies, as well as other allergic conditions such as allergic rhinitis, eczema and asthma.

The present invention provides novel methods for treating and/or mediating food allergies through the administration berberine and/or limonin and/or 1,3-Dihydroxyanthraquinone.

Definitions

In the context of the present invention insofar as it relates to any of the disease conditions recited herein, the terms "treat", "treatment", and the like mean:
(1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or
(2) inhibiting the state, disorder or condition, i.e., arresting, reducing or delaying the development of the disease or a relapse thereof (in case of maintenance treatment) or at least one clinical or sub-clinical symptom thereof; or
(3) relieving the disease, i.e., causing regression of the state, disorder or condition or at least one of its clinical or sub-clinical symptoms.

As used herein the term "therapeutically effective" applied to dose or amount refers to that quantity of a compound (e.g., isolated compound from *Phellodendri chinensis*) or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a disease specified above. Note that when a combination of active ingredients is administered (e.g., berberine and limonin), the effective amount of the combination may or may not include amounts of each ingredient that would have been effective if administered individually. Therapeutically effective dosages according to the present invention can be determined stepwise by combinations of approaches such as, e.g., (i) characterization in cell cultures using IgE levels as a readout followed by (ii) characterization in animal studies using IgE levels as a readout, followed by (iii) characterization in human trials using plasma IgE levels and/or disease symptoms relief as a readout.

The phrase "pharmaceutically acceptable", as used in connection with the compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "subject" means any animal, including mammals and, in particular, humans.

As used in this specification and the appended claims, the singular forms "a," "an," and "the" include plural references unless the context clearly dictates otherwise.

In accordance with the present invention, there may be employed conventional pharmacology, medicinal chemistry, molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al.

eds., Current Protocols in Molecular Biology, John Wiley and Sons, Inc. 1994; among others.

Pharmaceutical Compositions of the Invention

For administration to human and animal patients, compounds and combinations thereof, of the present invention can be formulated in pharmaceutical compositions in combination with one or more pharmaceutically acceptable carriers and/or excipients such as, e.g., lubricants, diluents, flavorants, colorants, buffers, and disintegrants. Suitable pharmaceutically acceptable carriers include any and all conventional solvents (such as, e.g., water, physiological solution, dextrose, glycerol, ethanol, and the like, as well as combinations thereof), wetting agents, emulgators, buffers, conservants, dispersion media, fillers, solid carriers, aqueous solutions, coatings, antibacterial and antifungal agents, isotonic and absorption delaying agents, as well as other well-known agents which enhance the shelf life or effectiveness of one or more of the active components of the composition. Examples of such useful substances can be found in "Remington's Pharmaceutical Sciences" by E. W. Martin. Except insofar as any conventional media or agent is incompatible with the active ingredient, use thereof in compositions of the present invention is contemplated. The term "pharmaceutically acceptable" refers to a carrier or excipient that does not cause an allergic reaction or other untoward effect in patients to whom it is administered.

The pharmaceutical compositions of the invention can be produced in useful dosage units for administration by various routes including, among others, topical, oral, subcutaneous, intravenous, and intranasal administration.

The pharmaceutical compositions of the invention can also include other biologically active substances in combination with the formulations, individual constituents of the formulations and/or isolates thereof of the invention. Such additional biologically active substances can be also formulated as separate compositions and can be administered simultaneously or sequentially with the formulations, individual constituents of the formulations and/or isolates thereof of the invention. Non-limiting examples of useful biologically active substances include statins, niacin, bile-acid resins, fibric acid derivatives, cholesterol absorption inhibitors, and other lipid-lowering drugs.

In a preferred embodiment, the pharmaceutical composition is a topical cream containing one or more compounds of the present invention and inactive ingredients. In one embodiment the cream is a semi-solid preparation, hydrophilic cream. The emulsion type is oil-in-water, containing berberine, a penetration enhancer, water and emulsifiers. The cream is intended for application to the skin of the subject for therapeutic purposes.

Administration

With the aid of present disclosure, those of skill in the art should be able to derive suitable dosages and schedules of administration for any of a number of suitable compositions that contain the compounds and formulations of the invention. Thus, pharmaceutical compositions within the scope of the present invention include compositions where the active ingredient(s) is contained in an effective amount to decrease IgE production and/or to treat a food allergy.

The formulation and dose for therapeutic administration of the compounds and formulations of the invention will depend on the severity of the disease condition being treated, whether other drugs are being administered, whether other actions are taken, the weight, age, and sex of the subject, and other criteria. The skilled medical practitioner will be able to select the appropriate formulation and dose in view of these criteria and based on the results of published clinical trials. The dosage and administration regimen can be further adjusted for an individual patient by monitoring the level of IgE.

The optimal therapeutically effective amount of compounds and formulations or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

As disclosed herein, the concentrations of the formulations administered in the present invention are both therapeutically effective and pharmaceutically acceptable. The compounds and formulations of the present invention are preferably used in vivo at the following dose ranges: for the individual compounds, preferred dosage ranges between about 0.1-50 mg/kg; for the creams of the invention, preferred dosage ranges from about 75-150 mg/kg of effective compound.

Following methodologies which are well-established in the art, effective doses and toxicity of the formulations, individual constituents of the formulations and/or isolates thereof and compositions of the present invention, which performed well in in vitro tests, can be determined in studies using small animal models (e.g., mice, rats) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the compounds and formulations in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

The compounds and compositions of the invention can be formulated for parenteral, oral, topical, transdermal, transmucosal, intranasal, buccal administration, or by any other standard route of administration. Parenteral administration includes, among others, intravenous (i.v.), subcutaneous (s.c.), intraperitoneal (i.p.), intramuscular (i.m.), subdermal (s.d.), intradermal (i.d.), intra-articular, intra-synovial, intra-arteriole, intraventricular, intrathecal, intrasternal, intrahepatic, intralesional, or intracranial administration, by direct injection, via, for example, bolus injection, continuous infusion. A preferred route of administration according to the present invention will depend primarily on the indication being treated and includes, among others, topical, oral, subcutaneous, intravenous, and intranasal administration.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use. Suitable formulations for parenteral administration may contain substances which increase viscosity, for example, sodium carboxymethyl cellulose, sorbitol, and/or dextran. Optionally, the formulation may also contain stabilizers.

For oral administration, the compositions of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Delivery

Compositions of the present invention can be delivered systemically or locally. If targeted delivery to a particular cell or tissue is desirable, compounds and formulations may be coupled to conjugates or delivery vectors containing antibodies to cell- or tissue-specific antigens can be used.

Therapeutic Methods of the Invention

In conjunction with the novel compounds and compositions, provided herein are methods of treatment using such compounds and formulations. Specifically, the invention provides a method for treating a disease in a subject in need thereof, which method comprises administering to the subject a therapeutically effective amount of one or more compounds and compositions of the invention or a composition comprising such one or more compounds and compositions. Non-limiting examples of the diseases treatable by the method of the invention include food allergies such as peanut allergy tree nut allergy, egg allergy, milk allergy, wheat allergy, soy allergy and many other food allergies, as well as other allergic conditions such as allergic rhinitis, eczema and asthma.

In a preferred embodiment, the subject is human.

Turning now to the figures:

FIG. 1 shows a flow chart of isolation and purification of *P. chinensis* compounds. 200 g of a dried *P. chinensis* aqueous extract dissolved in 4 L of distilled water was extracted with an equal volume of chloroform. Compounds in resulting chloroform extract were then separated on the basis of their polarity using silica gel (Merck 230-400mesh, Sigma, Germany) and sequentially eluted using dichloromethane-methanol (DM) mixtures at ratios of 49:1, 19:1, 9:1, and 1:1. 4 major sub-fractions were collected and designated DMF-A, B, C, and D. DMF-A was further separated using silica gel chromatography with a mobile phase of dichloromethane-ethyl acetate mixture at 19:1, 9:1, and 5:1 ratios. One compound was re-crystallized from 19:1 dichloromethane-ethyl acetate eluent and named DMF-A1. DMF-C was further separated/purified using a Sephadex LH20 column with methanol as the solvent, yielding a pure compound named DMF-C1 (232 mg).

Figure 2A:
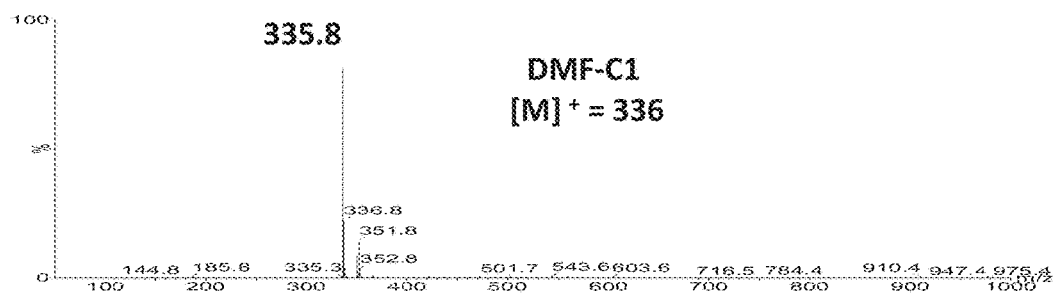
FIGS. 2A-2D show compounds isolated from *P. chinensis*.
Figure 2B:
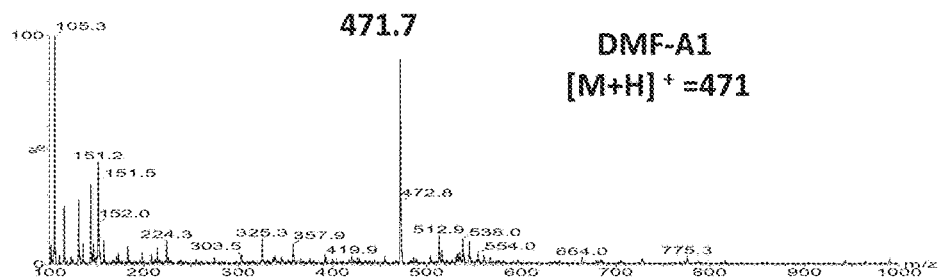
Figure 2C:
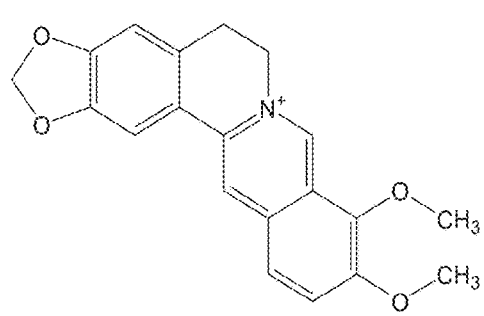
Figure 2D:
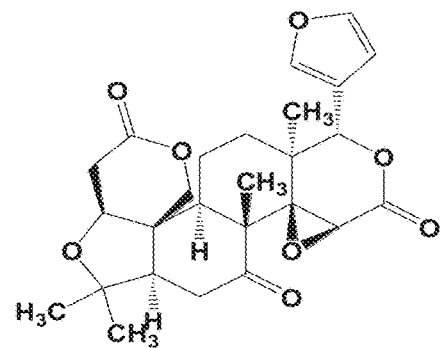

FIG. 2A-2D shows compounds isolated from *P. chinensis*. FIGS. 2A and 2B. Mass spectra of DMF-C1 (berberine) (2A) and DMF-A1 (limonin) (2B). FIGS. 2C and 2D. Chemical structures of berberine (2C) and limonin (2D).

FIGS. 3A-3D shows dose-dependent berberine and limonin inhibition of IgE production by U266 cells. FIG. 3A. berberine inhibition of IgE production by U266 cells. FIG. 3B. Percentage of IgE inhibition vs. log [x] berberine concentration curve. FIG. 3C. Limonin inhibition of IgE production by U266 cells. FIG. 3D. Percentage of IgE inhibition vs. log [x] limonin concentration curve. *, $p<0.05$; , $p<0.01$; *, $p<0.001$ ($n \geq 3$).

The bioactivities were analyzed in vitro on U266 cells in the presence of berberine or limonin at different concentrations. As shown in FIG. 3A, berberine inhibited IgE production in a dose-dependent manner, reaching 94.6% inhibition at 20 µg/mL. The IC50 value was 3.95 µg/mL (FIG. 3B). Limonin showed mild reduction of IgE production by U266 cells. The greatest inhibitory effect of limonin was 35.1%, observed at a concentration of 20 µg/mL (p<0.01) (FIG. 3C). Unlike berberine, no dose dependent effect was observed for limonin. Cell viability assays showed no toxicity at any concentration tested (FIG. 3IC-D).

Figure 4A:
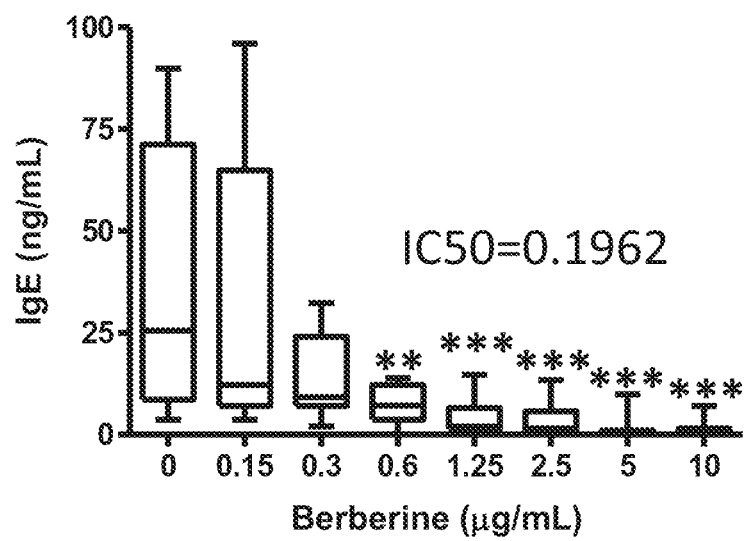
FIGS. 4A and 4B show the dose-dependent inhibitory effect of berberine on IgE production by human PBMC.
Figure 4B:
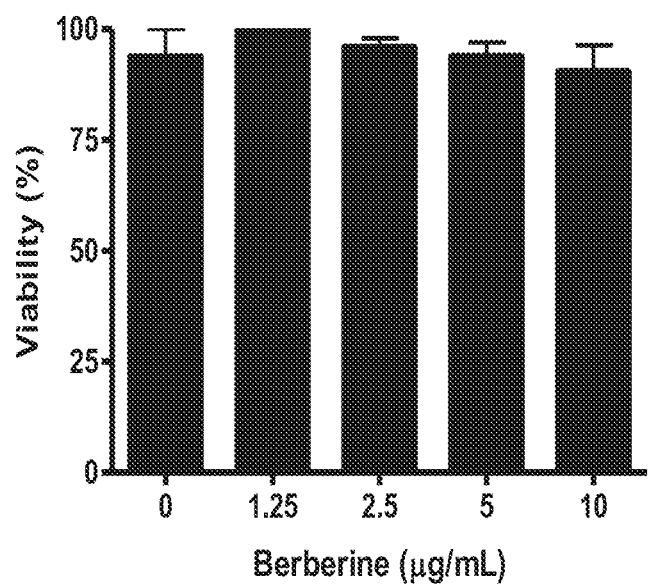

FIGS. 4A-4B shows the dose-dependent inhibitory effect of berberine on IgE production by human PBMC. FIG. 4A. Concentration dependent berberine inhibition of PBMC IgE production. Isolated PBMCs from food allergic patients were co-stimulated with human rIL-4 (100 ng/mL) and anti-CD40 mAb (1 µg/mL) in the presence or absence of different concentrations of berberine as indicated for 10 days. IgE levels in supernatants were determined by ELISA. FIG. 4B. Cell viability of human PBMC cultured with the same concentrations of berberine. , p<0.005; *, p<0.001 (n=6).

Figure 33:
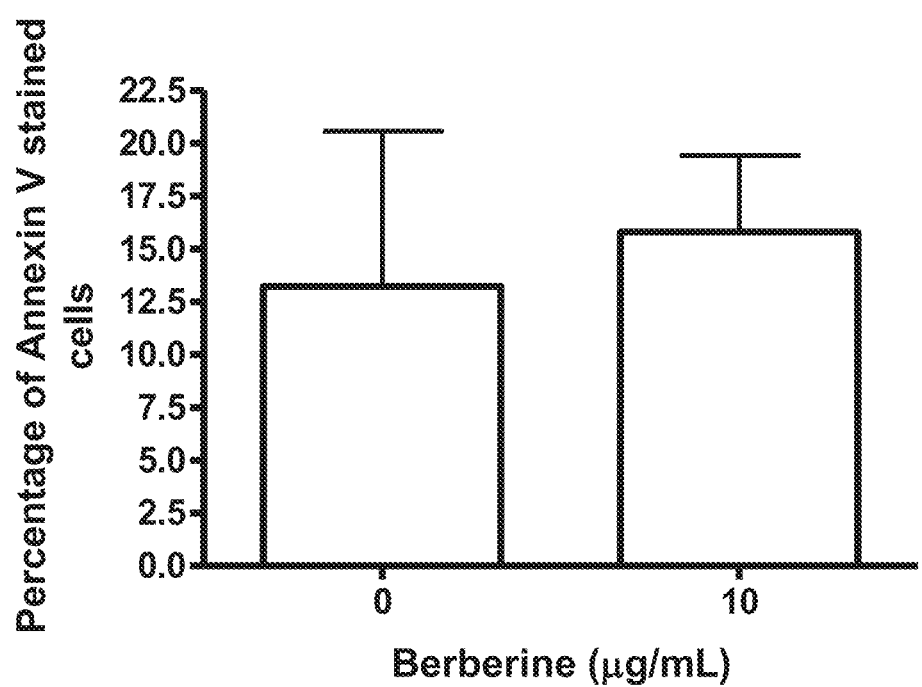
FIG. 33. Percentage of Annexin V stained B cells in Human PBMCs.

To further examine the effect of berberine and limonin on IgE production, PBMCs from food allergic individuals were used. To optimize culture conditions, we tested different concentrations of anti-CD40 antibodies (0.1 and 1 µg/mL) and rIL-4 (10 and 100 ng/mL) and culture durations (10 and 14 days). The results showed that human PBMCs generated the highest concentration of IgE when co-incubated with 100 ng/mL rIL-4 and 1 µg/mL anti-CD40 mAb for 10 days. Using these parameters, we assessed the inhibitory effects of berberine and limonin. Berberine completely inhibited the IgE production by human PBMCs at 20 µg/mL, whereas limonin produced 33.9% inhibition at the same concentration (not shown). Dose dependent effects of berberine on IgE production by PBMCs was further investigated (FIG. 4A). Significant inhibition starting at 0.62 µg/mL (80.67±9.24% inhibition percentage) was observed. IC50 value was calculated to be 0.20 µg/mL. Cell viability was not compromised at any dose of berberine tested (FIG. 4B). We assessed potential apoptosis using flow cytometry and annexin V. After 2 days incubation with 10 µg/ml of berberine, PBMCs were incubated with CD19 antibody and stained with annexin V. The result showed about 16% stained B cells in both berberine treated and untreated cells. No significant difference was observed. We have included these data in FIG. 33.

Figure 5:
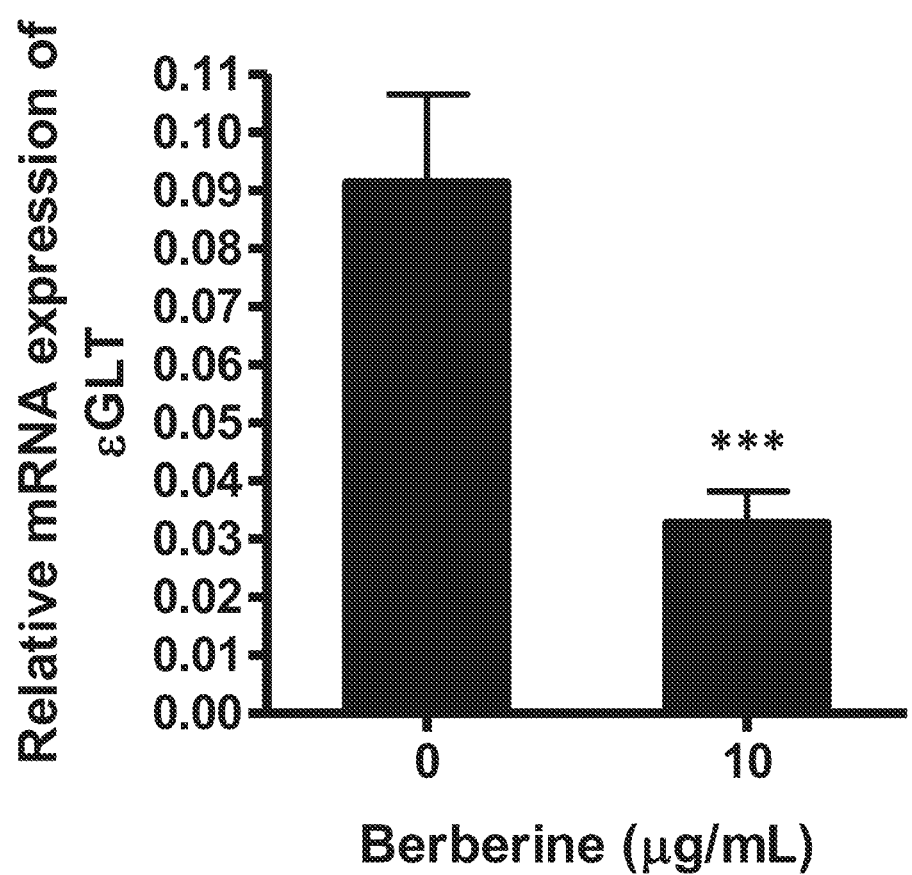
FIG. 5 illustrates that berberine suppresses εGLT transcripts expression by PBMCs from food allergic patients. PBMCs ($1.5 \times 10^6$ cells/mL) were isolated from pediatric subjects as in FIG. 4A and co-stimulated with human rIL-4 (100 ng/mL) and anti-CD40 mAb (1 g/mL) in the presence of berberine at 10 µg/mL for 4 days. The relative expression level of εGLT was determined by comparing with GAPDH mRNA expression ***$p<0.001$ ($n=7$).

FIG. 5. Berberine suppresses εGLT transcripts expression by PBMCs from food allergic patients. PBMCs isolated from food allergic patients were co-stimulated with human IL-4 (1 µg/mL) anti-CD40 mAb (1 µg/mL) in the presence of berberine at 10 µg/mL for 4 days. RNA was extracted using Trizol. The relative expression levels of εGLT were determined by comparison with GAPDH mRNA expression. ***, p<0.001 (n=7).

Epsilon germline transcription is an important step for IgE isotype switching. To test whether the mechanism of the inhibition effect of berberine on IgE production is through regulation of the epsilon germline, we analyzed the mRNA expression of åGLT by RT-PCR. The mRNA expression of GLT was detected in 7 patients' PBMCs. RT-PCR results demonstrated that the relative mRNA expression of åGLT was significantly inhibited when co-incubated with berberine (FIG. 5) at a concentration of 10 µg/mL as compared to untreated cultures (p<0.001).

Figure 6A:
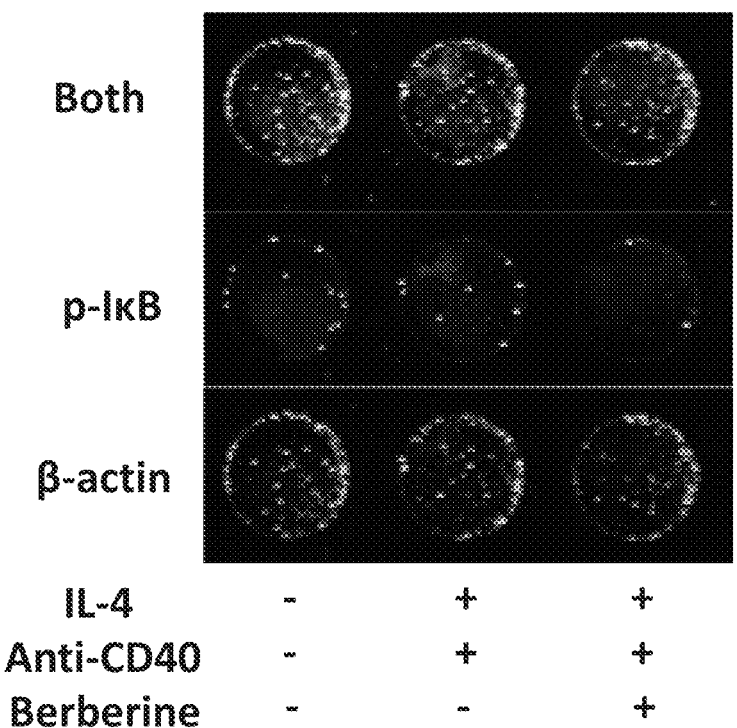
FIGS. 6A and 6B illustrate that berberine suppresses phosphorylated-IκBα expression by PBMCs from food allergic patients using In-Cell Western Blotting.
Figure 6B:
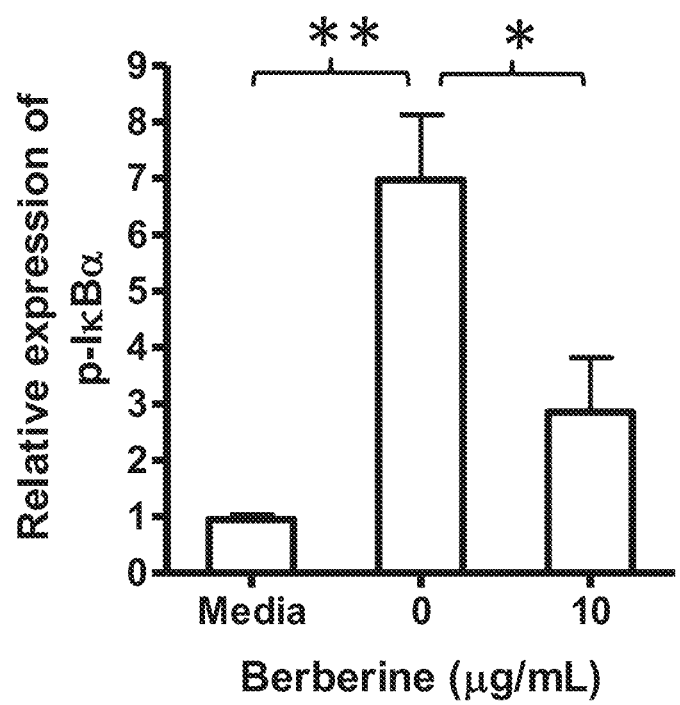

FIGS. 6A-6B. Berberine suppresses phosphorylated-IκBα expression by PBMCs from food allergic patients. PBMCs were isolated and cultured as described. In-Cell Western was performed as described in the Methods. FIG. 6A. Representative In-Cell Western with 700 nm and 800 nm channels detecting of p-IκBα and β-actin. FIG. 6B. Relative expression of p-IκBα measured by In-Cell Western (n=6). *, p<0.05; **, p<0.005.

NF-êB signaling pathways are involved in B cell activation. It is possible that the NF-êB signaling pathway is involved in upstream mechanisms underlying berberine inhibition of IgE synthesis. NF-êB is inactive when reacted with the inhibitory IêB protein. Phosphorylation of IêB results the exposure of the nuclear localization signals on NF-êB. This eventually leads to the translocation of NF-êB to the nucleus, and activation of the Iå promoter, and enhance the êGLT transcripts. We therefore determined phosphorylated IêBá levels in berberine treated human PBMCs. Phosphorylated IêBá levels were significantly increased after stimulation with IL-4 and anti-CD40 antibody (p<0.005). Berberine treatment at 10 µg/mL significantly suppressed phosphorylated IêBá levels compared with the non-treated cells (p<0.05) (FIG. 6B).

FIGS. 7A-7G. Berberine enhances STAT3 and T-bet transcript expression by PBMCs from food allergic patients. PBMCs were isolated and cultured as described in FIGS. 6A and 6B. RNA was extracted using Trizol. The expression of STAT3 (FIG. 7A), T-bet (FIG. 7B), IFN-γ (FIG. 7C), Foxp3 (FIG. 7D), GATA-3 (FIG. 7E), IL-10 (FIG. 7F), and IL-5 (FIG. 7G) were determined by comparison with GAPDH mRNA expression. *, p<0.05; , p<0.01; *, p<0.001 (n=7).

Figure 7A:
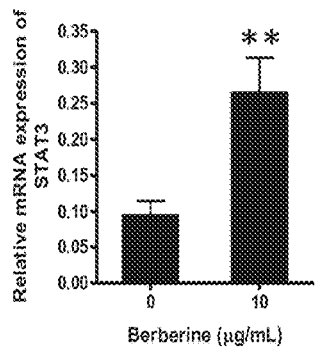
FIGS. 7A-7G show that berberine enhances STAT3 and T-bet transcript expression by PBMCs from food allergic patients. PBMCs were isolated and culture as described in FIGS. 6A and 6B. RNA was extracted using Trizol. The gene expression levels were normalized to GAPDH.
Figure 7B:
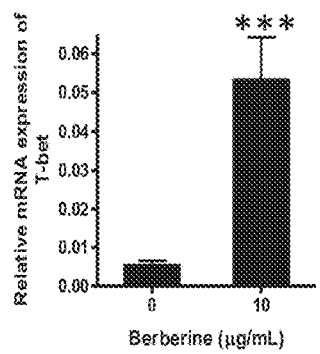
Figure 7C:
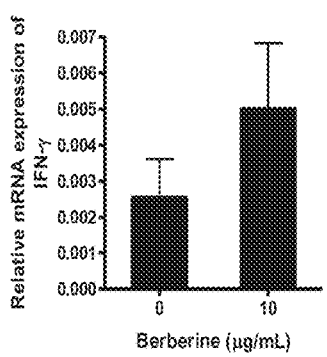
Figure 7D:
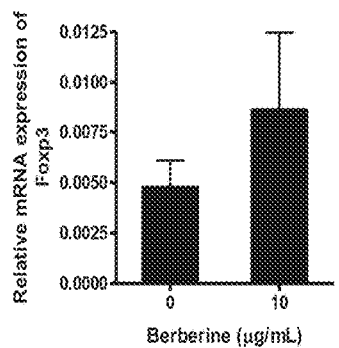
Figure 7E:
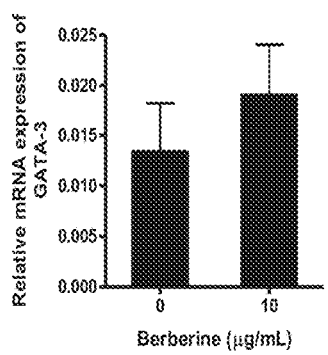
Figure 7F:
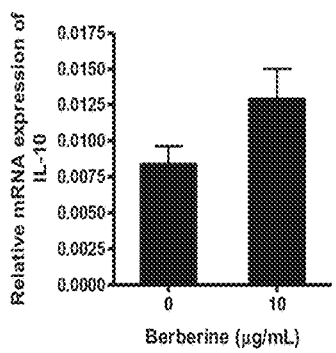
Figure 7G:
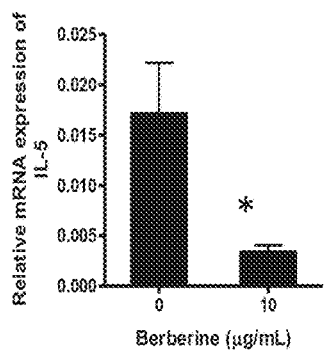

In order to further explore the mechanism of berberine's effects on PBMCs, we performed real-time PCR to analyze gene expression levels of STAT3, T-bet, IFN-ã, Foxp3, GATA-3, IL-10, and IL-5 (FIG. 7A through FIG. 7G). 10 µg/mL berberine treated cells significantly increased mRNA expression of T-bet (p<0.001) (FIG. 7B) and STAT-3 (p<0.005) (FIG. 7A) in stimulated PBMCs. The mRNA levels of IFN-ã, Foxp3, IL-10 showed a trend of increase (FIG. 7C-7D-7E). No significant change on GATA-3 expression was observed. The mRNA level of IL-5, were significantly decreased (p<0.05) (FIG. 7G).

Figure 8A:
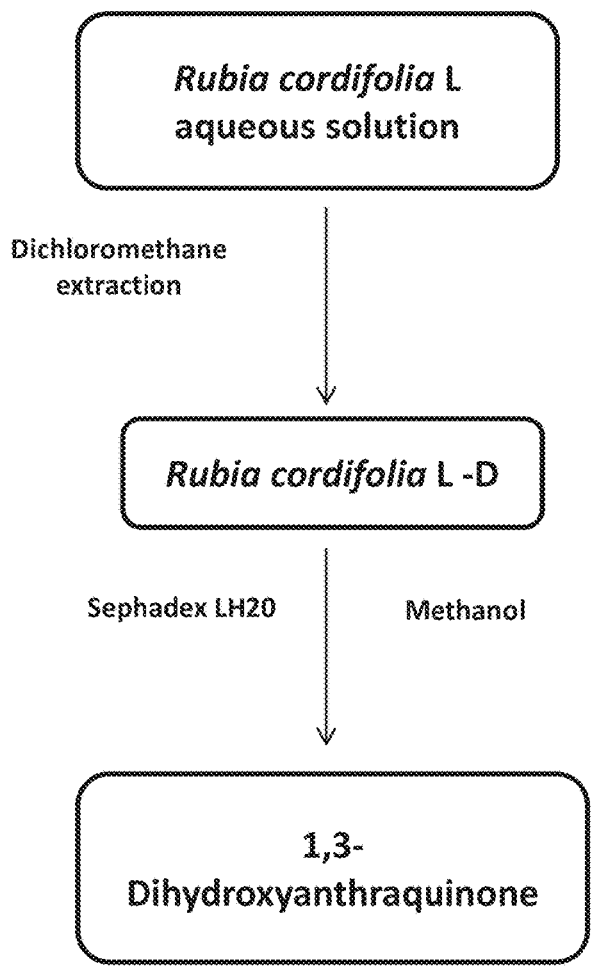
FIG. 8A shows a flow chart of isolation and purification of *Rubia cordifolia* L compound.
Figure 8B:
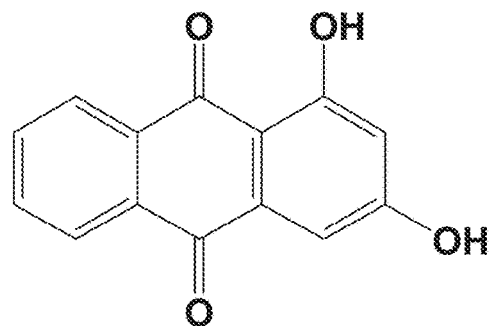
FIG. 8B shows the chemical structure, molecular weight and molecular formula of 1,3-Dihydroxyanthraquinone.

FIG. 8A shows a flow chart of isolation and purification of *Rubia cordifolia* L compound 1,3-Dihydroxyanthraquinone. *Rubia cordifolia* L. fractionation method (FIG. 8A) and chemical structure of isolated compounds (FIG. 8B). An aqueous extract of *Rubia cordifolia* L. was extracted with an equal volume of dichloromethane. The dichloromethane extract was separated on a column using Sephadex LH20 resin, eluted with methanol. One compound was collected and its chemical properties were identified (FIG. 8B).

Figure 9:
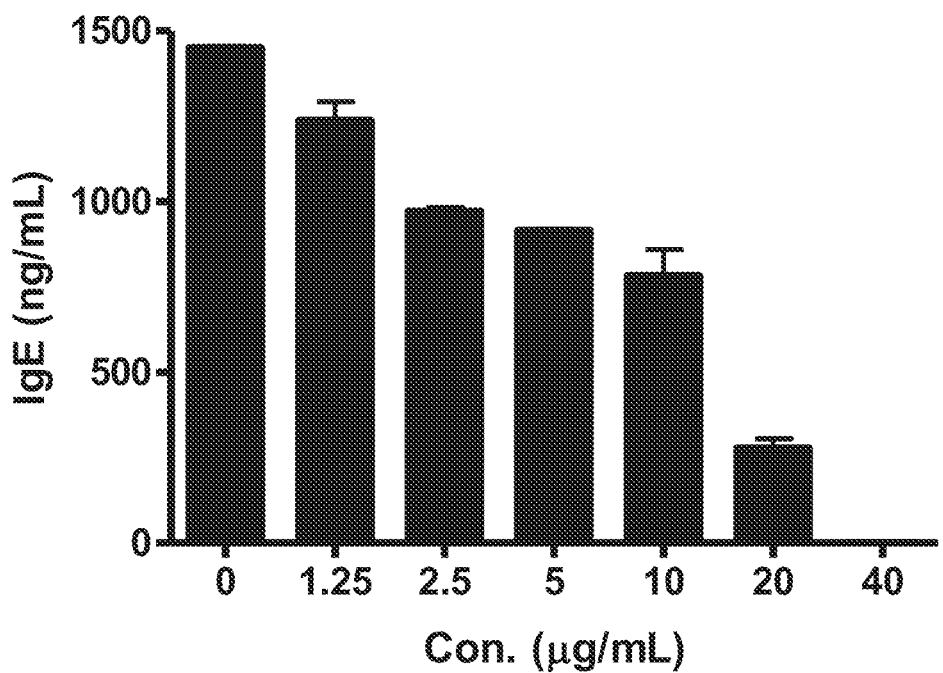
FIG. 9 shows the 1,3-Dihydroxyanthraquinone dose-dependent inhibition of IgE production by U266 cells.

FIG. 9 shows 1,3-Dihydroxyanthraquinone dose-dependent inhibition of IgE production by U266 cells.

Figure 10:
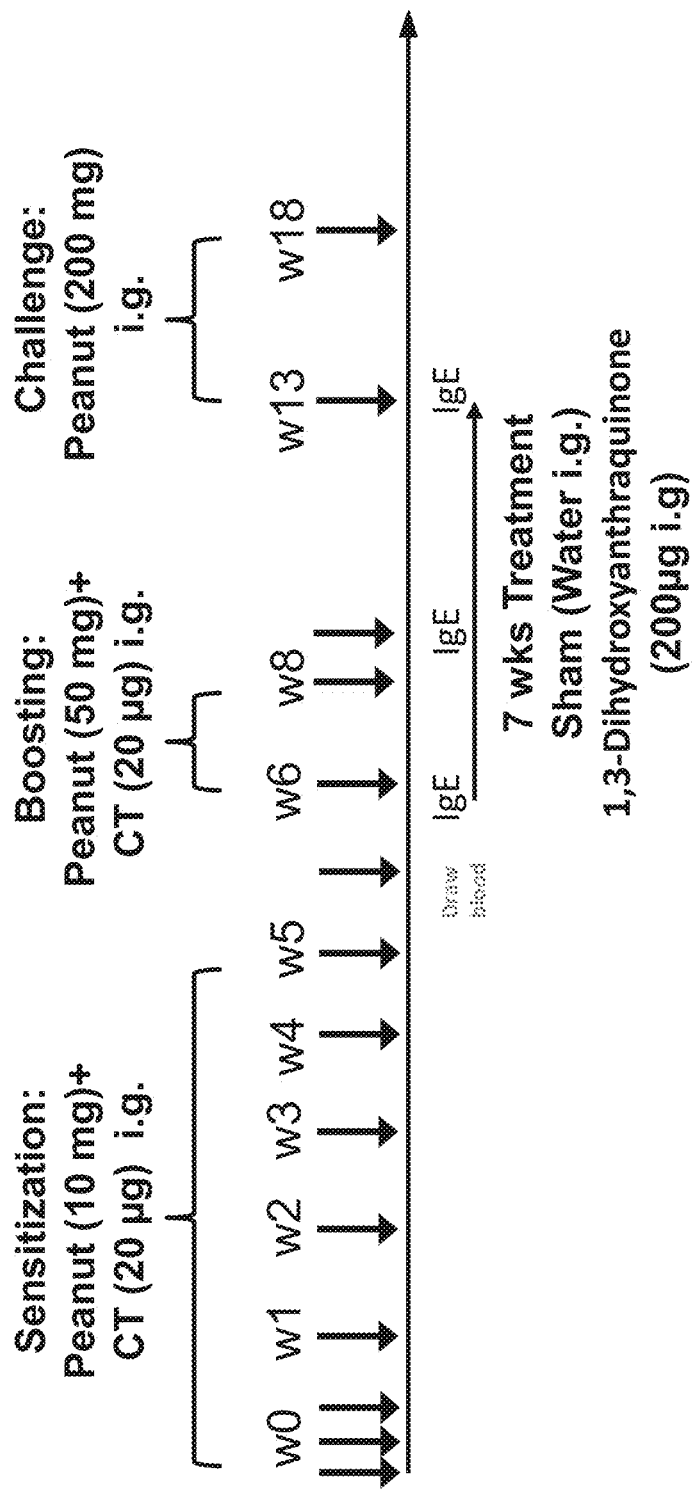
FIG. 10 illustrates the in vivo experiment protocol. Briefly, C3H/HeJ Mice were orally sensitized with 10 mg peanut and 20 mg cholera toxin weekly for 5 weeks as described in methods. At weeks 6 and 8, mice were boosted with 50 mg peanut mixed with cholera toxin. Seven weeks of 1,3-Dihydroxyanthraquinone (200 µg per mouse per day) treatment was started at week 6. Mice were challenged with PN at week 13 and 18. Mice were sacrificed 48 hours after the last challenge.

FIG. 10 illustrates the in vivo experiment protocol. C3H/HeJ Mice were orally sensitized with 10 mg peanut and 20 mg cholera toxin weekly for 5 weeks as described in methods. At weeks 6, 7 and 8, mice were boosted with 50 mg peanut mixed with cholera toxin. Seven weeks of 1,3-Dihydroxyanthraquinone (200 µg per mouse per day) treatment was started at W6. Mice were challenged with PN at week 13 and again at week 18. Mice were sacrificed 48 hours after last challenge.

Figure 11A:
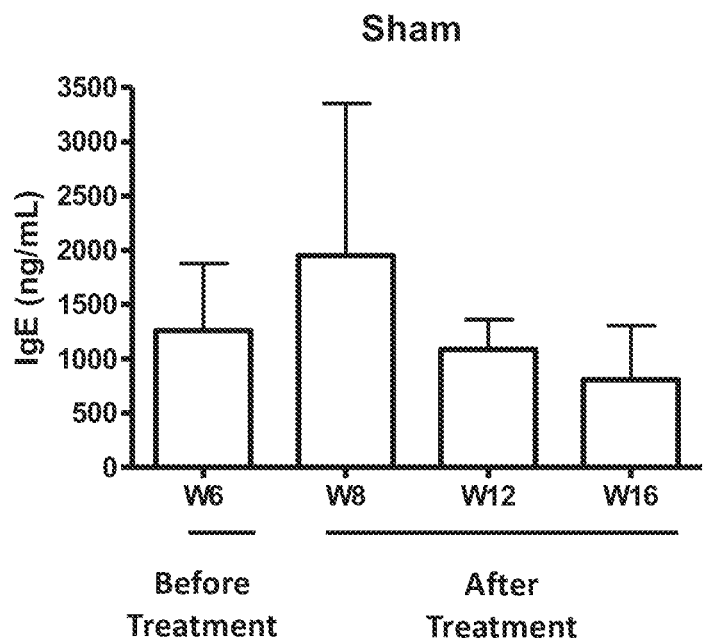
FIGS. 11A-11C show that 1,3-Dihydroxyanthraquinone inhibits IgE production in vivo. Peanut specific IgE levels of sham group (FIG. 11A) and 1,3-Dihydroxyanthraquinone treated group (FIG. 11B) at week 6 and week 12. Post treatment symptom scores (FIG. 11C) were assigned using a standard scoring system. *=$P<0.05$; **=$P<0.01$.
Figure 11B:
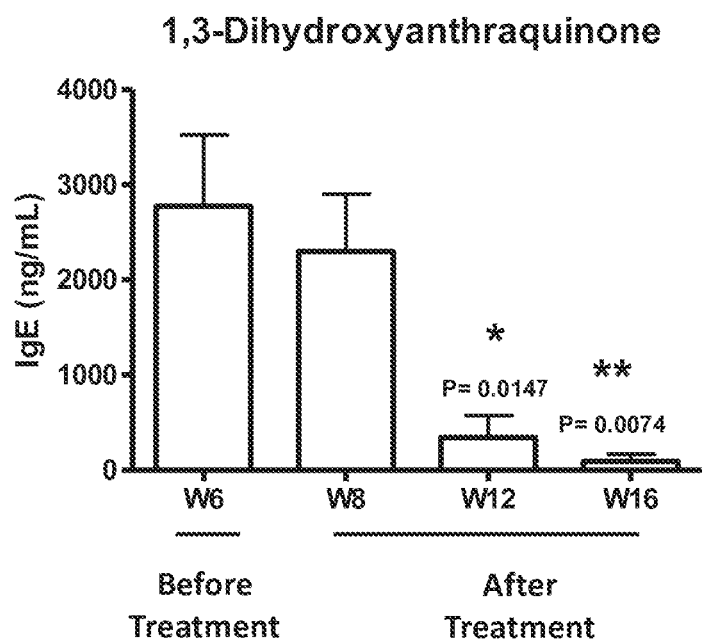
Figure 11C:
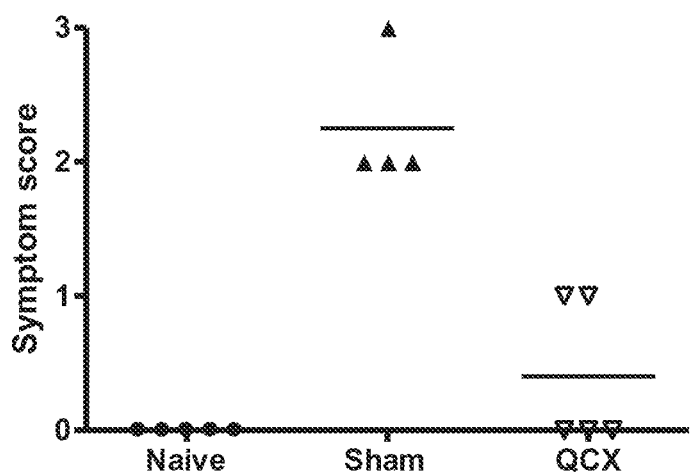

FIG. 11B illustrates 1,3-Dihydroxyanthraquinone inhibition of IgE production in vivo. Peanut-Specific IgE was measured by ELISA. Sham treated group showed constant high IgE values (FIG. 11A). 1,3-Dihydroxyanthraquinone treated grouped showed markedly reduced significant IgE levels at weeks 12 and 16 (FIG. 11B). Symptom scores following challenge were assigned using a standard scoring system (FIG. 11C). 1,3-Dihydroxyanthraquinone treated mice exhibited significantly weaker reactions than sham treated mice. *=P<0.05; **=P<0.01.

Figure 12A:
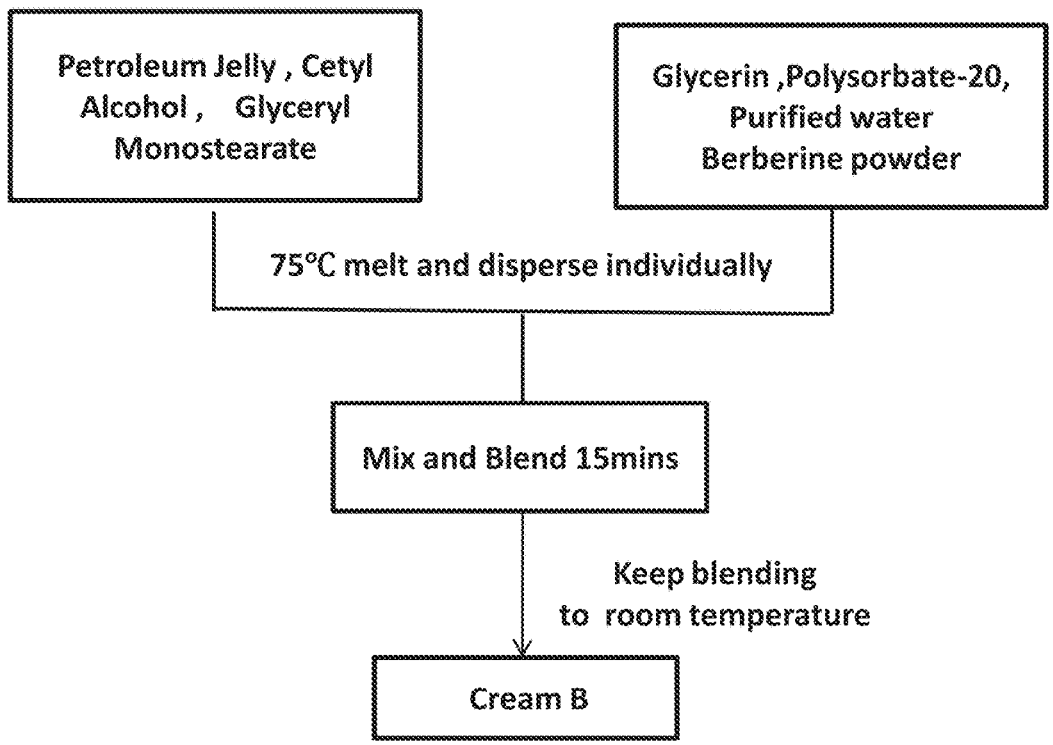
FIG. 12A shows a flow chart of berberine cream preparation.
Figure 12B:
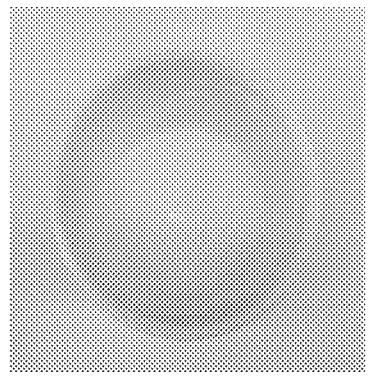
FIG. 12B displays the final product.

FIG. 12A shows a flow chart of berberine cream preparation and FIG. 12B shows the final product.

Figure 13:
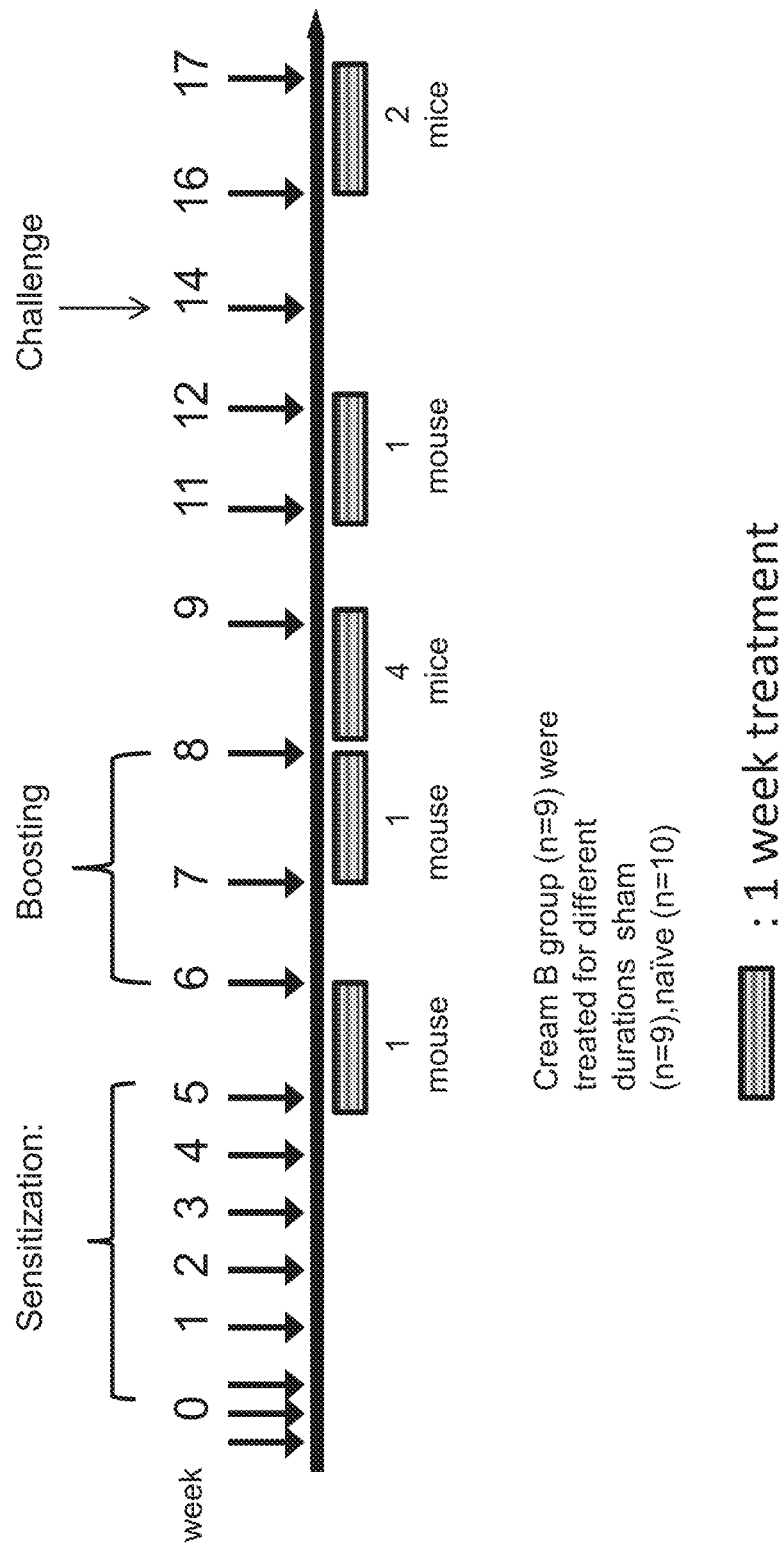
FIG. 13 shows the effects of 1,3-Dihydroxyanthraquinone on IgE production. Briefly, C3H/HeJ mice were subjected to weekly oral peanut (PN) sensitization [10 mg with cholera toxin (CT) at 20 ug] from week 0 to week 5 and boosted at week 6 and 8 with PN (50 mg with CT at 20 ug). Before 24 hours of treatment, the back hair of PN allergic mice were shaved (the area ~2.1 cm*1.5 cm). 100 mg berberine cream were applied on shaved rostral back skin once a day for 1 week. Mice were treated differently at different period of time. Each treatment period was 7 days. Petroleum Jelly (sham)-treated group ($n=11$) and naïve ($n=10$) mice served as controls.

In FIG. 13 C3H/HeJ mice were sensitized by oral administration of 10 mg PN plus 20 ug cholera toxin (CT) on 3 consecutive days during week 0, then weekly during weeks 1-5 and boosted at weeks 6 and 8 with 50 mg PN and 20 ug CT. 24 hours before treatment, peanut (PN)-allergic mice were anesthetized with a mixture of ketamine and xylazine and a 2.1 cm 1.5 cm area of rostral back hair was shaved. Treated mice received 100 mg berberine cream applied daily to the shaved skin for 7 days. Treatment was initiated at different time periods post sensitization: mouse No. 1 at week 5, mouse No. 2 at week 7, mice Nos. 3-6 at week 8, mouse No. 7 at week 11, mice 8,9 at week 16 (post challenge). Vehicle (sham)-treated group (n=11) and naïve (n=10) mice served as controls.

Figure 14A:
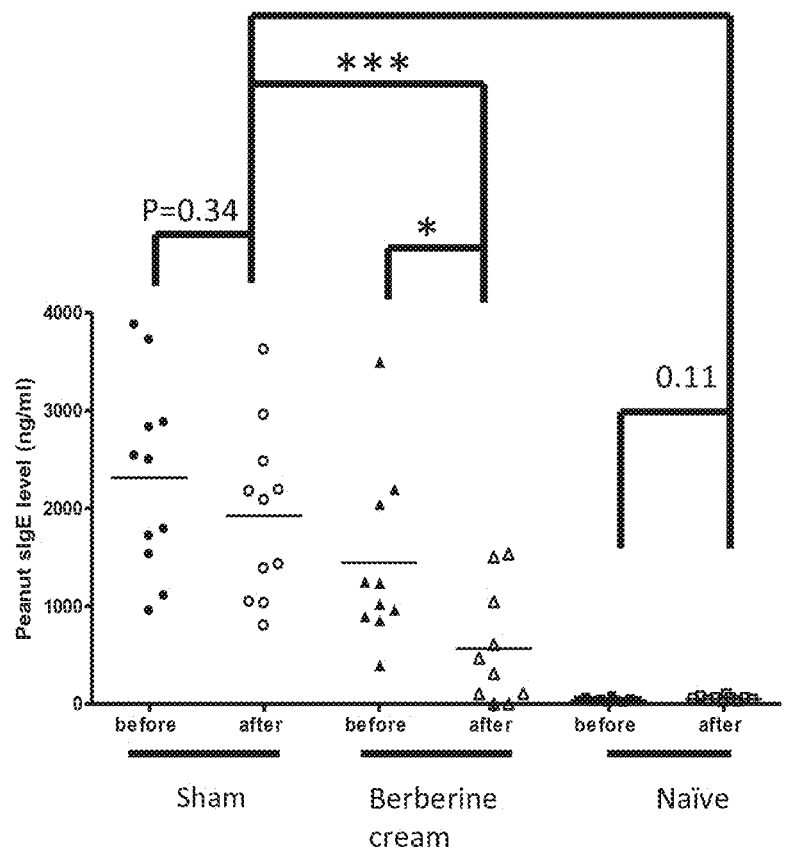
FIGS. 14A and 14B show the effect of berberine Cream on serum peanut-specific IgE (FIG. 14A) and Total IgE (FIG. 14B) levels. Sera were obtained 1 day before treatment and 1 day after treatment. Serum peanut-specific IgE and total IgE levels were determined by ELISA. Data are means±SEMs for each group from 3 sets (sham, $n=11$; Berberine Cream $n=9$, naive, $n=10$) *$P<0.05$ $P<0.01$, *$P<0.001$
Figure 14B:
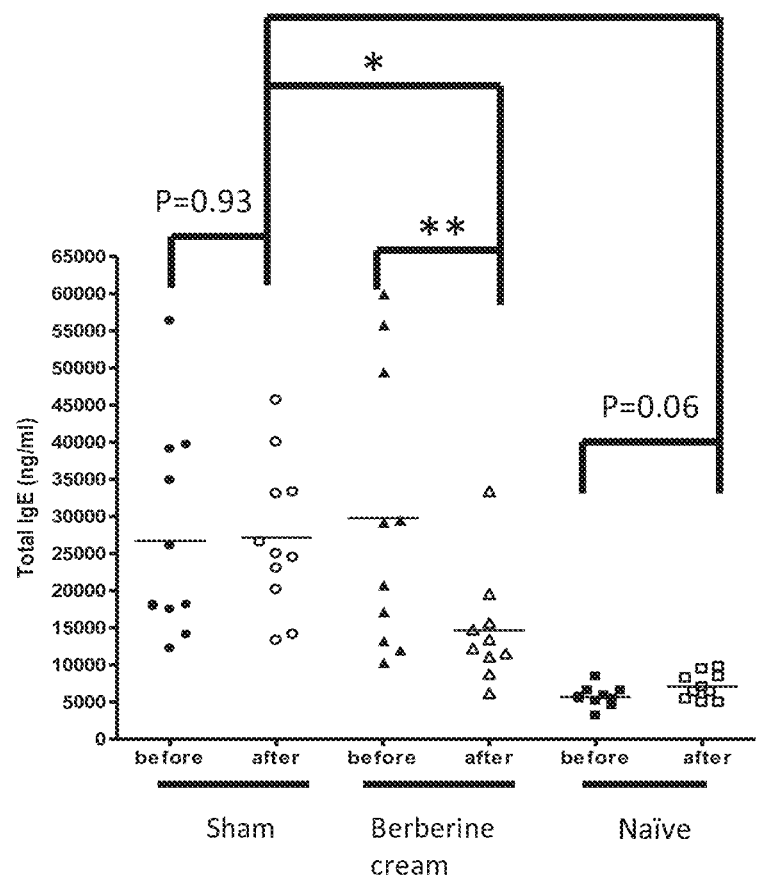

FIG. 14A shows the effect of berberine cream on serum peanut-specific IgE and FIG. 14B shows the effect of berberine on total IgE levels. Sera were obtained 1 day before and one day after the one-week long treatment. Peanut-specific IgE and total IgE levels were determined by ELISA and they were significantly reduced in berberine cream treated mice than sham treated mice. Data are means±SEMs for each group; (sham, n=11; Berberine cream, n=9, naive, n=10); *, P<0.05; , P<0.01;*, P<0.001.

Figure 15A:
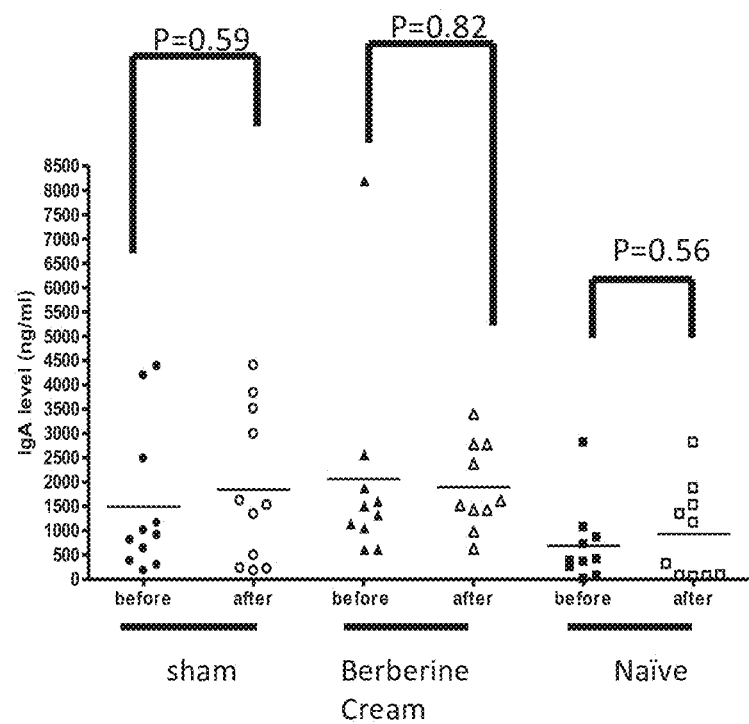
FIGS. 15A and 15B show the effect of Cream 3B on serum peanut-specific IgA (FIG. 15A) and total IgG (FIG. 15B) levels. Sera were obtained 1 day before and after treatment. Serum total IgA and IgG levels were determined by ELISA. Data are means±SEMs for each group from 3 sets (sham, $n=11$; Berberine cream $n=9$, naive, $n=10$)
Figure 15B:
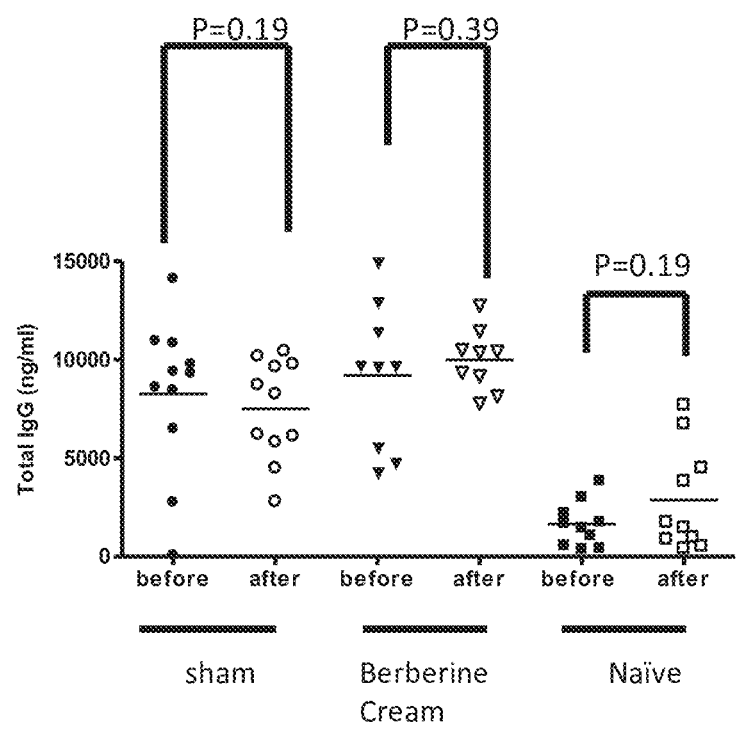

FIG. 15A shows the effect of berberine cream on serum peanut-specific IgA and FIG. 15B the effect of berberine cream on total IgG levels. Sera were obtained 1 day before and 1 day after treatment. Serum total IgG levels and IgA levels were determined by ELISA. No significant difference was found between the groups. Data are means±SEMs for each group from 3 sets (sham, n=11, Berberine cream n=9, naive, n=10)

Figure 16A:
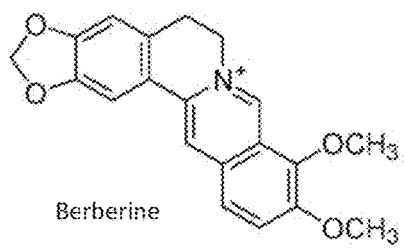
FIG. 16A shows the chemical structure of berberine.
Figure 16B:
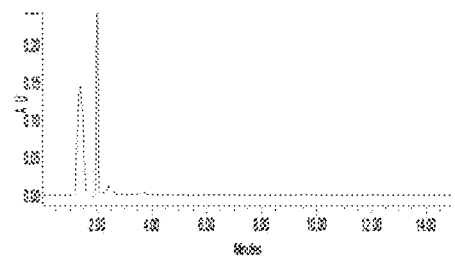
FIG. 16B shows the chromatogram of mouse blank plasma.
Figure 16C:
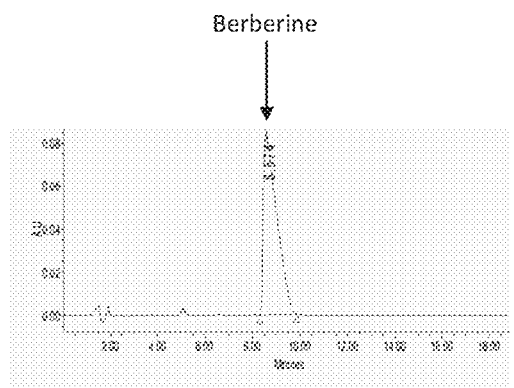
FIG. 16C shows mouse blank plasma spiked with 99.3 ug/ml berberine.
Figure 16D:
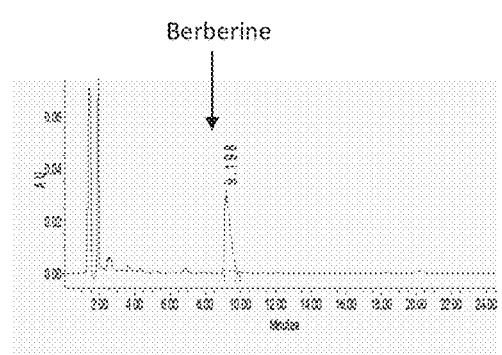
FIG. 16D shows mouse plasma 4 h after the topical administration of Berberine cream (1.5% w/v).
Figure 16E:
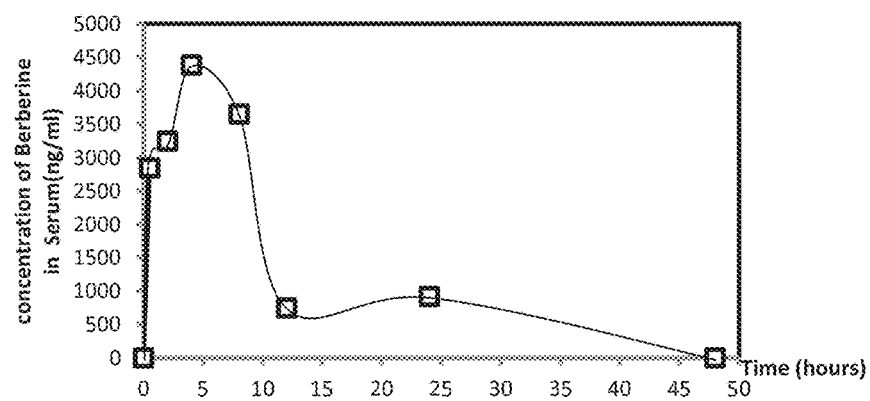
FIG. 16E shows the concentration-time profile of Berebrine cream applied on the dorsa of C3HJ/He mouse at a dosage of 100 mg for 24 hour. The concentration of berberine in plasma samples was measured by HPLC. Data are presented as mean±SD ($n=3$) Peak analysis and assignment were performed using standard samples and HPLC methods.

In FIGS. 16A-16E various berberine related results are shown. Chemical structure of berberine (FIG. 16A). Chromatograms of mouse blank plasma (FIG. 16B) Mouse blank plasma spiked with 99.3 ug/ml berberine (FIG. 16C). Mouse plasma 4 h after topical administration of berberine cream (1.5% w/v) (FIG. 16D). Concentration-time profile of berberine in mouse plasma after topical application of 100 mg of berberine cream to the dorsal skin of a C3HJ/HeJ mouse (FIG. 16E). The concentration of berberine in plasma samples was measured by HPLC. Data are presented as mean±SD (n=3) Peak analysis and assignment were performed using standard samples and HPLC methods.

Figure 17A:
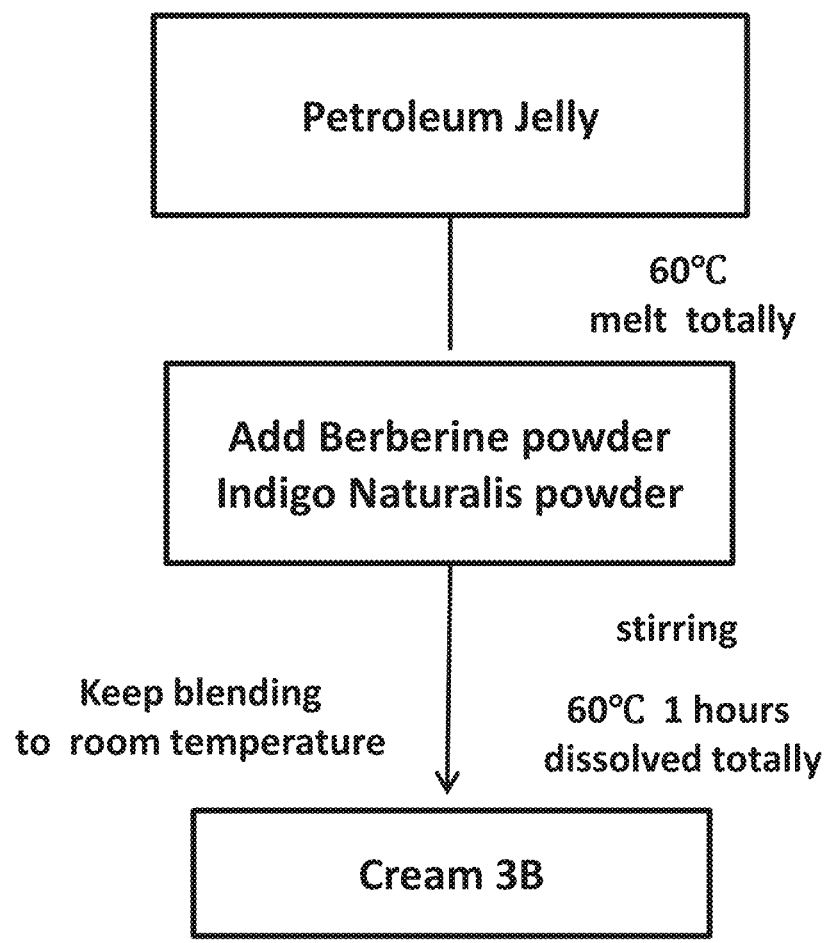
FIG. 17A is a flow chart of berberine+indigo+indirubin cream (Cream 3B) preparation.
Figure 17B:
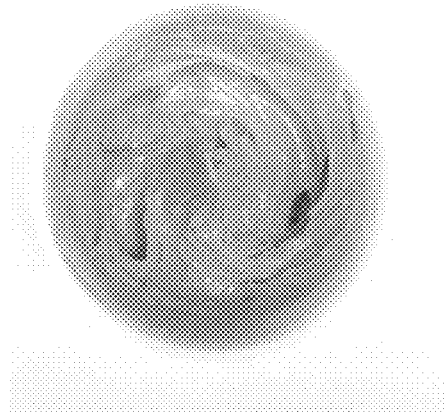
FIG. 17B displays the final product.

FIGS. 17A-17B illustrate the formulation of a topical cream containing berberine. Flow chart of berberine+indigo+indirubin cream (Cream 3B) preparation (FIG. 17A) and the final product (FIG. 17B) is shown. Cream 3B is a homogeneous, semi-solid preparation, including berberine, indigo nNaturalis, zinc oxide, penetration enhancer, hydrophobic bases, natural fragrance, intended for external application to the skin fortherapeutic purposes. Preparation: berberine 0.5-1% (w/v), indigo naturalis 1.5% (w/v), zinc oxide 7.2% as active ingredients. Inactive ingredients include butylated hydroxyanisole (BHA), cod liver oil lanolin, methylparaben, talc, water, petroleum jelly, lavender pure essential oil natural fragrance and as well as borneol 0.5-0.86% as a penetration enhancer. For preparation Cream 3B, inactive ingredients (BHA, cod liver oil, lanolin, methylparaben, talc, water, petroleum jelly) are mixed in a glass container, keep in water bath at 60° C., stirring, until all melt completely. Berberine, indigo naturalis, zinc oxide and borneol solution are added, continue stirring until fully mixed. The mixture is cooled down to room temperature in order form homogeneous cream.

Figure 18:
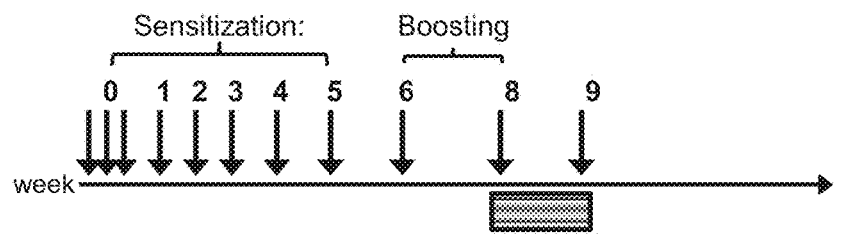
FIG. 18 shows the in vivo Cream 3B experimental protocol. C3H/HeJ mice were subjected to weekly oral peanut (PN) sensitization [10 mg with cholera toxin (CT) at 20 ug] from week 0 to week 5 and boosted at week 6 and 8 with PN (50 mg with CT at 20 ug). Before 24 hours of treatment, the back hair of PN allergic mice were shaved (the area ~2.1 cm*1.5 cm). 200 mg cream 3B were applied on shaved rostral back skin once a day for 1 week. Each treatment period was 7 days. Set#1 group (n=4) was treated at week 8; Set#2 group (n=5) was challenged at week 14 with PN (200 mg with CT at 20 ug) and treated at week 16; Set#3 group (n=5) was challenged at week 14 and 20 with PN as same dose above and treated at week 19. Petroleum Jelly (sham)-treated group (n=14) and naïve (n=10) mice served as controls.
Figure 18:
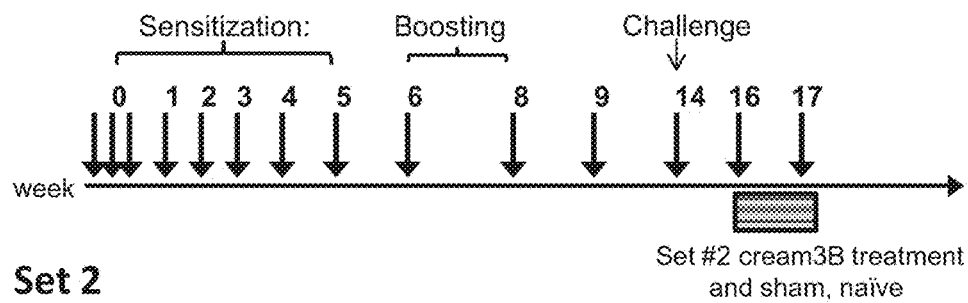
Figure 18:
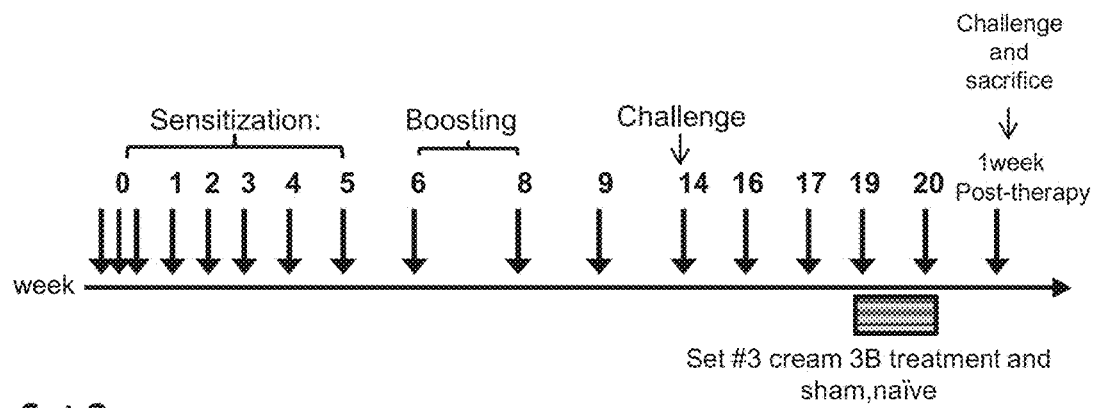

FIG. 18 shows the in vivo Cream 3B experimental protocol: C3H/HeJ mice were orally sensitized 3 times during week 0 with 10 mg peanut and 20 ug cholera toxin (CT), then weekly through week 5, boosted at weeks 6 and 8 (50 mg PN and 20 ug CT), and challenged at week 14. 24 hours before treatment, mice were anesthetized with a mixture of ketamine and xylazine and an area about 2.1 cm 1.5 cm on their backs were shaved. 200 mg of Cream 3B and sham treatment were applied daily for 1 week. Three sets of treatment protocols were performed at different time points following initial sensitization. Set#1, mice (n=4/group) were treated at weeks 8-9 following initial sensitization. Set#2, mice were (n=5/group) treated at weeks 16-17 following initial sensitization (2 weeks following challenged) and Set#3 (n=5), at week 19. Set#3 mice were sacrificed, and mesenteric lymph nodes (MLN, spleens and plasma were harvested. Petroleum Jelly (sham)-treated group (n=14) and naïve (n=10) mice served as controls.

Figure 19A:
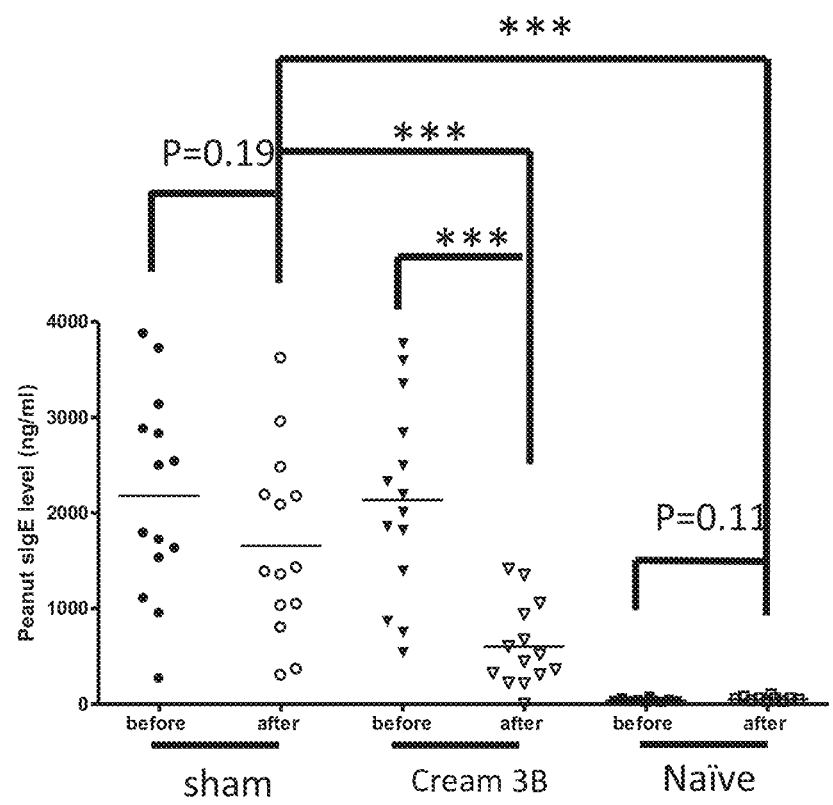
FIGS. 19A and 19B show the effect of Cream 3B on serum peanut-specific IgE (FIG. 19A) and Total IgE (FIG. 19B) levels. Sera were obtained 1 day before treatment and 1 day after treatment. Serum peanut-specific IgE and total IgE levels were determined by ELISA. Data are means±SEMs for each group from 3 sets (sham, n=14; cream 3B n=14, naive, n=10) They were significantly lower in Cream 3B treated mice than in sham treated mice. *P<0.05 P<0.01, *P<0.001.
Figure 19B:
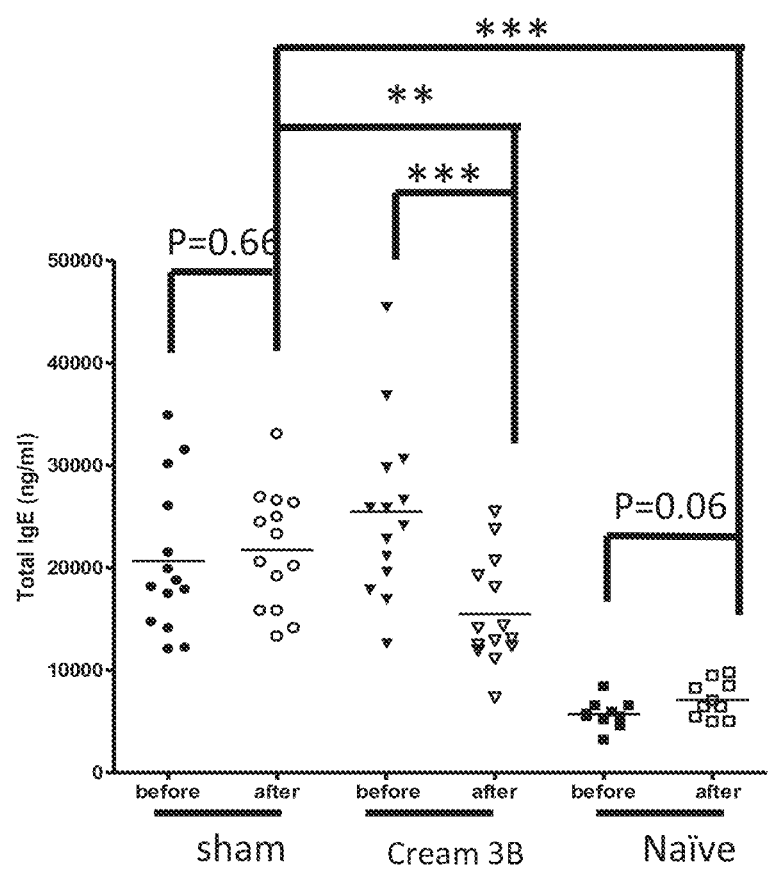

FIGS. 19A and 19B show the effect of Cream 3B on serum peanut-specific IgE (FIG. 19A) and Total IgE (FIG. 19B) levels. Sera were obtained 1 day before treatment and 1 day after treatment. Serum peanut-specific IgE and total IgE levels were determined by ELISA. They were significantly lower in Cream 3B treated mice than in sham treated mice. Data are means±SEMs for each group of 3 sets (sham, n=14; cream 3B n=14, naive, n=10) *, P<0.05; , P<0.01; *, P<0.001.

Figure 20:
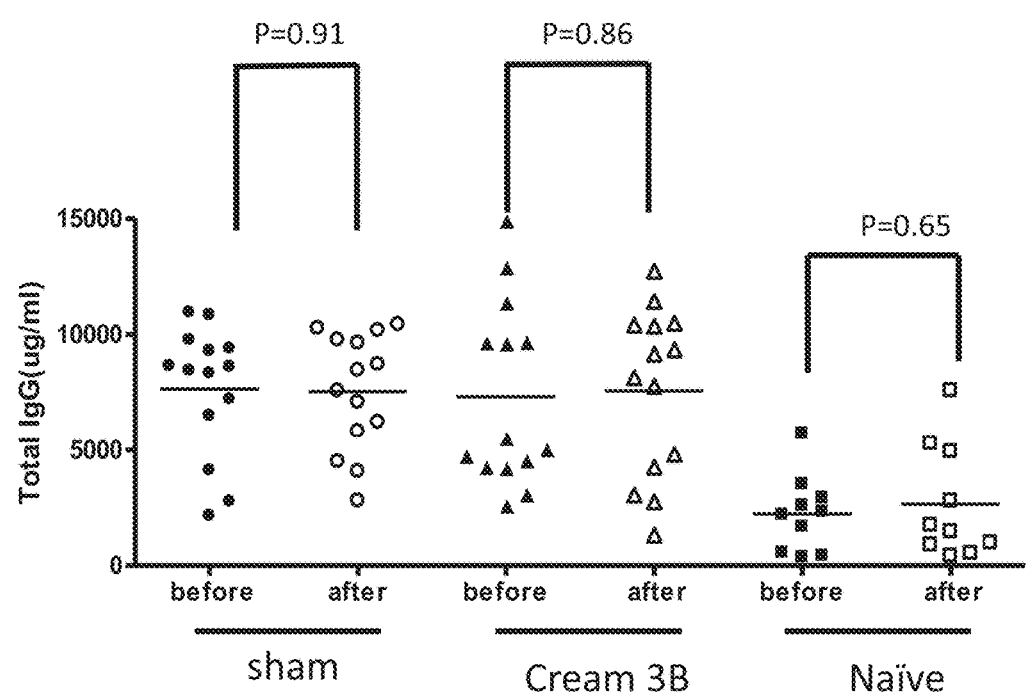
FIG. 20 shows the effect of Cream 3B on serum total IgG levels. Sera were obtained 1 day before and after treatment. Serum total IgG levels were determined by ELISA. Data are means±SEMs for each group from 3 sets (sham, n=14; cream 3B n=14, naive, n=10)

FIG. 20 shows the Effect of Cream 3B on serum total IgG levels. Sera were obtained 1 day before and after treatment. Serum total IgG levels were determined by ELISA. Data are means±SEMs for each group from 3 sets (sham, n=14; Cream 3B n=14, naive, n=10)

Figure 21:
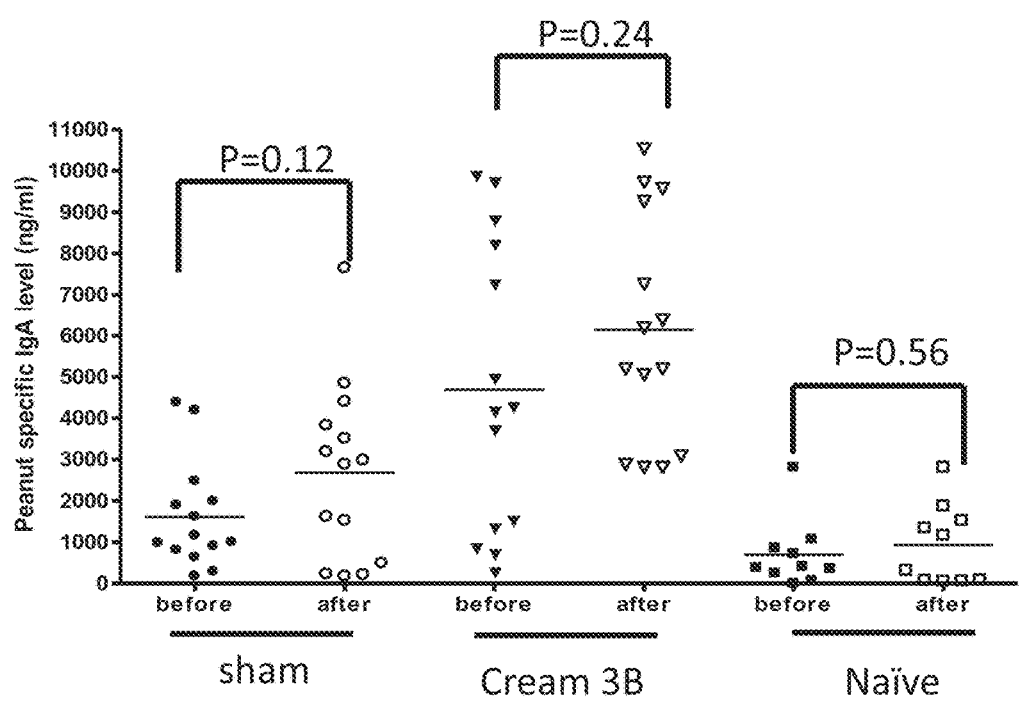
FIG. 21 shows the effect of Cream 3B on serum peanut-specific IgA levels. Sera were obtained 1 day before and after treatment. Serum peanut-specific IgA were determined by ELISA. Data are means±SEMs for each group from 3 sets (sham, n=14; cream 3B n=14, naive, n=10).
Figure 22A:
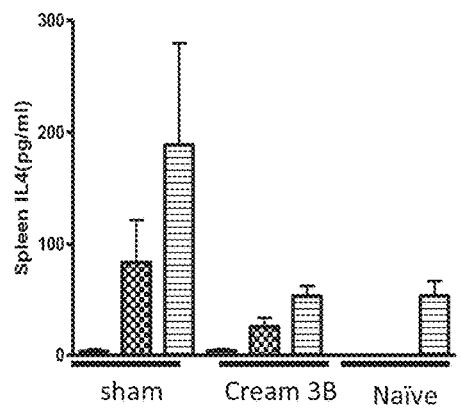
FIGS. 22A-22F show the IL4, IL10 and IFN-r cytokine levels in splenocyte and mesenteric lymph node cultures (MLN) under different treatments. Specifically.
Figure 22B:
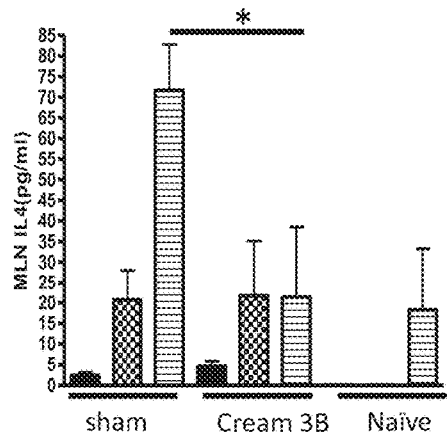
Figure 22C:
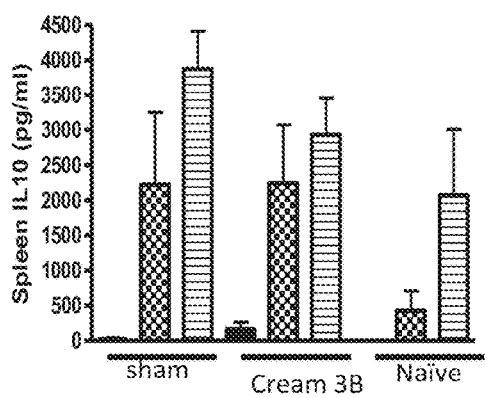
Figure 22D:
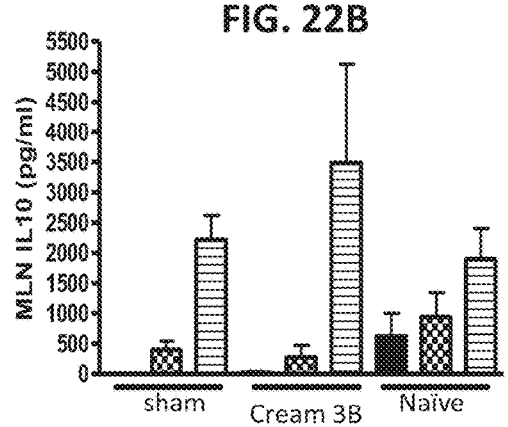
Figure 22E:
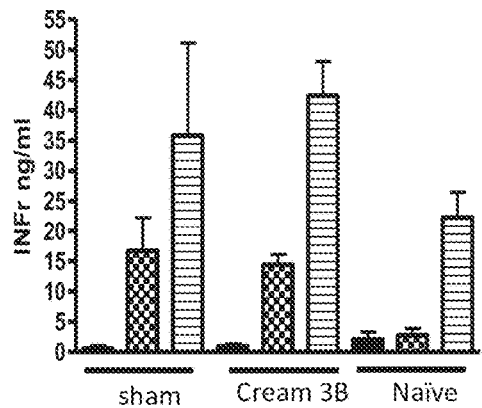
Figure 22F:
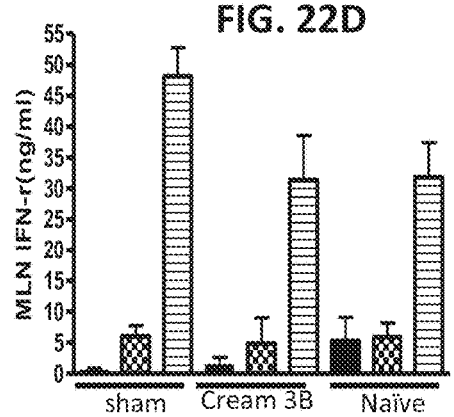

FIG. 21 shows the Effect of Cream 3B on serum peanut-specific IgA levels. Sera were obtained 1 day before and after treatment. Serum peanut-specific IgA levels were determined by ELISA. Data are means±SEMs for each group from 3 sets (sham, n=14; Cream 3B n=14, naive, n=10

FIGS. 22A-22F show several cytokines in splenocyte and mesenteric lymph node cultures. Splenocytes (SPC) and mesenteric lymph node (MLN) cells obtained immediately after evaluation of anaphylactic reactions following the final challenge were cultured in complete culture medium in the presence of CPE (Crude Peanut Extract) antigen, Con A, or medium alone. Supernatants were collected 72 hours later, and IL-4 (FIGS. 22A and 22B), IL-10 (FIGS. 22C and 22D) and IFN-r (FIGS. 22E and 22F) were determined by ELISA. Data are shown as mean±SEM of cultures measured in duplicate experiments (n=5). *, P<0.05 vs. sham.

Figure 23A:
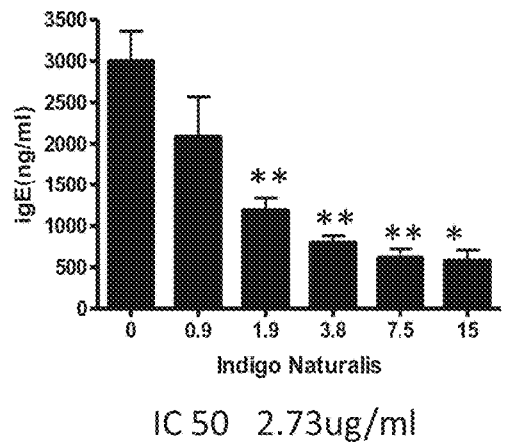
FIGS. 23A-23D show the dose-dependent inhibition of Indigo naturalis, indirubin and the combination of berberine and indigo naturalis on IgE production by U266 cells. U266 cells were cultured with indigo naturalis (FIG. 23A), indirubin (FIG. 23B), and the combination of berberine with Indigo naturalis (FIG. 23C) at different concentrations as indicated for 6 days. The supernatants were harvested and IgE levels were measured by ELISA. Results were expressed as the mean±SME. *, p<0.05; **, p<0.01 (n≥3). IC50 value has been calculated.
Figure 23B:
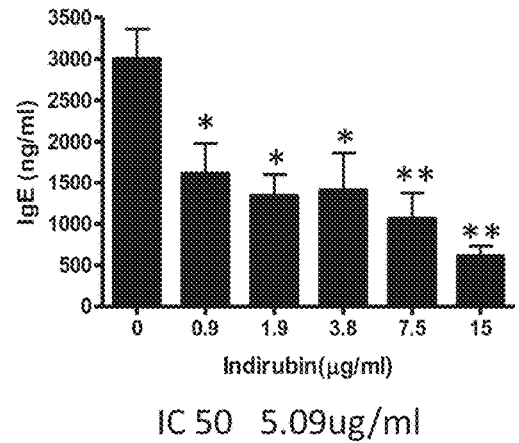
Figure 23C:
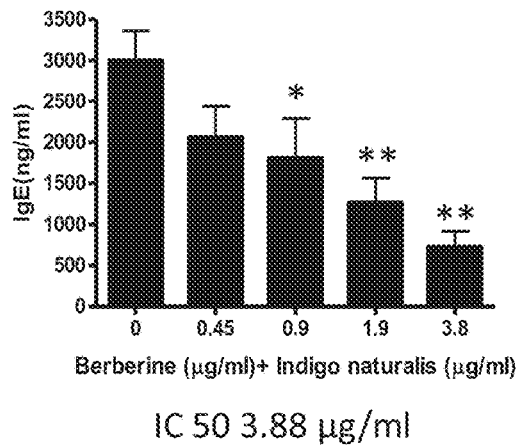
Figure 23D:
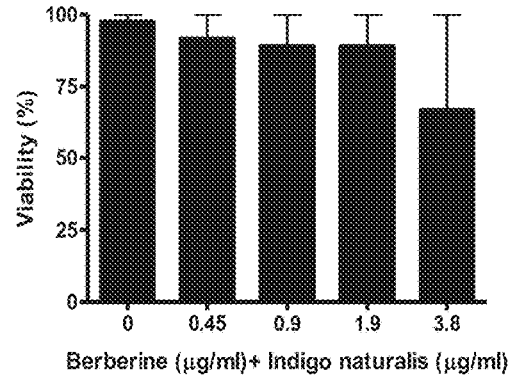

FIGS. 23A-23D show Dose-dependent inhibition by Indigo naturalis (FIG. 23A), indirubin (FIG. 23B), and a combination of berberine and indigo naturalis (FIG. 23C) on IgE production by U266 cells. U266 cells were cultured with individual components and the combination of berberine and Indigo naturalis at different concentrations as indicated for 6 days. IgE supernatants levels were IgE levels were measured by ELISA. Results are expressed as the mean±SME. *, p<0.05; **, p<0.01 (n≥3). IC 50 value has been given. Cell viability at different concentrations of combination of berberine and indigo naturalis was evaluated (FIG. 23D).

Figure 24A:
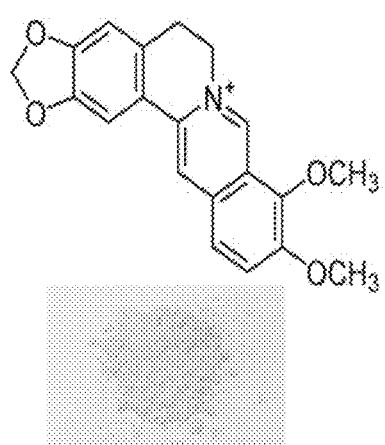
FIG. 24A illustrates the chemical structures of berberine, indigo, and indirubin.
Figure 24A:
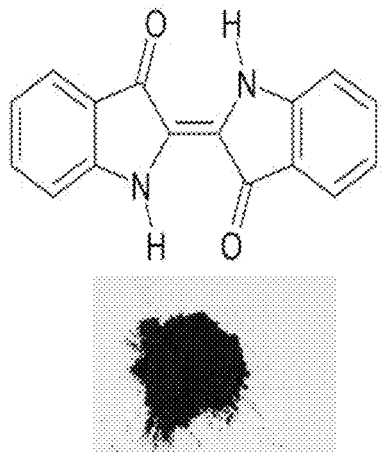
Figure 24A:
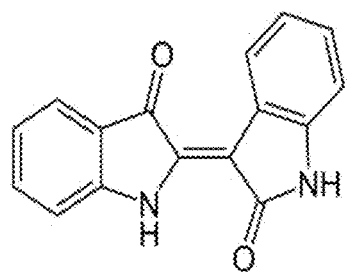
Figure 24E:
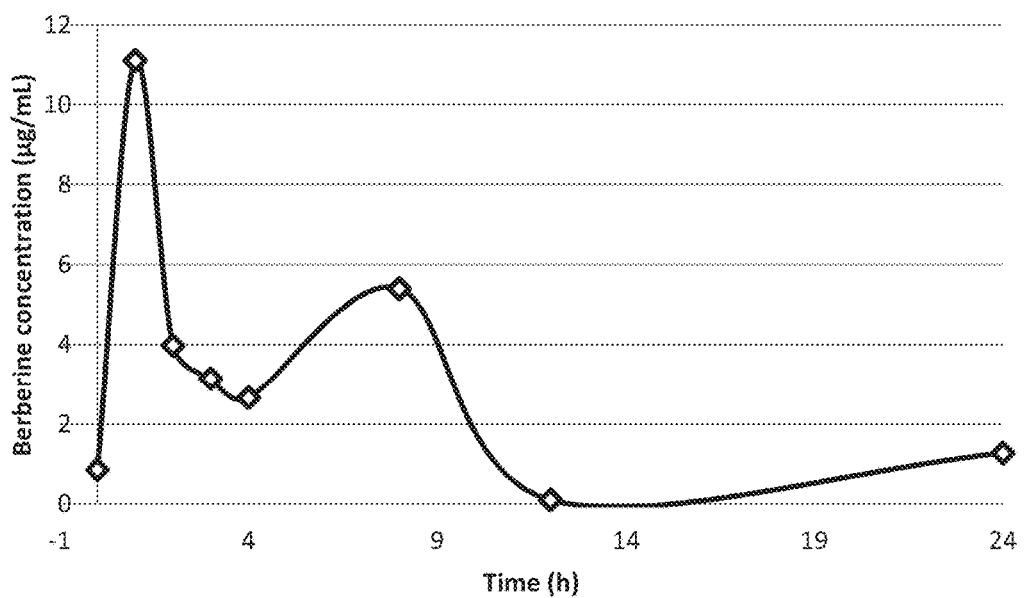
FIG. 24E displays the concentration-time profile of Cream 3B applied on the dorsa of C3HJ/He mouse at a dosage of 200 mg for 24 hours. The concentration of berberine in plasma samples was measured by HPLC. Data are presented mean±SD (n=3). Peak analysis and assignment were performed using standard samples and HPLC method.

FIGS. 24A-24E show various compounds as they are formulated into a topical cream, according to a specific embodiment of the invention. Berberine powder and Indigo naturalis extract powder, Chemical structure of berberine, and the two main compounds in Indigo Naturalis: indigo and indirubin (FIG. 24A). HPLC fingerprint of indigo naturalis extract powder (FIG. 24B), HPLC fingerprint of Cream 3B (FIG. 24C), HPLC fingerprints overlay of berberine, indigo and indirubin standard individually (FIG. 24D), three substances are shown by labels. Cream 3B percutaneous Absorption after topical application (FIG. 24E). Concentration-time profile of Cream 3B applied on the dorsa of C3HJ/He mouse at a dosage of 200 mg for 24 hour. The concentration of berberine in plasma samples was measured by HPLC. Data are presented mean±SD (n=3) Peak analysis and assignment were performed using standard samples and HPLC method.

Figure 34:
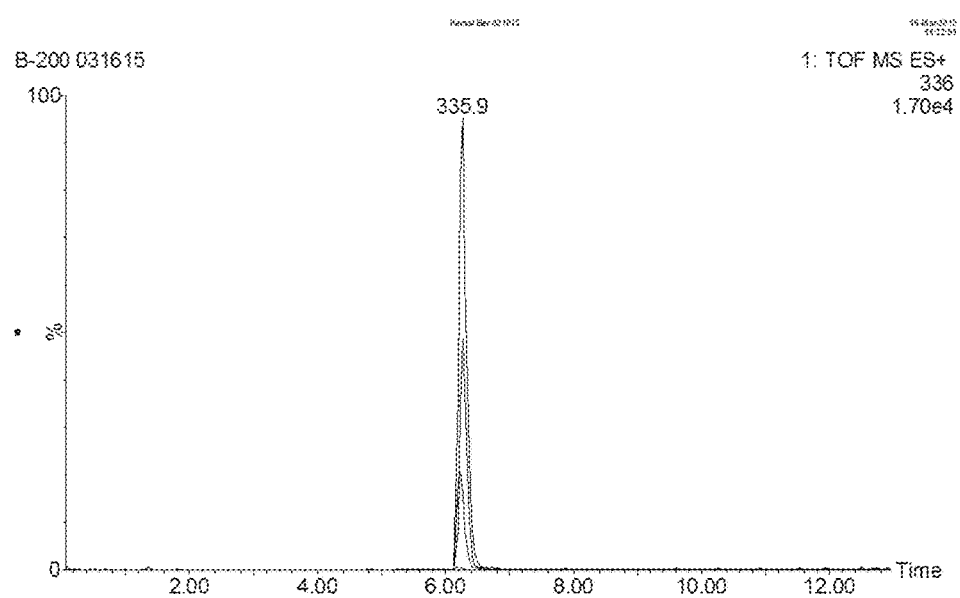
FIG. 34 shows the LC-MS detection of berberine. The peak intensities of berberine at different incubation concentration were listed for the generation of standard curve.

FIG. 34 shows the LC-MS detection of berberine. Berberine in Cacao-2 cells was detected using LC-MS. The peak intensities of berberine at different incubation concentration were listed for the generation of standard curve.

Figure 35:
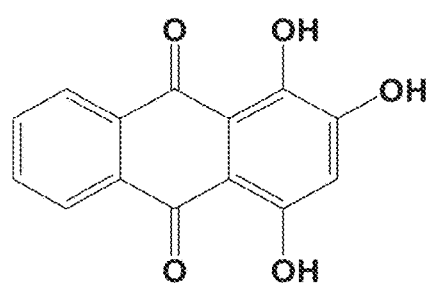
FIG. 35 shows the chemical structures of active compounds isolated from *Rubia Cordifolia* and *Arctium Lappa* L.
Figure 35:
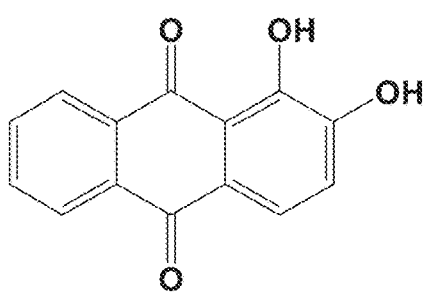
Figure 35:
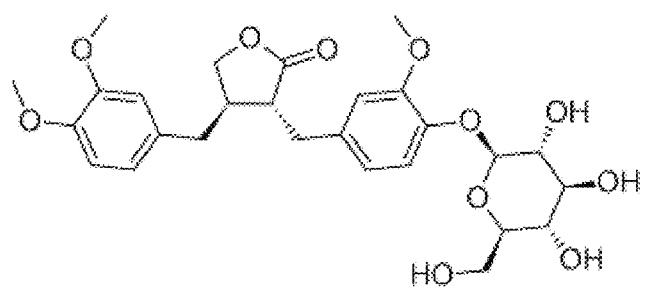
Figure 35:
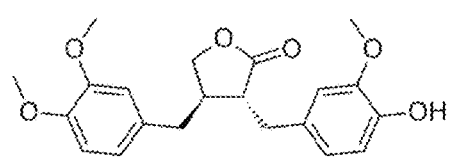

FIG. 35 shows the chemical structures of active compounds isolated from *Rubia Cordifolia* and *Arctium Lappa* L. Purpurin and alizarin were identified from *Rubia cordifolia* L. Arctiin and arctigenin were isolated and identified from *Arctium lappa* L.

Figure 36A:
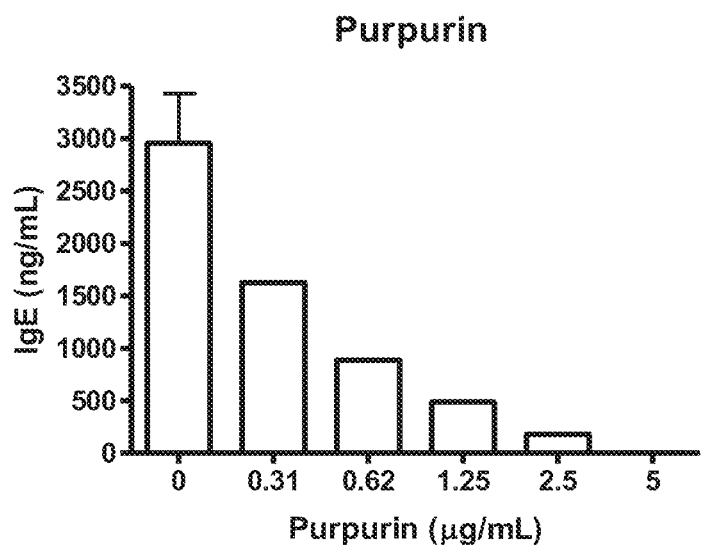
FIGS. 36A-36E show the dose-dependent effect of active compounds on IgE production by U266 cells.
Figure 36B:
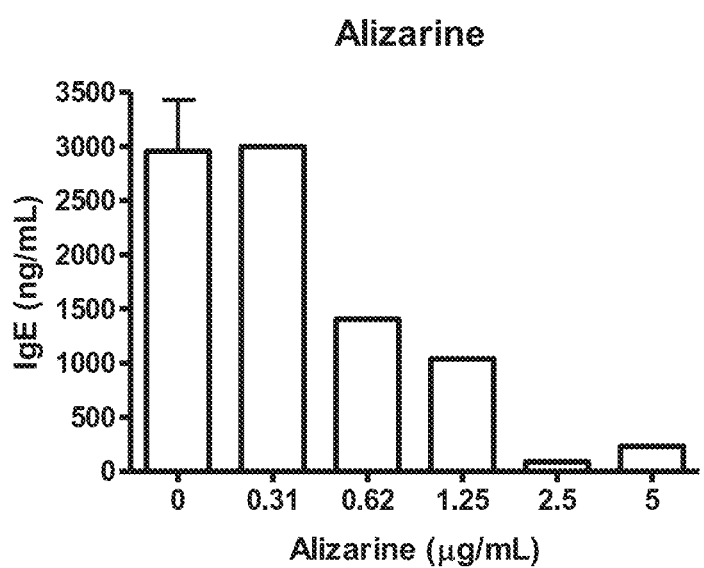
Figure 36C:
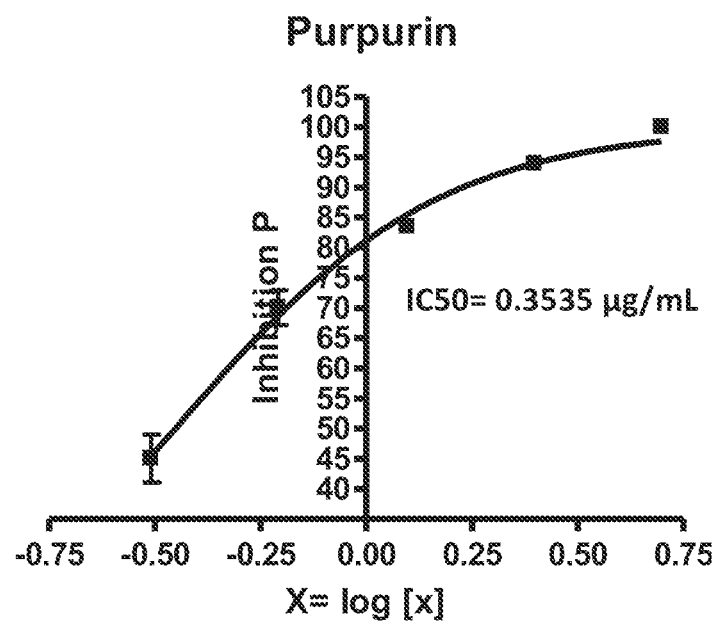
Figure 36D:
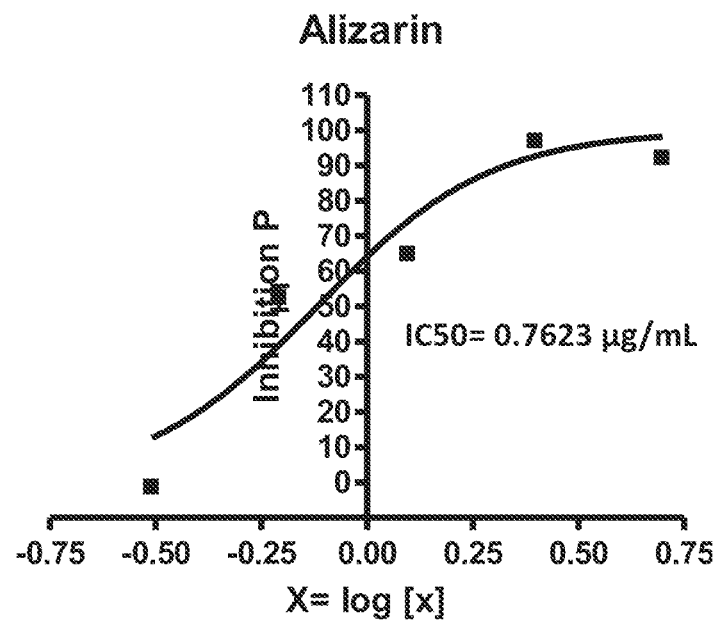
Figure 36E:
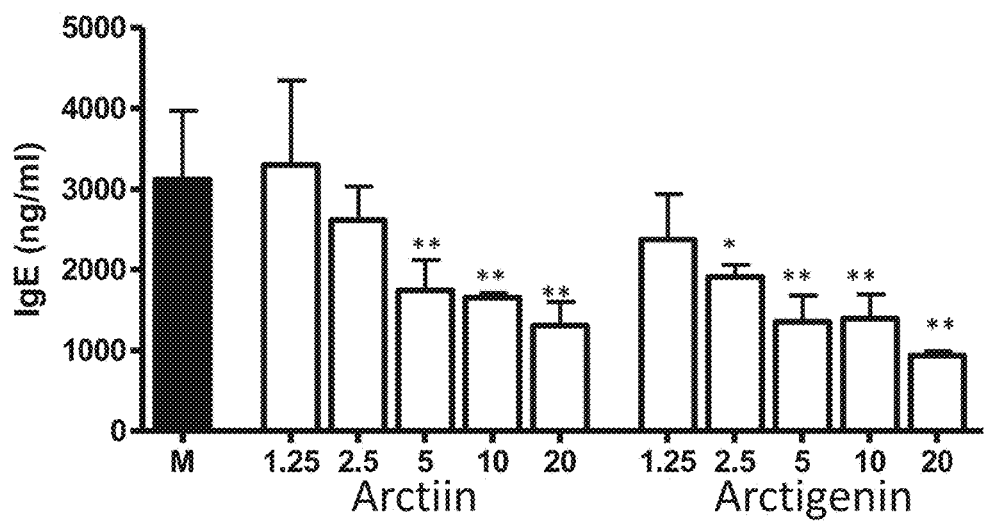

FIGS. 36A and 36B show the dose-dependent effect of active compounds Purpurin and Alizarine on IgE production by U266 cells. FIGS. 36C and 36D show the inhibitory effect of purpurin and alizarin from *Rubia cordifolia* L on IgE production by U266 cells. FIG. 36E shows the inhibition percentage of purpurin and alizarin on IgE production by U266 cells. Inhibition effect of arctiin and arctigenin from *Arctium lappa* L. on IgE production by U266 cells. U266 cells (2×105 cells/mL) were cultured with each compound at equivalent concentrations as indicated for 6 days. The supernatants were harvested and IgE levels were measured by ELISA. Results were expressed as the mean±S.E. *, $p<0.05$; **, $p<0.01$ (n≥3).

Figure 37A:
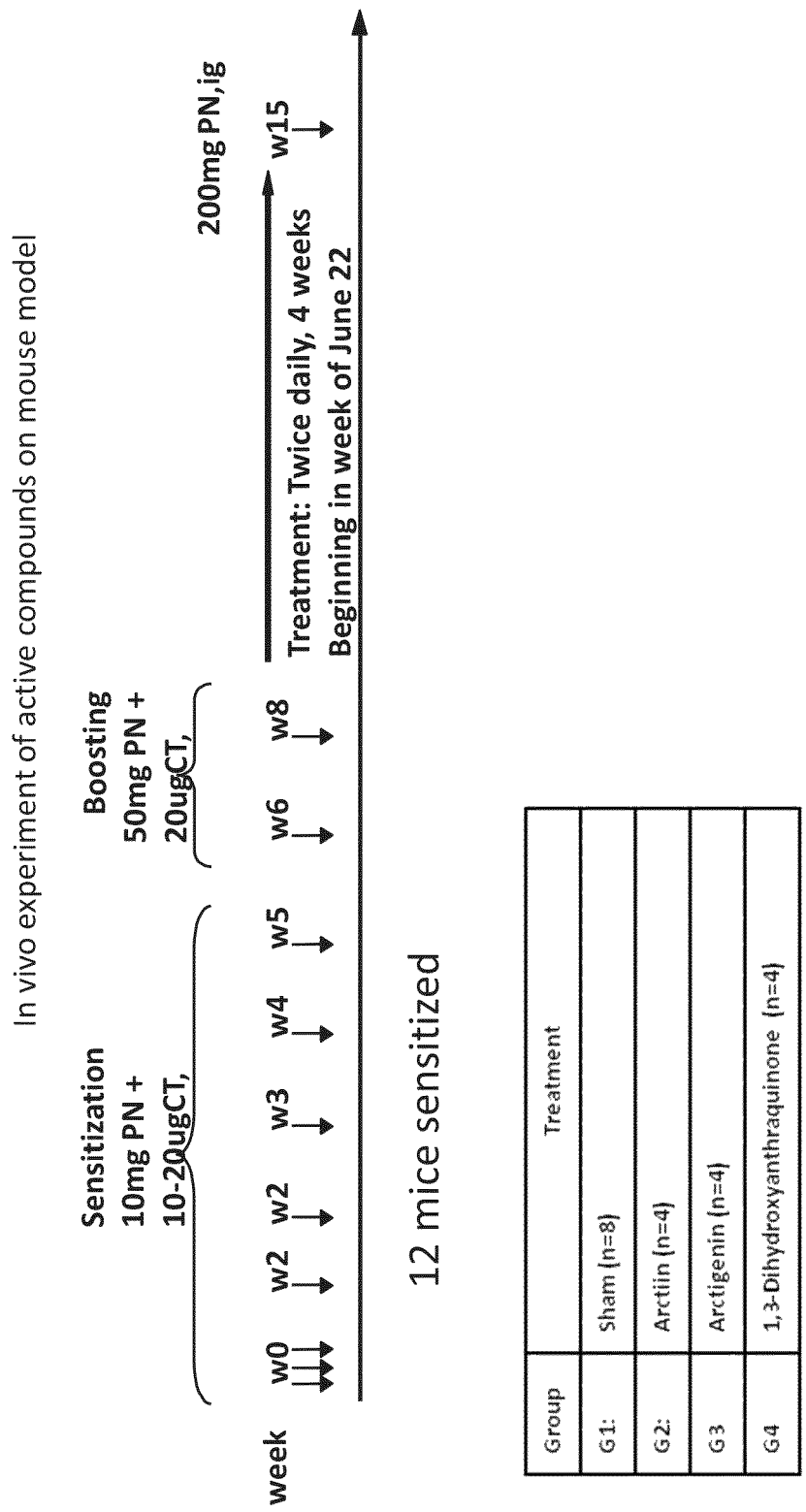
FIGS. 37A-37E. The bioactivities of compounds arctiin, arctigenin and 1,3-dihydroxyanthraquinone, on mouse model of peanut allergy. For comparison, the data show 1,3-dihydroxyanthraquinone is the most effective compound in protection against acute peanut-induced anaphylaxis.
Figure 37B:
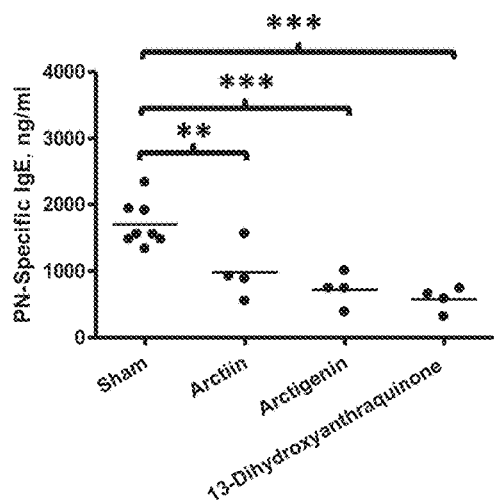
Figure 37C:
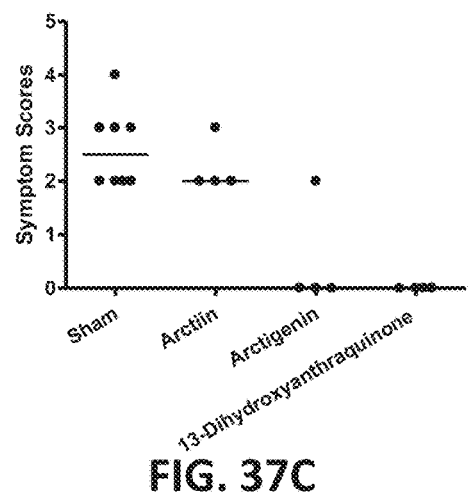
Figure 37D:
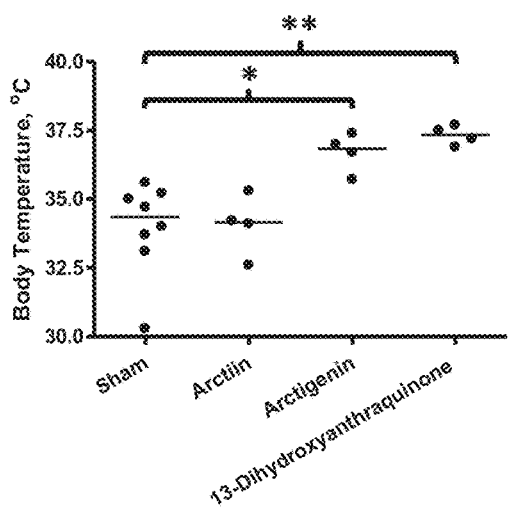
Figure 37E:
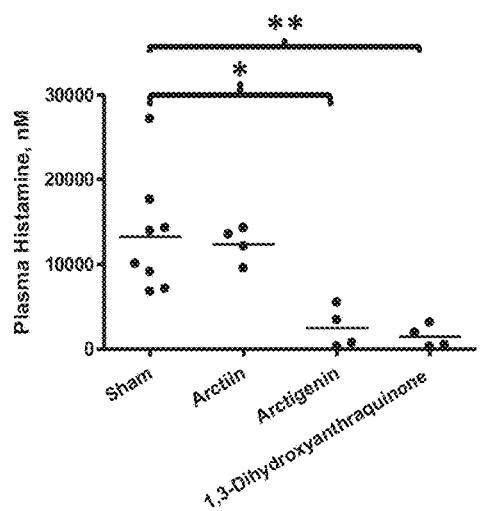

FIGS. 37A-37E show comparison of the bioactivities of compounds arctiin, arctigenin and 1,3-dihydroxyanthraquinone, on mouse model of peanut allergy. Compared to the other compounds, 1,3-dihydroxyanthraquinone shows the most potency on the inhibition of peanut-specific-IgE and plasma histamine level, lowering symptom scores, and increasing body temperature. FIG. 37A. In vivo experimental protocol; FIG. 37B. Peanut specific-IgE level in the serum of peanut-allergic mice; FIG. 37C. Peanut-induced anaphylactic symptoms score; FIG. 37D. The core body temperatures during challenge. Body temperatures were measured 30 minutes after completion of oral challenge; FIG. 37E. The histamine level in plasma after completion of challenge. *, $p<0.05$; , $p<0.01$ (n≥3); *, $p<0.001$.

EXAMPLES

The present invention is further described by way of the following particular examples. However, the use of such examples is illustrative only and is not intended to limit the scope or meaning of this invention or of any exemplified term. Nor is the invention limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

Example 1

Methods
Materials
FAHF-2, B-FAHF-2 and Individual Herb Extracts

In order to identify individual pharmaceutically active compounds effective for modulating food allergy and other allergen mediated physiological responses, we used as our starting material FAHF-2 and B-FAHF-2. FAHF-2 and B-FAHF-2 are mixtures of herbs used in traditional Chinese medicine and have been previously shown effective at treating food allergies, and in particular, peanut allergies. See U.S. Pat. No. 7,820,175 hereby incorporated by reference.

As previously described, FAHF-2 is a dried aqueous extract of 9 herbs purified with ethanol. It is produced in a GMP-certified facility (Xiyuan Chinese Medicine Research and Pharmaceutical Manufacturer, Beijing China) and stored at room temperature. All herbs used for manufacture were of Chinese origin. The quality of the raw herbs was established according to the standards of the Pharmacopoeia of People's Republic of China as previous described. Based on organoleptic and microscopic examination, raw herbs used in FAHF-2 were identified as follows: fruits of *Prunus mume* (*P. mume*), skin of the fruits of *Zanthoxylum schinifolium* (*Z. schinifolium*), roots of *Angelica sinensis* (*A. sinensis*), rhizome of *Zingiber officinalis* (*Z. offcinalis*), twigs of *Cinnamomum cassia* (*C. cassia*), bark of *Phellodendron chinensis* (*P. chinensis*), rhizome of *Coptis chinensis* (*C. chinensis*), roots of *Panax ginseng* (*P. ginseng*) and fruiting body of *Ganoderma lucidum* (*G. lucidum*). The botanical information for the individual herbs, including geographical location, harvest season, pre-processing, heavy metal and pesticide residues, and quality control methods, have been published previously. The manufacturing process has been described in our previous publication. Briefly, the raw herbs were cut into small pieces and soaked in water for 30 minutes, then boiled for 2 hours. Decoctions were collected and concentrated under vacuum.

Figure 29:
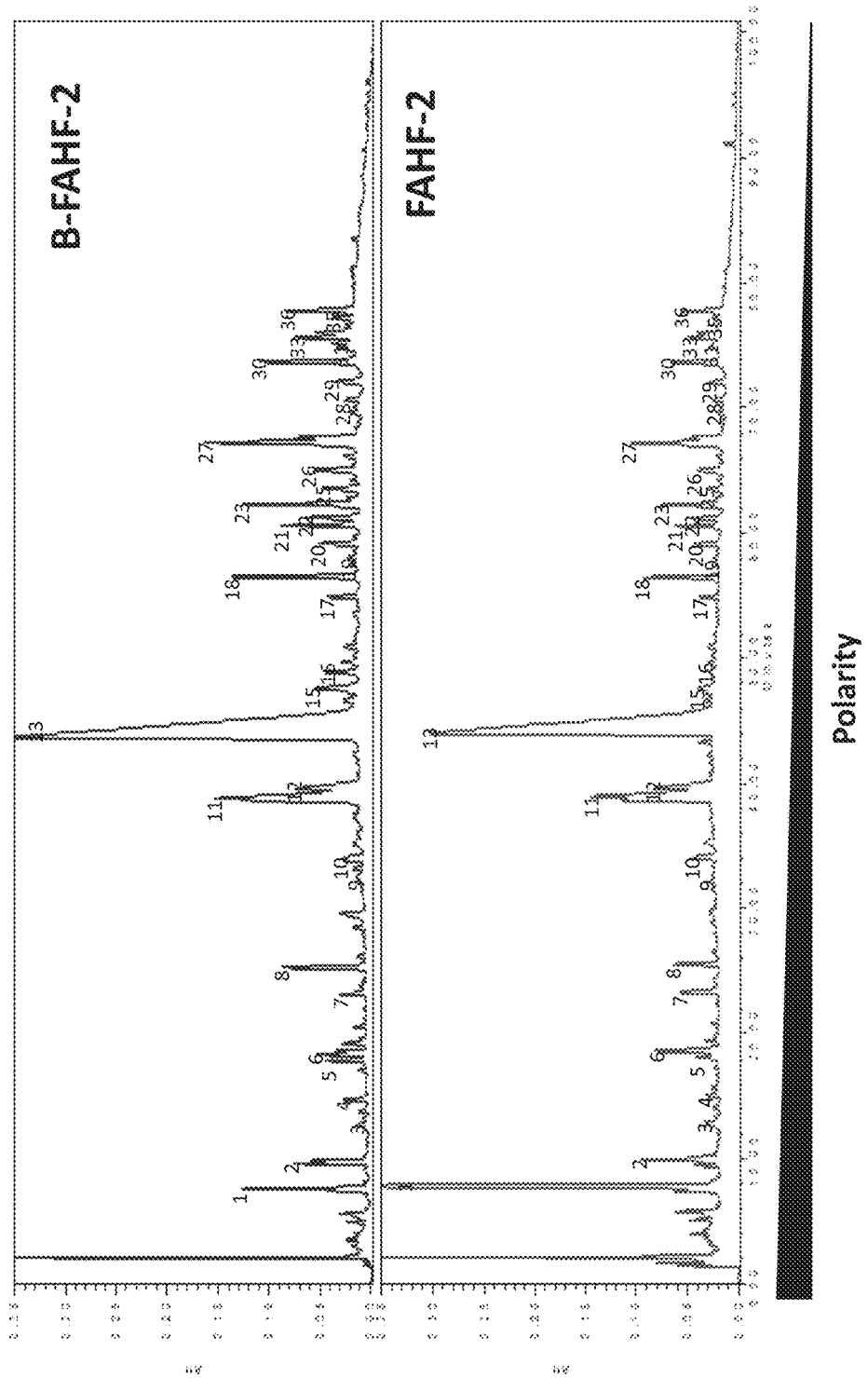
FIG. 29. HPLC fingerprints of FAHF-2 and B-FAHF-2. Thirty-six peaks were detected.

B-FAHF-2 is a concentrated form of FAHF-2 produced by butanol purification of FAHF-2 as previously described. HPLC fingerprints of FAHF-2, B-FAHF-2 and individual herb extracts were generated (FIG. 29) for the purpose of product quality control according to the guidelines issued by the US FDA as previously described.

Isolation, Purification, Identification and Quantification of Active Compounds from *P. chinensis*

Figure 30A:
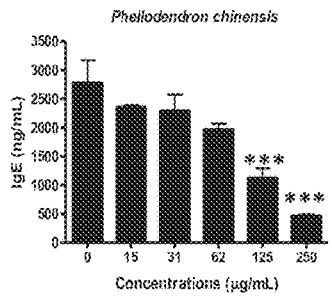
FIGS. 30A-30J. Dose-dependent studies of individual herbal constituents in FAHF-2 formula on IgE production by U266 cells. IgE levels produced from U266 cells treated with increasing concentrations of compounds from *P. chinensis* (FIG. 30A), *C. chinensis* (FIG. 30B), *G. lucidum* (FIG. 30C), *P. mume* (FIG. 30D), *Z. oficinalis* (FIG. 30E), *C. cassia* (FIG. 30F), *A. sinensis* (FIG. 30F), and *Z. schifolium* (FIG. 30G) were measured. In addition, the cell viabilities after *P. chinensis* (FIG. 30H), *C. chinensis* (FIG. 30I), and *G. lucidum* (FIG. 30J) were also measured. *, p<0.05; , p<0.01; *, p<0.001 (n≥3).
Figure 30B:
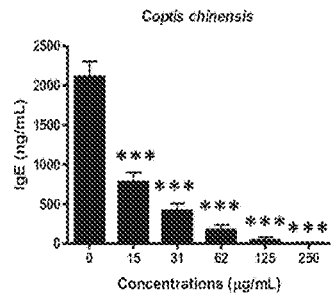
Figure 30C:
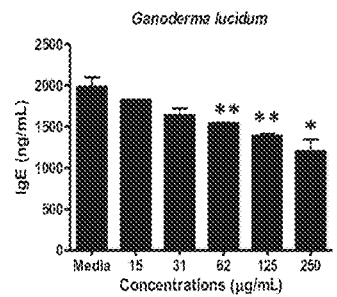
Figure 30D:
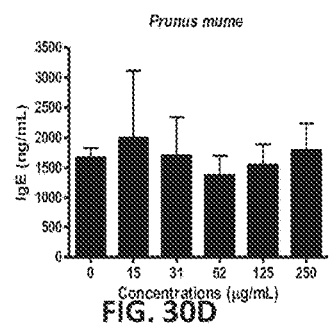
Figure 30E:
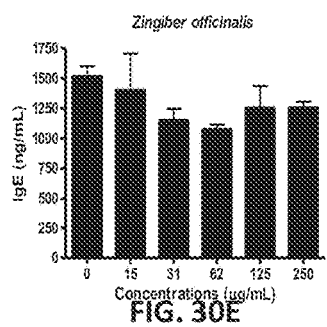
Figure 30F:
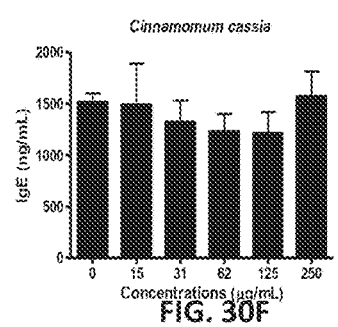
Figure 30G:
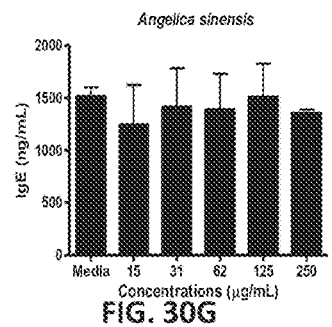
Figure 30H:
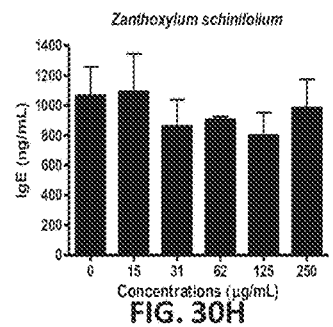
Figure 30I:
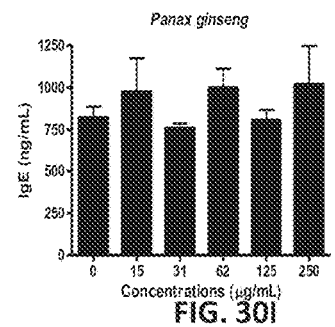
Figure 30J:
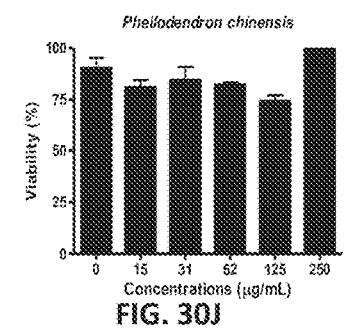
Figure 30K:
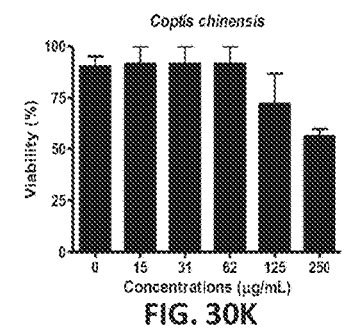
Figure 30L:
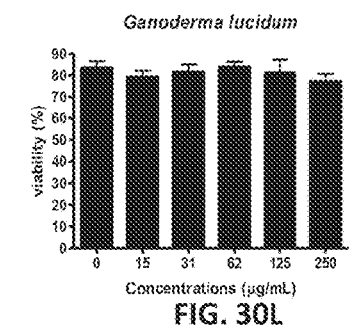

In testing the IgE inhibitory property of the individual herb constituents, 3 were found to exhibit significant anti-IgE effects (*P. chinensis*, rhizome of *C. chinensis*, and *G. lucidum*) (FIG. 30A, FIG. 30B, and FIG. 30C). As a first step in isolating and identifying active compounds from the effective herbs in FAHF-2, we focused on *P. chinensis* in light of cost effectiveness (It is 7.5 times and 3.8 times less expensive than the rhizome of *C. chinensis* and *G. lucidum*, respectively). We employed our previously established methods to isolate and purify the active compounds. In brief, 200 g of dried aqueous extract of *P. chinensis* was dissolved in 4 L of distilled water and extracted with an equal volume of chloroform (4 L) (FIG. 1). The chloroform extract was further separated on the basis of the polarity of components using silica gel (Merck 230-400mesh, Sigma, Germany), eluted with a dichloromethane-methanol (DM) mixture at ratio 49:1, 19:1, 9:1, and 1:1 sequentially. On the basis of thin layer chromatography (TLC) and HPLC profiles, collections that contained the same peaks were combined to yield 4 major sub-fractions (F) designated DMF-A, B, C, and D. DMF-A and DMF-C contain simple major peaks compared to DMF-B and DMF-D, and were the focus of further isolation and purification in this study. DMF-A (1.2 g) was further separated using silica gel chromatography with a mobile phase of dichloromethane-ethyl acetate mixture at different ratio from 19:1, 9:1, and 5:1. One compound was re-crystallized from 19:1 dichloromethane-ethyl acetate eluent and named DMF-A1 (45 mg). DMF-C (3.6 g) was further separated/purified using a sephadex LH20 column with methanol as the solvent, resulting in a pure compound named as DMF-C1 (232 mg). Both compounds were characterized by liquid chromatography mass spectrometry (LC-MS) and compared to standard compounds and 1H and 13C NMR spectroscopy.

Human U266 Myeloma Cell Culture

The IgE producing human U266 myeloma cell line (American Type Culture Collection; Rockville, Md.) has been used for screening pharmaceutical agents for IgE inhibitory effects, and thus this cell line was used to test the potential IgE inhibitory effects of herb extracts and purified compounds. Cells were cultured at 37° C. under 5% $CO_2$ in complete media containing RPMI 1640 medium supplemented, 10% FBS, 1 mM sodium pyruvate, 1×10-5 M β-ME and 0.5% penicillin-streptomycin. Cells were grown at an initial concentration of 2×105 cells/mL. FAHF-2 and B-FAHF-2, individual herb extracts and isolated compounds at different concentrations were added at day 0. Supernatants were harvested after 6 days culture, and IgE levels were determined by using an ELISA Kit (Mabtech Inc, OH). In each experiment, we run duplicate ELISA. In vitro experiments were repeated at least 3 times.

Study Participants, PBMC Isolation and Culture

Blood samples were obtained from 25 pediatric subjects with physician diagnosed food allergy (6-17 years old; Male/Female: 20/5). Individuals with physician diagnosed food allergy as documented by physician-determined history of allergic reactions to peanut, or/and tree nut, or/and fish and by a positive skin test result (mean wheal diameter ≥3 mm greater than the mean of the saline control) and/or food allergen specific IgE level (peanut, tree nut or fish specific IgE≥0.7 kU/L) were eligible for the study. This study was approved by the Mount Sinai Institutional Review Board. Written informed consent was obtained before enrollment.

PBMCs were isolated by Ficoll Hypaque (Pharmacia, Piscataway, N.J.) using density gradient centrifugation at 1800 RPM for 30 minutes, and washed 3 times in PBS. To determine the optimal stimulation of IgE production by PBMCs, PBMCs at 1.5×106 cells/mL were suspended in complete RPMI medium (200 μM L-glutamine, 1% penicillin/streptomycin, 25 mM HEPES, 10% heat inactivated fetal calf serum), and co-stimulated with human recombinant IL-4 (rIL-4) at 0.01 and 0.1 μg/mL (R&D Systems, Minneapolis, Minn., USA) and anti-CD40 monoclonal antibody (mAb) at 10, 100 μg/mL (R&D) for 10 and 14 days. At the end of incubation, the supernatants were collected and IgE levels were analyzed using ELISA kit (Mabtech Inc, OH). Since PBMCs stimulated with 100 ng/mL rIL-4 and 1 μg/mL anti-CD40 mAb produced the highest level of IgE, we used this culture condition for the subsequent studies. PBMCs were stimulated with 100 ng/mL rIL-4 and 1 μg/mL anti-CD40 mAb and cultured in the presence or absence of 20 μg/mL of the two purified compounds for 10 days for screening active compounds, and at different concentrations (0.15, 0.31, 0.62, 1.25, 2.5, 5, 10 μg/mL) to examine dose responses for the effective compounds. IgE level was evaluated using ELISA. The percentage of IgE inhibition was calculated as follows: Inhibition (%)=(IgE concentration in treated sample)/(IgE concentration in untreated sample)×100. In some cases if enough PBMCs were obtained, aliquots of PBMCs prepared from the same individuals were used for different experiments.

Cell Viability:

Cell viability was evaluated using a trypan blue exclusion as previously described. Briefly, a 10 μl of cells suspension from each culture was mixed with equal volume of trypan blue dye. The mixture was loaded into a hemocytometer and cells were counted under a microscope. The percentage of viable cells was calculated as follows: Viable cells (%)= (total number of viable cells)/(total number of cells)×100.

Real Time Polymerase Chain Reaction (RT-PCR)

Quantitative real time PCR was used to detect the epsilon germline transcription. Human PBMC cells (1.5×106 cells/mL) were co-incubated with DMF-C1 compound (10 μg/mL) at 37° C. under 5% CO2 for 4 days. Cells were then harvested and total RNA was isolated using Trizol reagent (Gibco BRL, Rockville, Md.) following the manufacturer's instructions. The RNA concentrations were then quantified by triplicate optical density (OD) readings (Bio-Rad SmartSpect 3000; Bio-Rad, Hercules, Calif.). The reverse transcription was performed to get the cDNA using ImProm-II™ Reverse Transcriptase (Promega Corporation, Madison, Wis.) as described by the manufacturer's instructions. The RT-PCR amplification was performed using Maxima™ SYBR Green qPCR Master Mix (2×) kit (Fisher Scientific, Pittsburgh, Pa.) with epsilon germline primers or GAPDH primers. The primer sequences were listed as εGLT forward: 5'-CACATCCACAGGCACCAAAT-3'; εGLT reverse: 5'-ATCACCGGCTCCGGGAAGTA-3'; GAPDH-forward: 5'-GAGGCAGGGATGATGTTCTG-3'; GAPDH-reverse: 5'-CAGCCTCAAGATCATCAGCA-3'; STAT3-forward: 5'-ACCTGCAGCAATACCATTGAC-3'; STAT3-reverse: 5'-AAGGTGAGGGACTCAAACTGC-3'; T-bet-forward: 5'-GATGCGCCAGGAAGTTTCAT-3'; T-bet-reverse: 5'-GCACAATCATCTGGGTCACATT-3'; IFN-γ-forward: 5'-AAAGATGACCAGAGCATCCA-3'; IFN-γ-reverse: 5'-TTGCGTTGGACATTCAAGTC-3'; IL-10-forward: 5'-CTGCCTAACATGCTTCGAGA-3'; IL-10-reverse: 5'-TGGCAACCCAGGTAACCCTTA-3'. IL-5-forward. 5'-GCCATGAGGATGCTTC TGCA-3'; IL-5-reverse: 5'-GAATCCTCAGAGTCTCATTGGCTATC-3'. All primers were synthesized by Sigma-Aldrich Corporation (St. Louis, Mo.).

In-Cell Western Blot:

PBMCs (1×105 cells/mL) were cultured with or without DMF-C1 (10 μg/mL) and stimulated with or without rIL-4 (100 ng/mL) and anti-CD40 (1 μg/mL) mAb for 10 days. In-Cell Western Assay (Li-Cor, Lincoln, Nebr.) was performed following the manufacturer's instructions. In brief, cells were incubated with antibodies against phosphorylated-IκBα (p-IκBα; Cell Signaling) and β-actin (Santa Cruz Biotechnology) overnight. After washing with 0.1% Tween PBS buffer, secondary antibodies IRDye800CW donkey anti-goat and IRDye680 donkey anti-rabbit (LI-Cor) were added and incubated at room temperature for 1 hour in the dark. Plates were scanned and analyzed with Odyssey CLx Infrared Imaging System.

Statistics:

One way ANOVA (analysis of variance) was performed followed by Bonferroni correction for all pairwise comparisons. For skewed data, the differences between the groups were performed by one way ANOVA on rank followed by Donne's method for all pairwise comparisons. P-values were determined by a two-sided calculation. A P value ≤0.05 was considered as statistically significant. All statistical analyses were performed using Sigma Stat 3.5 (Systat Software Inc., Chicago, Ill.).

Results

FAHF-2 and B-FAHF-2 Inhibited IgE Production by U266 Cells

Figure 25A:
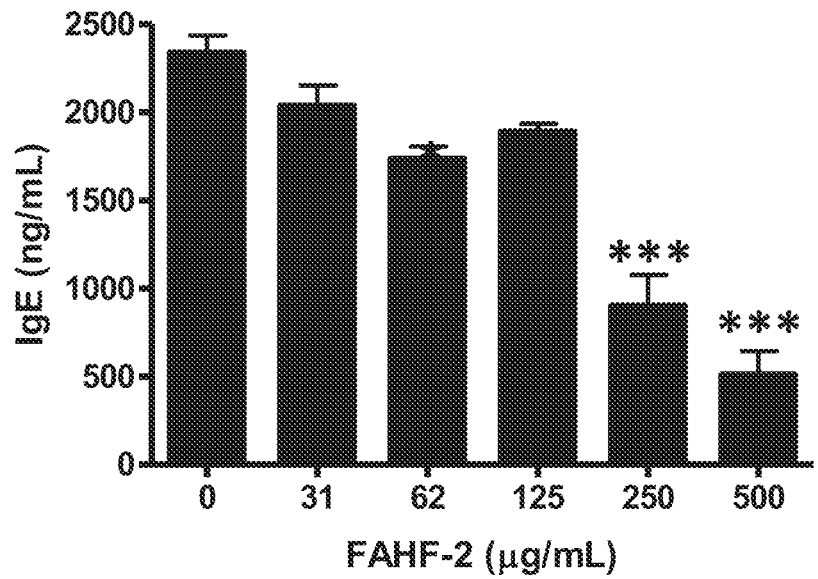
FIGS. 25A-B. Dose-dependent inhibitory effect of herbal formulas FAHF-2 and B-FAHF-2 on IgE production by U266 cells.
Figure 25B:
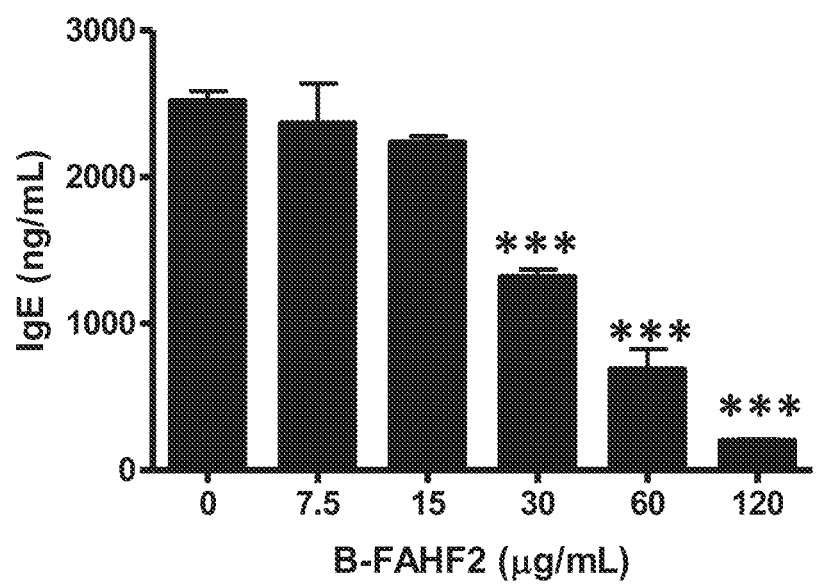

In order to evaluate the effects of FAHF-2 on IgE production, U266 cells were incubated with FAHF-2 at different concentrations (0, 31, 62, 125, 250 and 500 μg/mL). FAHF-2 inhibited IgE production in a dose-dependent manner (FIG. 25A), with 125 μg/mL and 500 μg/mL of FAHF-2 significantly inhibiting IgE production (p<0.001). At the highest concentration, 500 μg/mL, inhibition reached 78.1%.

Figure 31A:
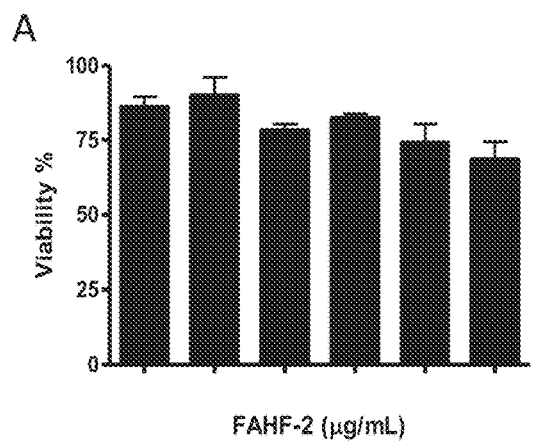
FIG. 31A-31D. Cell viability test for FAHF-2 (FIG. 31A), B-FAHF-2 (FIG. 31B), Berberine (FIG. 31C), and Limonin (FIG. 31D).
Figure 31B:
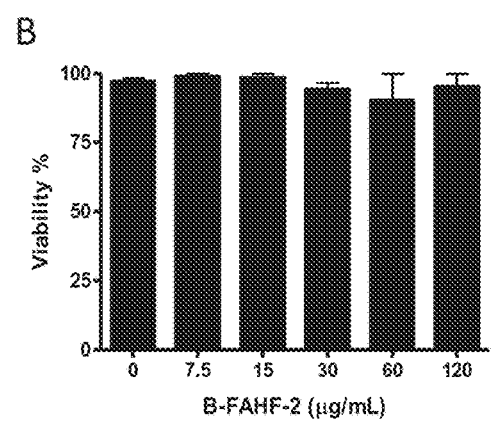

Previous results showed that the yield of butanol extraction of FAHF-2 is 22.37±1.55%. Therefore, B-FAHF-2 was tested on U266 cells at concentrations 0, 7.5, 15, 30, 60, 120 μg/mL equivalent to that of FAHF-2 based on the yield value. Similar to FAHF-2, B-FAHF-2 inhibited IgE production by U266 cells in a dose-dependent manner (FIG. 1B). Suppression of IgE by B-FAHF-2 reached statistical significance at 30, 60 and 120 μg/mL (p<0.001) and maximally inhibited IgE production (92.0%) at the highest concentration, 120 μg/mL. The half-maximal inhibitory concentration (IC50) was 9.2 fold lower for B-FAHF-2 than FAHF-2 (34.44 μg/mL vs. 313.6 μg/mL). Trypan blue exclusion assays showed that FAHF-2 and B-FAHF-2 did not affect cell viability at the concentrations used (FIGS. 31A and 31B).

These data demonstrate that B-FAHF-2, comprised of less polar components, is more potent than FAHF-2 at inhibiting IgE production. This finding is consistent with HPLC fingerprint features of B-FAHF-2 and FAHF-2. Although 36 peaks were detected in both FAHF-2 and B-FAHF-2 (FIG. 29), B-FAHF-2 showed stronger intensity for the majority of less-polar and non-polar peaks even at a ~5 fold lower HPLC loading concentration (40 mg/mL) than FAHF-2 (198 mg/mL). Peak 1 corresponds to polar constituent. Its intensity in B-FAHF-2 extract was reduced by 94% compared to that in FAHF-2 extract. B-FAHF-2 was more potent than FAHF-2 in suppressing IgE production due to the more concentrated less-to-non-polar compounds.

Two Compounds from *P. chinensis* were Isolated and Characterized as Limonin and Berberine

*P. chinensis* aqueous extracts were further extracted and fractionated, and two compounds DMF-A1 (compound 1) and DMF-C1 (compound 2) were purified. The purity of each compound was >98% as determined by analytical HPLC. The structures of compounds 1 and 2 were identified using LC-MS (FIGS. 2A-2D) and $^1$H and $^{13}$C NMR spectroscopy (Table 1). Mass spectra data of compound 1 showed a significant [M+H]+ ion peak at m/z 471. Data of compound 2 showed a [M+H]+ peak at m/z 336 (FIG. 2A and FIG. 2B). The molecular weights (MW) of compounds 1 and 2 were then determined to be 470 g/mol and 336 g/mol respectively. The $^1$H NMR and $^{13}$C NMR data of compounds 1 and 2 are consistent with previously reported data of limonin and berberine chloride. Thus, based on the MS and NMR data, compound 1 and 2 were identified as limonin and berberine, respectively.

TABLE 1

$^1$H and $^{13}$C NMR of compound 1

| position | δ H (DMSO-d$_8$) | δ C (chloroform-D) |
|---|---|---|
| 1 | 4.11 (1H, dd, J = 16.8, 3 Hz) | 79.4 |
| 2 | 2.61 (1H, dd, J = 17.1, 4.2 Hz), 3.10 (1H, dd, J = 15, 5.4 Hz) | 35.9 |
| 3 | | 169.3 |
| 4 | | 80.5 |
| 5 | 2.26 (1H, dd, J = 14.7, 3 Hz) | 60.7 |
| 6 | 2.42 (1H, dd, J = 14.7, 3 Hz), 2.76 (1H, d, J = 16.2 Hz) | 36.6 |
| 7 | | 206.3 |
| 8 | | 51.5 |
| 9 | 2.51 (1H, m) | 48.3 |
| 10 | | 46.1 |
| 11 | 1.90 (1H, m), | 19.1 |
| 12 | 1.22 (1H, m), 1.75 (1H, m) | 31.0 |
| 13 | | 38.2 |
| 14 | | 65.9 |
| 15 | 4.08 (1H, s) | 54.1 |
| 16 | | 166.8 |
| 17 | 5.46 (1H, s) | 79.4 |
| 18 | 1.01 (3H, s) | 20.9 |
| 19 | 4.47 (1H, d, J = 12.9 Hz), 4.90 (1H, d, J = 13.1 Hz) | 65.6 |
| 20 | 6.49 (1H, d, J = 1.02 Hz) | 109.9 |
| 21 | | 120.2 |
| 22 | 7.70 (1H, br.s) | 141.3 |
| 23 | 7.64 (1H, t, J = 1.74 Hz) | 143.4 |
| 24 | 1.09 (3H, s) | 21.6 |
| 25 | 1.17 (5H, s) | 30.4 |
| 26 | 0.98 (3H, s) | 17.8 |

Figure 31C:
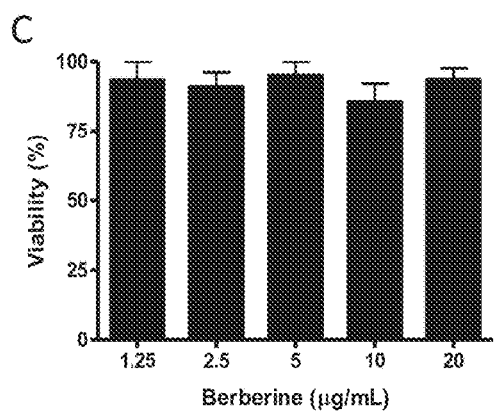
Figure 31D:
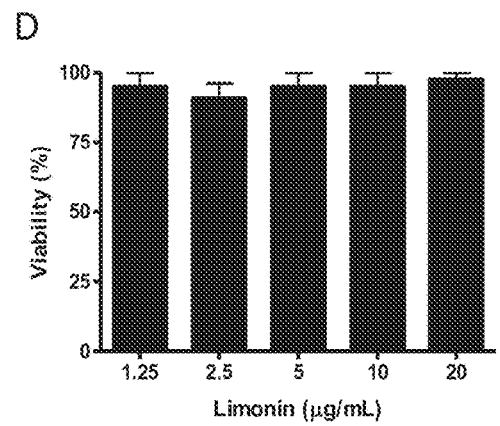

Berberine was a More Effective Inhibitor of IgE Production by U266 Cell Line than Limonin The bioactivities were analyzed in vitro on U266 cells in the presence of berberine or limonin at different concentrations. As shown in FIG. 3A, berberine inhibited IgE production in a dose-dependent manner, reaching 94.6% inhibition at 20 μg/mL. The IC50 value was 3.95 μg/mL (FIG. 3B). Limonin showed mild reduction of IgE production by U266 cells. The greatest inhibitory effect of limonin was 35.1%, observed at a concentration of 20 μg/mL (p<0.01) (FIG. 3C). Unlike berberine, no dose dependent effect was observed for limonin. Cell viability assays showed no toxicity at any concentration tested (FIG. 31C-D).

Figure 26:
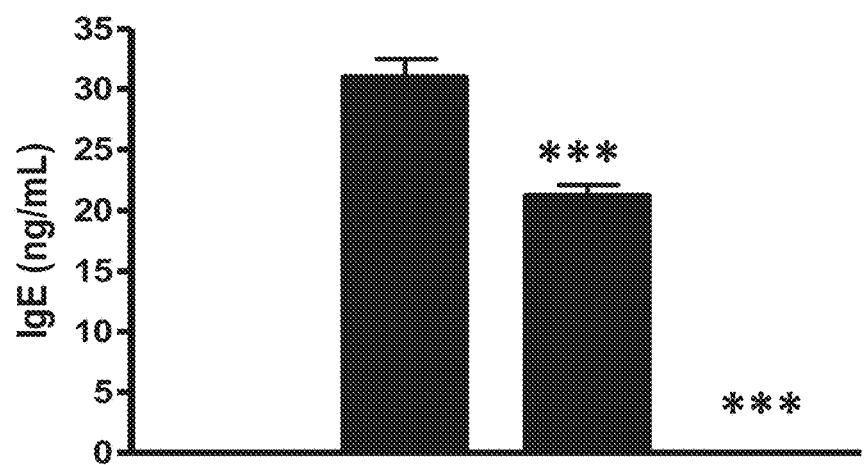
FIG. 26. Inhibitory effect of berberine and limonin on IgE production by human PBMCs. To identify active compounds, PBMCs (1.5×106 cells/mL) from food allergic patients were collected and co-stimulated with human rIL-4 (100 ng/mL) and anti-CD40 mAb (1 µg/mL) in the presence of different compounds at 20 µg/mL for 10 days. IgE levels were determined by ELISA. ***, p<0.001 (n=4).
Figure 32:
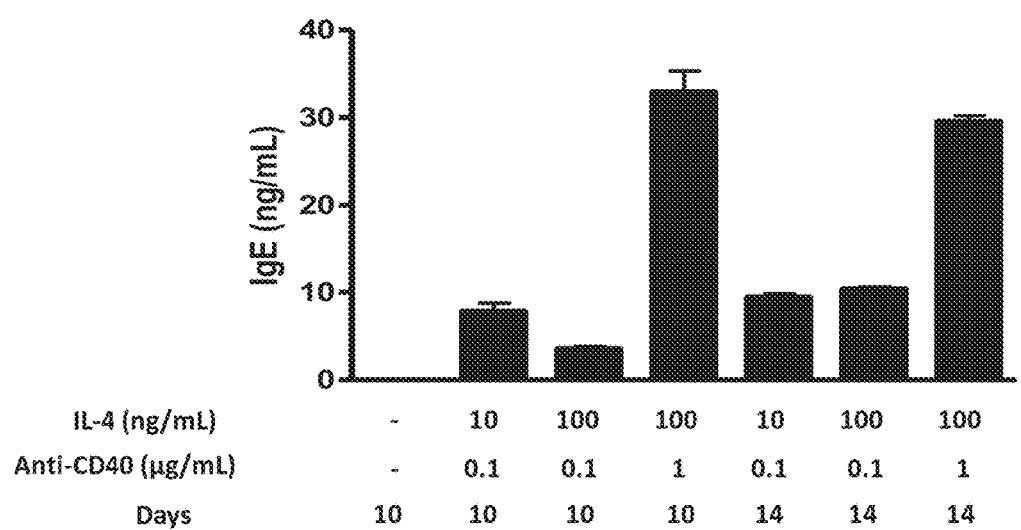
FIG. 32: Dose and timing effects of IL-4 and anti-CD40 mAb stimulation on IgE production by human PBMCs.

Berberine was More Effective than Limonin in Suppressing IgE Production by PBMCs from Patients with Food Allergies To further examine the effect of berberine and limonin on IgE production, PBMCs from food allergic individuals were used. To optimize culture conditions, we tested different concentrations of anti-CD40 antibodies (0.1 and 1 μg/mL) and rIL-4 (10 and 100 ng/mL) and culture durations (10 and 14 days). The results showed that human PBMCs generated the highest concentration of IgE when co-incubated with 100 ng/mL rIL-4 and 1 μg/mL anti-CD40 mAb for 10 days (FIG. 32). Using these parameters, we assessed the inhibitory effects of berberine and limonin. Berberine completely inhibited the IgE production by human PBMCs at 20 μg/mL, whereas limonin produced 33.9% inhibition at the same concentration (FIG. 26). Dose dependent effects of berberine on IgE production by PBMCs was further investigated (FIG. 4A). Significant inhibition starting at 0.62 μg/mL (80.67±9.24% inhibition percentage) was observed. IC50 value was calculated to be 0.20 μg/mL. Cell viability was not compromised at any dose of berberine tested (FIG. 4B). We assessed potential apoptosis using flow cytometry and annexin V. After 2 days incubation with 10 μg/ml of berberine, PBMCs were incubated with CD19 antibody and stained with annexin V. The result showed about 16% stained B cells in both berberine treated and untreated cells. No significant difference was observed. We have included these data in FIG. 33.

Berberine Inhibited ε-Germline Transcription (εGLT) by PBMCs

Epsilon germline transcription is an important step for IgE isotype switching. To test whether the mechanism of the inhibition effect of berberine on IgE production is through regulation of the epsilon germline, we analyzed the mRNA expression of εGLT by RT-PCR. The mRNA expression of εGLT was detected in 7 patients' PBMCs. RT-PCR results demonstrated that the relative mRNA expression of εGLT was significantly inhibited when co-incubated with berberine (FIG. 5) at a concentration of 10 μg/mL as compared to untreated cultures ($p<0.001$).

Berberine Inhibited Phosphorylated IκBα

NF-κB signaling pathways are involved in B cell activation. It is possible that the NF-κB signaling pathway is involved in upstream mechanisms underlying berberine inhibition of IgE synthesis. NF-κB is inactive when reacted with the inhibitory IκB protein. Phosphorylation of IκB results the exposure of the nuclear localization signals on NF-κB. This eventually leads to the translocation of NF-κB to the nucleus, and activation of the Iε promoter, and enhance the εGLT transcripts. We therefore determined phosphorylated IκBα levels in berberine treated human PBMCs. Phosphorylated IκBα levels were significantly increased after stimulation with IL-4 and anti-CD40 antibody ($p<0.005$). Berberine treatment at 10 μg/mL significantly suppressed phosphorylated IκBα levels compared with the non-treated cells ($p<0.05$) (FIG. 6).

Berberine Increased STAT3 and T-Bet Expression

In order to further explore the mechanism of berberine's effects on PBMCs, we performed real-time PCR to analyze gene expression levels of STAT3, T-bet, IFN-γ, Foxp3, GATA-3, IL-10, and IL-5 (FIG. 7A through FIG. 7G). 10 μg/mL berberine treated cells significantly increased mRNA expression of T-bet ($p<0.001$) (FIG. 7B) and STAT-3 ($p<0.005$) (FIG. 7A) in stimulated PBMCs. The mRNA levels of IFN-γ (FIG. 7C), Foxp3 (FIG. 7D), IL-10 (FIG. 7F) showed a trend of increase. No significant change on GATA-3 expression (FIG. 7E) was observed. The mRNA level of IL-5, were significantly decreased (FIG. 7G) ($p<0.05$).

Discussion

In previous studies, FAHF-2, has demonstrated remarkable efficacy at protecting against peanut-induced anaphylaxis in a murine model of peanut allergy. However, the mechanisms underlying these immune changes are unclear as are the relative contributions of each individual herb or compounds within herbs to these observed findings. In this study, we aimed to identify the herbs that mediate suppression of IgE production and identify the relevant active compounds.

Medicinal herbals contain medicinal and non-medicinal ingredients. Previous studies have demonstrated that several classes of natural compounds, including alkaloids, flavonoids and triterpenoids, may have properties of anti-allergy effects. These compounds are primarily non-polar or less polar small molecules (<1000 Dalton). We previously showed that butanol purification of FAHF-2 concentrates the non-polar and less polar compounds, increasing the potency of the formula.

In this first attempt to isolate active compounds in B-FAHF-2, we focused on *P. chinensis*, one of the three individual herbs that showed significant anti-IgE effects. Following chloroform fractionation and column chromatography isolation/purification, two compounds were isolated and were identified as berberine and limonin by LC-MS and NMR.

Berberine is a plant alkaloid that has been widely used in both Chinese and Ayurvedic medicine primarily to treat intestinal symptoms (diarrhea) given its antimicrobial and antiprotozoal effects. Additional pharmacologic actions reported include anticancer activity, cardioprotective effects as well as anti-inflammatory effects, specifically suppression of proinflammatory cytokines such as tumor necrosis factor (TNF)-alpha. However, to our knowledge this is the first study to assess its effects on IgE production directly. We found that berberine is effective in suppressing IgE production by human U266 cells without any signs of cytotoxicity with an IC50 value of 3.95 μg/mL. The IgE inhibitory effect of berberine was further examined using PBMCs from pediatric subjects with food allergies. B cell activation requires at least two signals, CD40 L from T cells (signal 1) and Th2 cytokines (signal 2). Previous studies showed that anti-CD40 antibodies and IL-4 were able to induce IgE production by PBMCs from subjects with house dust mite allergies. However, the concentration of anti-CD40 and IL-4 concentration used varied between the studies. In this study, we optimized our culture conditions and showed that anti-CD40 (1 μg/mL) and IL-4 (100 ng/mL) induced IgE production by PBMC following 10 days culture, and berberine markedly inhibited this process. Further dose dependent study showed that berberine exhibits a potent IgE inhibitory effect; the inhibition reached statistical significance at as low as 0.62 μg/mL. The IC50 value was calculated to be 0.20 g/mL. Importantly, we demonstrated that berberine also exhibits a high safety profile in PBMCs as no signs of cytotoxity (either cell death or apoptosis) were observed at the concentrations up to 10 μg/mL, well above IC50 concentration. Berberine did not cause apoptosis at highest concentration tested demonstrating a high safety profiles in PBMCs.

IgE production requires class switch recombination (CSR). In general, isotype switching is regulated at the level of germline transcription of the constant heavy chain genes. Since berberine suppression of IgE production is not due to cytoxicty, as a first attempt to understand the mechanisms underlying berberine inhibition of IgE production, we assessed the relative expression of εGLT in berberine treated and control cells. The RT-PCR results showed that berberine significantly inhibited εGLT transcription. This suggests that berberine inhibition of anti-CD40 and IL-4 induced IgE production is due, at least in part, to alteration of F germline transcription. Although there are no direct studies on whether and how berberine suppression of IgE synthesis, some studies showed that berberine suppresses NF-κB signaling pathways, which is associated with its anti-cancer and anti-inflammatory and anti-diabetic actions. Activation of NF-κB signaling pathways is one of the upstream of mechanisms underlying B cell activation and εGLT expression. We therefore performed the In-Cell Western experiment to analyze the level of p-IκBα, the marker of activation of NF-κB signaling, expressed in PBMCs. Our results showed that berberine treatment significantly inhibited p-IκBα levels.

In contrast to εGLT, STAT3, Foxp-3 and T-bet are transcription factors that negatively regulate IgE synthesis. Deficiency in either of this gene has been reported to be associated with strikingly elevated IgE levels in patients. We found that STAT3 and T-bet gene expression was significantly increased, and Foxp 3 gene expression showed trend of increase. In addition, we found a trend of up-regulation of IL-10, IFN-γ, and a significant suppression of IL-5 gene expression (FIG. 7G). It is suggested that berberine affects poly A RNA in cancer cells, but other study showed that berberine stabilize poly A RNA to assist in neurons survival during cerebral ischemia injury. The diffident findings seem to be depending on different type of cells. We for the first time investigated the anti-IgE production effect of berberine on human PBMCs. Our findings suggest that berberine suppression of IgE synthesis by PBMCs is not due to overall suppression of gene transcription and involved in multiple regulatory mechanisms. However, further studies are needed to understand the precise mechanisms.

We also demonstrate that limonin, a tetranortriterpenoid, has some inhibitory effects on IgE production by a human B cell line and by PBMCs, but it was less potent than berberine. Limonin is responsible for the bitterness of citrus fruits such as lemon, grapefruit and orange, and is often removed during the production of fruit juices to improve the taste. Our study is the first to show that limonin suppressed IgE production in vitro, and suggests that this compound may be beneficial for allergies.

In addition to *P. chinensis*, several other plants including *C. chinensis* also contain berberine. Therefore, berberine may also be an important active compound in *C. chinensis* that is responsible for *C. chinensis'* IgE inhibitory effect. Although we identified berberine and limonin isolated from *P. chinensis* as IgE inhibitory compounds, berberine being most effective, other compounds from *P. chinensis* and *C. chinensis* as well as *G. lucidum* may also contribute to suppression of IgE production.

In summary, we, for the first time, demonstrate that berberine and limonin exhibit suppressive effects on IgE production by a human B cell line and PBMCs from pediatric food allergic subjects in a non-toxic manner. Berberine also exhibits inhibitory effects on εGLT expression by PBMCs. This study identifies some of the active molecules contained in FAHF-2 and B-FAHF-2 and provides insights into potential mechanisms underlying the effects of these formulas in treating IgE mediated food allergy. Further studies are needed to identify additional active molecules that are mediating the favorable immune-modulatory effects of FAHF-2/B-FAHF-2 and to understand the mechanisms by which these molecules are exerting their effects.

Example 2

Figure 27:
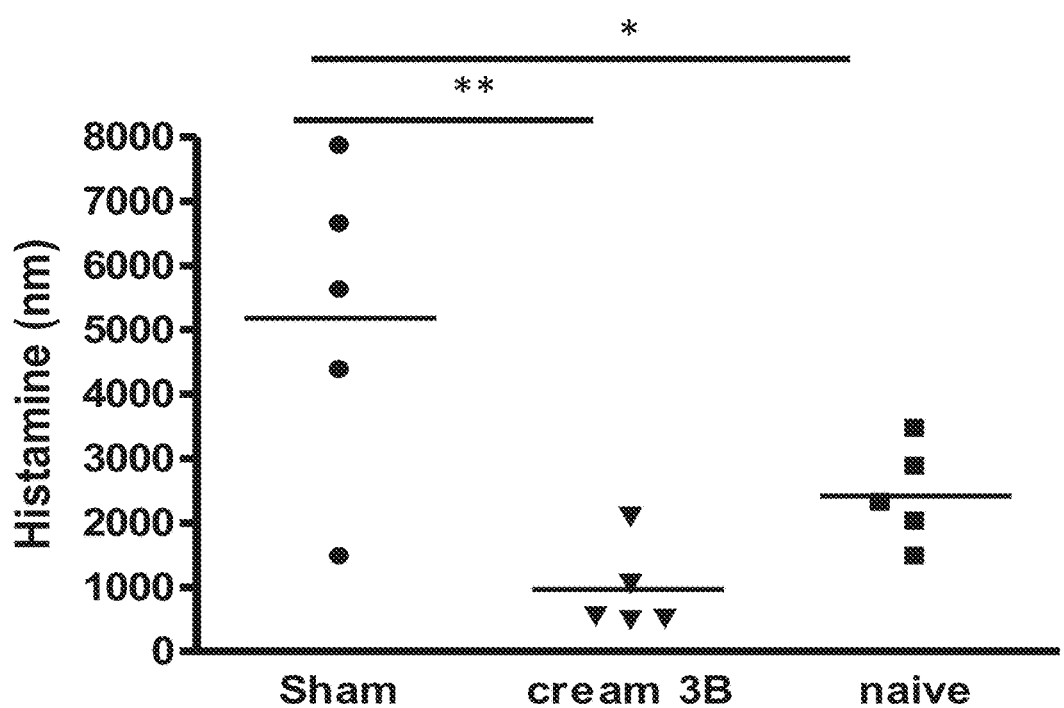
FIG. 27. Berberine cream 3B significantly inhibited the histamine release after peanut challenge in the mouse model. Histamine in plasma was collected 30 minutes after challenge. Histamine level was evaluated using ELISA. *, p<0.05; **, p<0.01.

Berberine cream 3B significantly inhibited the histamine release after peanut challenge in the mouse model (FIG. 27).

Figure 28:
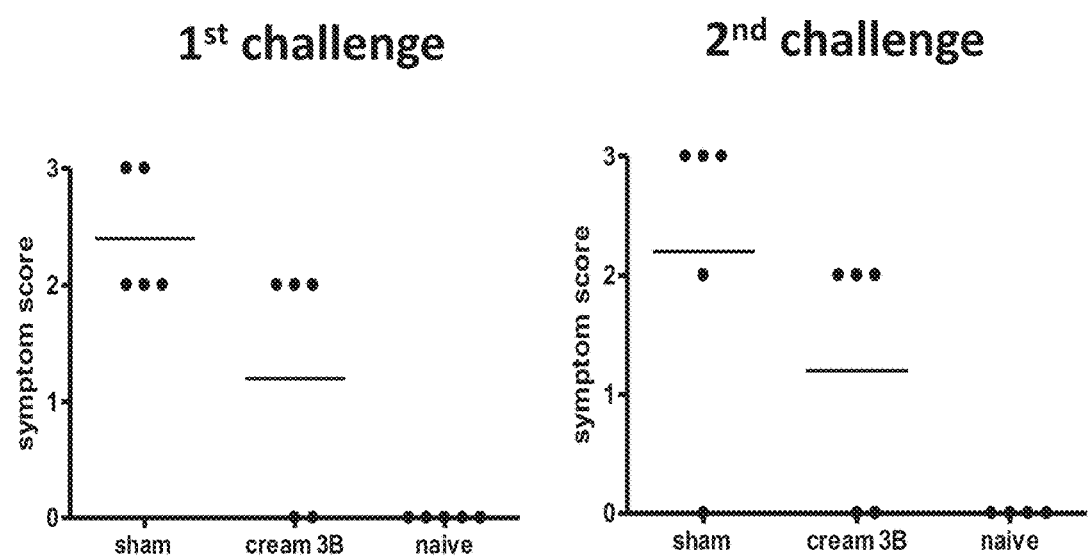
FIG. 28. Berberine cream 3B suppressed anaphylactic response. Berberine cream 3B treatment showed protection of peanut allergic mice from anaphylactic reaction. The berberine cream 3B treated mice showed lower anaphylaxis symptom score.

Berberine cream 3B suppressed the anaphylactic response. Berberine cream 3B treatment showed protection of peanut allergic mice from anaphylactic reaction. The berberine cream 3B treated mice showed lower anaphylaxis symptom score (FIG. 28).

Example 3

Methods
Berberine Uptake In Vitro and In Vivo Experiments:
Cell Culture:

Experiments were performed on 24 well plates for berberine uptake assay. CACO-2 cells were seeded in each well at the concentration of $1 \times 10^5$ cells/well. Cells were then allowed to grow to confluence and differentiation for 2 weeks in culture medium (DMEM+10% FBS, high glucose and sodium pyruvate and supplemented with 1% Essential Amino Acids). On the experiment day, cells were washed three times with pre-warmed HBSS and incubated with 1 ml warm HBSS for 30 minutes.

After conditioning with HBSS, cells were incubated at 37° C. with 50 µg/mL berberine with or without 250 µg/mL of nine different herbal medicines, fruits of *Prunus mume* (*P. mume*), skin of the fruits of *Zanthoxylum schinifolium* (*Z. schinifolium*), roots of *Angelica sinensis* (*A. sinensis*), rhizome of *Zingiber officinalis* (*Z. officinalis*), twigs of *Cinnamomum cassia* (*C. cassia*), bark of *Phellodendron chinensis* (*P. chinensis*), rhizome of *Coptis chinensis* (*C. chinensis*), roots of *Panax ginseng* (*P. ginseng*) and fruiting body of *Ganoderma lucidum* (*G. lucidum*). Control wells received 0, 50, 100 and 200 µg of berberine alone.

After 1 hour, cells were washed 3 times with ice-cold HBSS and scraped in 500 µl of ice cold HBSS and centrifuged. Cell pellets were resuspended into 100 µl of distilled water. Cells were lysed by 3 cycles of freeze-thaw process. 75 µL of each sample was analyzed for its berberine concentration by using LC-MS.

In Vivo Pharmacokinetics Study of Berberine Bioavailability:

C3H/Hej mice were purchased from Jackson laboratory (Bar Harbor, Me.) and maintained in the animal facility at Mount Sinai School of Medicine[39]. Standard guidelines for the care and use of animals were followed (Institute of Laboratory Animal Resources Commission of Life Sciences, 1996). In order to study the bioavailability, C3H/Hej mice were randomly separated into two groups. Mice were fasted for 12 h before the oral administration of berberine (2 mg) or berberine (2 mg)+*Angelica sinensis* (10 mg). Blood samples (100 µl) were collected from the facial vein at 1 hr after the administration. The serum of each blood sample was prepared and stored at –80° C. for further analysis.

Berberine Detection Using LC-MS

For Cacao-2 cell uptake assay, 75 L of lysed cells were mixed with 500 µL of acetonitrile and vortexed for 30 sec. The mixture was laid on ice for 15 mins with vortexing every 5 mins. The mixture was then centrifuged at 10000 rpm for 15 mins. The supernatant was concentrated under vacuum and reconstituted into 75 µL of acetonitrile.

For in vivo study of berberine bioavailability, 50 µL of each serum sample was mixed with 400 µL of acetonitrile and vortexed thoroughly. The mixture was then centrifuged at 1000 rpm for 15 mins. The supernatant was dried under vacuum and resuspended into 50 µL of acetonitrile.

All samples were analyzed using waters LC-MS system (Waters corp. MA) for berberine detection. Molecular weight was identified by LC-MS/TOF analysis in elctrospray (ESI) positive mode. The LCT premier TOF mass spectrometer (Waters Corporation, Milford, Mass.) was coupled to Waters Alliance 2695 HPLC system. 10 µL sample was. The mass range was from m/z 50 to 1000 in W optics mode. Nitrogen gas was used as nebulizer and desolvation gas with the flow rates 50 Uh and 600 L/h respectively. The source temperature was set to 120° C. The capillary voltage and the cone voltage were set to 3200 v and 25 v respectively.

In Vitro IgE Inhibition Experiment of Active Compounds from *Rubia cordifolia* L. and *Arctium lappa* L.:

Human U266 myeloma cells (American Type Culture Collection; Rockville, Md.) were cultured in complete medium (RPMI 1640 medium supplemented, 10% FBS, 1 mM sodium pyruvate, $1 \times 10^{-5}$ M β-ME and 0.5% penicillin-streptomycin) at 37° C. under 5% $CO_2$. Cells were grown at an initial concentration of $2 \times 10^5$ cells/mL with purpurin and alizarin from *Rubia cordifolia* L. at different concentrations (0.31, 0.62, 1.25, 2.5, 5 µg/mL), and with arctiin and arctigenin from *Arctium lappa* L. at different concentrations (1.25, 2.5, 5, 10, 201 µg/mL) for 6 days. The supernatants were harvested on day 6 for total IgE analysis using ELISA.

Effect of Arctiin, Arctigenin, and 1,3-Dihydroxyanthraquinone on Peanut Allergic Mouse Model:

TABLE 2

¹H NMR data of 1,3-Dihydroxyanthraquinone

| H | δ (m, Hz) |
|---|---|
| 2 | 6.53 (d, 2.4) |
| 4 | 7.14 (d, 2.4) |
| 5 | 8.16 (br. dd, 6.9, 2.4) |
| 6 | 7.78 (br.dd, 6.2) |
| 7 | 7.81 (br.dd, 6.2) |
| 8 | 8.22 (br. dd, 6.9, 2.4) |

Animals

Five-week-old female C3H/HeJ mice were purchased from the Jackson Laboratory (Bar Harbor, Me.). Mice were maintained on PN-free chow under specific pathogen-free conditions according to standard guidelines for the care and use of animals[39]. The study protocol was approved by institutional animal care and use committee at Icahn Mount Sinai School of Medicine, New York.

Peanut (PN) Sensitization and Challenge

Freshly ground, whole roasted peanuts were homogenized in sterile PBS (Mediatech, VA) until a smooth suspension was obtained. Female C3H/HeJ mice were sensitized intragastrically (i.g.) with ground PN (10 mg/mouse) and cholera toxin (20 µg), on three consecutive days at week 0, and once a week for 5 weeks, and boosted at weeks 6 and 8 with 50 mg/mouse of PN and cholera toxin (20 µg) (FIG. 37A) as previous described[40]. Mice were intragastrically administered with 400 µg of three different active compounds (arctiin and arctigenin from *Arctium lappa* L., and 1,3-Dihydroxyanthraquinone from *Rubia cordifolia* L.) daily 24 h after the week 8 boosting and under this treatment for 4 weeks. Eight PN sensitized/boosted mice receiving 0.5 ml of 0.1% DMSO in water twice daily for the same period of treatment time as sham control mice for this experiment.

TABLE 3

Peanut-Specific IgG1 and IgG2a Levels and IgG1:IgG2a ratios.

| Group | IgG1 (µ/ml, mean ± SEM) | IgG2 (µg/ml, mean ± SEM) | Ratio (IgG1/IgG2a) |
|---|---|---|---|
| 1 week Sham | 215.57 ± 20.84 | 216.57 ± 127.80 | 1.00 |
| 1 week Cream 3B | 278.92 ± 110.04 | 228.14 ± 112.22 | 1.22 |
| 1 week Naïve | 161.55 ± 18.98 | 134.00 ± 34.34 | 1.20 |

Assessment of Hypersensitivity Reactions.

Anaphylactic symptoms were evaluated 30 min after challenge dose by two investigators using a scoring system described previously: 1, no signs; 1, scratching and rubbing around the snout and head; 2, puffiness around the eyes and mouth, pilar erection and reduced activity with an increased respiratory rate; 3, wheezing, labored respiration and cyanosis around the mouth; 4, no activity after prodding, or tremors, and convulsion; 5, death due to anaphylaxis.

Results:

5 Herbal Medicines Improved the Uptake of Berberine by Caco-2 Cells:

Uptake of berberine by cultured monolayers of Caco-2 cells was examined. Mass spectra data of berberine at m/z 336 was detected in processed Cacao-2 cells (FIG. 34) incubated with berberine standard alone by using LC-MS. The same processing was performed on Cacao-2 cell samples incubated with berberine standard and each individual herbs of 9 herbal medicines. In all nine herbal medicines, only *Phellodendron chinensis* and *Coptis chinensis* contain berberine. All other 7 herbal medicines do not contain berberine in them. When incubated with berberine standard alone (50 µg/mL) for 1 hour, 2.95 µg/mL was taken by Cacao-2 cells. Incubation with 9 different herbal medicines, *Zingiber officinalis, Ganoderma lucidum, Phellodendron chinensis* and *Coptis chinensis* did not improve the berberine taken by cells. *Prunus mume, Angelica sinensis, Cinnamomum cassia, Zanthoxylum schinifolium,* and *Panax ginseng* improved the berberine concentration from 2.95 µg/mL to 6.15 µg/mL, 6.93 µg/mL, 4.51 µg/mL, 6.07 µg/mL, and 6.24 µg/mL respectively (Table 4).

TABLE 4

Concentration of berberine (µg/mL) presented in Cacao-2 cells incubated with herbal medicines alone or with Berberine standard

|  | −Berberine | +Berberine |
|---|---|---|
| Berberine STD | 2.95 |  |
| *Prunus mume* | 0.00 | 6.15 |
| *Phellodendron chinensis* | 0.76 | 3.94 |
| *Coptis chinensis* | 5.43 | 9.63 |
| *Zingiber officinalis* | 0.00 | 3.79 |
| *Ganoderma lucidum* | 0.00 | 2.81 |
| *Angelica sinensis* | 0.00 | 6.93 |
| *Cinnamomum cassia* | 0.00 | 4.51 |
| *Zanthoxylum schinifolium* | 0.00 | 6.07 |
| *Panax ginseng* | 0.00 | 6.24 |

*Angelica sinensis* Improved the Bioavailability of Berberine In Vivo

The bioavailability of berberine alone is very low. Our in vivo data showed that the berberine level is 0.28 µg/mL 1 hour after the oral feeding of 2 mg of berberine. The herbal medicine *Angelica sinensis* improved the bioavailability of berberine. The samples from mice fed with berberine+ *Angelica sinensis* showed increased concentration of berberine as 1.10 µg/mL, which is 4 times higher than that of oral feeding of berberine alone (Table 5).

TABLE 5

Concentration of berberine (µg/mL) presented in serum from mice treated with Berberine alone or berberine + *Angelica sinensis*

|  | −Berberine |
|---|---|
| Berberine STD | 0.28 |
| Berberine + *Angelica sinensis* | 1.10 |

Purpurin and Alizarin Identified from *Rubia cordifolia* L. Showed IgE-Inhibition Effect In Vitro:

Two compounds, purpurin and alizarin, were identified from *Rubia cordifolia* L. Their structures and HPLC fingerprint were showed in FIG. 35. In order to test their bioactivities on IgE production, both compounds were incubated with U266 cells at different concentrations. As shown in FIGS. 36A and 36B, both purpurin and alizarin inhibited the IgE production in a dose-dependent manner. The IC50 values of each compound were calculated as 0.3535 µg/mL and 0.7623 µg/mL respectively (FIGS. 36C and 36D).

Arctiin and Arctigenin from *Arctium lappa* L. Inhibited IgE Production In Vitro:

Two compounds isolated form *Arctium lappa* L. were identified as arctiin and arctigenin. Both compounds inhibited the IgE production by U266 in dose-dependent manner (FIG. 36C).

All Three Compounds Inhibited the IgE Production In Vivo, but 1,3-Dihydroxyanthraquinone was Most Effective in Preventing Peanut Anaphylaxis To test the IgE inhibition effect of arctiin, arctigenin, and 1,3-dihydroxyanthraquinone in vivo, we treated peanut allergic mice with 400 μg of each active compound daily for four weeks, as shown in FIG. 37A.[(2)]

Peanut induced anaphylaxis is IgE mediated type I hypersensitivity. At the time of week 15 post therapy challenge, all three compounds significantly decreased PN-specific IgE level (, $p<0.01$; *, $p<0.0001$; FIG. 37B) compared to the sham group.

1,3-Dihydroxyanthraquinone Shows the Most Effective Potency in Protecting the Mice Against Acute Peanut Induced Anaphylaxis:

Both Arctigenin and 1,3-Dihydroxyanthraquinone treated mice were protected against the acute anaphylaxis, but 1,3-dihydroxyanthraquinone showed the most effective potency. The median score was significant lower than that in the sham treated mice ($p<0.0001$; FIG. 37C). A decrease in body temperature is indicative of systemic anaphylaxis. As shown in FIG. 37D, sham-treated mice showed significantly decreased body temperature following PN challenge, while arctigenin and 1,3-Dihydroxyanthraquinone treated mice showed normal body temperatures (*, $p<0.05$; **, $p<0.01$).

Histamine is a major and well-recognized mediator of anaphylaxis. The levels of histamine in plasma were markedly elevated in sham treated mice after challenge (FIG. 37E). Arctigenin and 1,3-Dihydroxyanthraquinone treated mice showed significantly decreased amounts of histamine level at week 15 post therapy challenge compared with the Sham group of mice (*, $p<0.05$; **, $p<0.01$; FIG. 37E).

REFERENCES

[1] Branum A M, Lukacs S L. Food allergy among children in the United States. Pediatrics. 2009; 124:1549-1555.
[2] Leung D Y, Sampson H A, Yunginger J W et al. Effect of anti-IgE therapy in patients with peanut allergy. N Engl J Med. 2003; 348:986-993.
[3] Sampson H A, Leung D Y, Burks A W et al. A phase II, randomized, doubleblind, parallelgroup, placebocontrolled oral food challenge trial of Xolair (omalizumab) in peanut allergy. J Allergy Clin Immunol. 2011; 127:1309-1310.
[4] Nadeau K C, Schneider L C, Hoyte L, Borras I, Umetsu D T. Rapid oral desensitization in combination with omalizumab therapy in patients with cow's milk allergy. J Allergy Clin Immunol. 2011; 127:1622-1624.
[5] Schneider L C, Rachid R, LeBovidge J et al. A pilot study of omalizumab to facilitate rapid oral desensitization in high-risk peanut-allergic patients. J Allergy Clin Immunol. 2013; 132:1368-1374.
[6] Srivastava K D, Kattan J D, Zou Z M et al. The Chinese herbal medicine formula FAHF-2 completely blocks anaphylactic reactions in a murine model of peanut allergy. J Allergy Clin Immunol. 2005; 115:171-178.
[7] Song Y, Qu C, Srivastava K et al. Food allergy herbal formula 2 protection against peanut anaphylactic reaction is via inhibition of mast cells and basophils. J Allergy Clin Immunol. 2010; 126:1208-1217.
[8] Srivastava K, Yang N, Chen Y et al. Efficacy, safety and immunological actions of butanol-extracted Food Allergy Herbal Formula-2 on peanut anaphylaxis. Clin Exp Allergy. 2010; 41:582-591.
[9] Patil S P, Wang J, Song Y et al. Clinical safety of Food Allergy Herbal Formula-2 (FAHF-2) and inhibitory effect on basophils from patients with food allergy: Extended phase I study. J Allergy Clin Immunol. 2011;
[10] Wang J, Patil S, Yang N et al. Safety, tolerability, and immunologic effects of a food allergy herbal formula (FAHF-2) in food allergic individuals: a randomized, double-blinded, placebo-controlled, dose escalation phase I study. Ann Allergy Asthma Immunol. 2010; 105:75-84.
[11] The State Pharmacopoeia Commission of The People's Republic of China. Pharmacopoeia of the People's Republic of China. 2005; Version 6:1-791.
[12] Kattan J D, Srivastava K D, Zou Z M et al. Pharmacological and immunological effects of individual herbs in the Food Allergy Herbal Formula-2 (FAHF-2) on peanut allergy. Phytother Res. 2008; 22:651-659.
[13] The US Food and Drug Administration (FDA), Center for Drug Evaluation and Research. Guidance for Industry Botanical Drug Products. 2004; Revised:
[14] Jayaprakasam B, Doddaga S, Wang R et al. Licorice flavonoids inhibit eotaxin-1 secretion by human fetal lung fibroblasts in vitro. J Agric Food Chem. 2009; 57:820-825.
[15] Lopez-Exposito I, Castillo A, Yang N, Liang B, Li X M. Chinese herbal extracts of Rubia cordifolia and Dianthus superbus suppress IgE production and prevent peanut-induced anaphylaxis. Chin Med. 2011; 6:35-
[16] Yang N, Patil S, Zhuge J et al. Glycyrrhiza uralensis flavonoids present in anti-asthma formula, ASHMI, inhibit memory Th2 responses in vitro and in vivo. Phytother Res. 2013; 27:1381-1391.
[17] Breksa A P, III, Dragull K, Wong R Y. Isolation and identification of the first C-17 limonin epimer, epilimonin. J Agric Food Chem. 2008; 56:5595-5598.
[18] Hasada K, Yoshida T, Yamazaki T et al. Application of 1H-NMR spectroscopy to validation of berberine alkaloid reagents and to chemical evaluation of Coptidis Rhizoma. J Nat Med. 2011; 65:262-267.
[19] Chalubinski M, Grzegorczyk J, Kowalski M L. Glucocorticoid-induced immunoglobulin E synthesis by peripheral blood mononuclear cells from allergic and nonallergic subjects. Ann Allergy Asthma Immunol. 2011; 107: 251-257.
[20] Iwamoto K, Hiragun T, Takahagi S et al. Fucoidan suppresses IgE production in peripheral blood mononuclear cells from patients with atopic dermatitis. Arch Dermatol Res. 2011; 303:425-431.
[21] Oettgen H C. Regulation of the IgE isotype switch: new insights on cytokine signals and the functions of epsilon germline transcripts. Curr Opin Immunol. 2000; 12:618-623.
[22] Geha R S, Jabara H H, Brodeur S R. The regulation of immunoglobulin E class-switch recombination. Nat Rev Immunol. 2003; 3:721-732.
[23] Srivastava K D, Bardina L, Sampson H A, Li X M. Efficacy and immunological actions of FAHF-2 in a murine model of multiple food allergies. Ann Allergy Asthma Immunol. 2012; 108:351-358.
[24] Ehrman T M, Barlow D J, Hylands P J. Phytochemical databases of Chinese herbal constituents and bioactive plant compounds with known target specificities. J Chem Inf Model. 2007; 47:254-263.
[25] Ehrman T M, Barlow D J, Hylands P J. Phytochemical informatics of traditional Chinese medicine and therapeutic relevance. J Chem Inf Model. 2007; 47:2316-2334.
[26] Vuddanda P R, Chakraborty S, Singh S. Berberine: a potential phytochemical with multispectrum therapeutic activities. Expert Opin Investig Drugs. 2010; 19:1297-1307.

[27] Lou T, Zhang Z, Xi Z et al. Berberine inhibits inflammatory response and ameliorates insulin resistance in hepatocytes. *Inflammation.* 2011; 34:659-667.

[28] Shang W, Liu J, Yu X, Zhao J. [Effects of berberine on serum levels of inflammatory factors and inflammatory signaling pathway in obese mice induced by high fat diet]. *Zhongguo Zhong Yao Za Zhi.* 2010; 35:1474-1477.

[29] Hamsa T P, Kuttan G. Antiangiogenic activity of berberine is mediated through the downregulation of hypoxia-inducible factor-1, VEGF, and proinflammatory mediators. *Drug Chem Toxicol.* 2012; 35:57-70.

[30] Lan T, Wu T, Chen C et al. Berberine attenuates high glucose-induced proliferation and extracellular matrix accumulation in mesangial cells: Involvement of suppression of cell cycle progression and NF-kappaB/AP-1 pathways. *Mol Cell Endocrinol.* 2014; 384:109-116.

[31] Bacharier L B, Geha R S. Molecular mechanisms of IgE regulation. *J Allergy Clin Immunol.* 2000; 105:S547-S558.

[32] Altin J, Shen C, Liston A. Understanding the genetic regulation of IgE production. *Blood Rev.* 2010; 24:163-169.

[33] Torgerson T R, Linane A, Moes N et al. Severe food allergy as a variant of IPEX syndrome caused by a deletion in a noncoding region of the FOXP3 gene. *Gastroenterology.* 2007; 132:1705-1717.

[34] Vale-Pereira S, Todo-Bom A, Geraldes L et al. FoxP3, GATA-3 and T-bet expression in elderly asthma. *Clin Exp Allergy.* 2011; 41:490-496.

[35] Mantena S K, Sharma S D, Katiyar S K. Berberine, a natural product, induces G1-phase cell cycle arrest and caspase-3-dependent apoptosis in human prostate carcinoma cells. *Mol Cancer Ther.* 2006; 5:296-308.

[36] Chai Y S, Yuan Z Y, Lei F et al. Inhibition of retinoblastoma mRNA degradation through Poly (A) involved in the neuroprotective effect of berberine against cerebral ischemia. *PLoS One.* 2014; 9:e90850-

[37] Roy A, Saraf S. Limonoids: overview of significant bioactive triterpenes distributed in plants kingdom. *Biol Pharm Bull.* 2006; 29:191-201.

[38] Manners G D. Citrus limonoids: analysis, bioactivity, and biomedical prospects. *J Agric Food Chem.* 2007; 55:8285-8294.

[39] Institute of Laboratory Animal Resources Commission of Life Sciences NRC. Guide for the Care and Use of Laboratory Animals. Washington D.C.: National Academy Press, 1996.

[40] Qu C, Srivastava K, Ko J, Zhang T F, Sampson H A, Li X M. Induction of tolerance after establishment of peanut allergy by the food allergy herbal formula-2 is associated with up-regulation of interferon-gamma. Clin Exp Allergy 2007; 37(6):846-55.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

What is claimed is:

1. A method for treating and/or mitigating a food allergy in a subject in need thereof, which method comprises administering to the subject a therapeutically effective amount of an isolated and purified compound selected from the group consisting of berberine, limonin, and 1,3-Dihydroxyanthraquinone, or a combination of isolated and purified compounds selected from the group consisting of berberine, limonin, and 1,3-Dihydroxyanthraquinone.

2. The method of claim 1 where the food allergy is peanut allergy.

3. The method of claim 1 wherein the subject is human.

* * * * *